US 6,748,262 B2

(12) United States Patent
Harada et al.

(10) Patent No.: US 6,748,262 B2
(45) Date of Patent: Jun. 8, 2004

(54) HEARTBEAT SYNCHRONOUS INFORMATION ACQUIRING APPARATUS

(75) Inventors: Chikao Harada, Komaki (JP); Keizoh Kawaguchi, Komaki (JP); Kiyoyuki Narimatsu, Komaki (JP); Akihiro Yokozeki, Komaki (JP)

(73) Assignee: Colin Medical Technology Corporation, Komaki (JP)

(*) Notice: Subject to any disclaimer, the term of this patent is extended or adjusted under 35 U.S.C. 154(b) by 357 days.

(21) Appl. No.: 09/924,512

(22) Filed: Aug. 9, 2001

(65) Prior Publication Data

US 2003/0032887 A1 Feb. 13, 2003

(51) Int. Cl.[7] .................................................. A61B 5/02
(52) U.S. Cl. .................. 600/513; 600/506; 600/547
(58) Field of Search ........................ 600/300–301, 600/481, 483, 485, 500, 502, 504, 506, 508–510, 513, 547

(56) References Cited

U.S. PATENT DOCUMENTS

| 5,671,750 A | * | 9/1997 | Shinoda | 600/495 |
| 5,743,857 A | * | 4/1998 | Shinoda et al. | 600/496 |
| 6,491,638 B2 | * | 12/2002 | Oka | 600/494 |
| 6,616,608 B2 | * | 9/2003 | Honda et al. | 600/301 |
| 6,626,842 B2 | * | 9/2003 | Oka | 600/528 |

FOREIGN PATENT DOCUMENTS

| JP | A 9-322884 | 12/1997 |
| JP | A 9-322885 | 12/1997 |
| JP | A 9-322886 | 12/1997 |

* cited by examiner

Primary Examiner—Kennedy Schaetzle
Assistant Examiner—Kristen Droesch
(74) Attorney, Agent, or Firm—Oliff & Berridge, PLC

(57) ABSTRACT

The gate means 73 extracts the partial impedance pulse wave $SM_{IMP(P)}$ from the thorax impedance pulse wave $SM_{IMP}$ detected by the thorax impedance pulse wave detector 64. This is done over an intake period defined as a period starting from a first time $T_1$ after the time when the R wave of the induced electro-cardiac wave is detected to the time when a rising edge of the photoelectric pulse wave $SM_2$ is detected. Then, the heartbeat synchronous information determining means 74 selects a rising edge of the partial impedance pulse wave $SM_{IMP(P)}$ that periodically appears as heartbeat synchronous information $I_H$. Thus, it is possible to accurately determine the heartbeat synchronous information $I_H$. Additionally, since the photoelectric pulse wave $SM_2$ that is detected by the photoelectric pulse wave sensor 40 is largely free of noise it is possible to accurately determine the end of the period for reading the thorax impedance pulse wave $SM_{IMP}$.

3 Claims, 34 Drawing Sheets

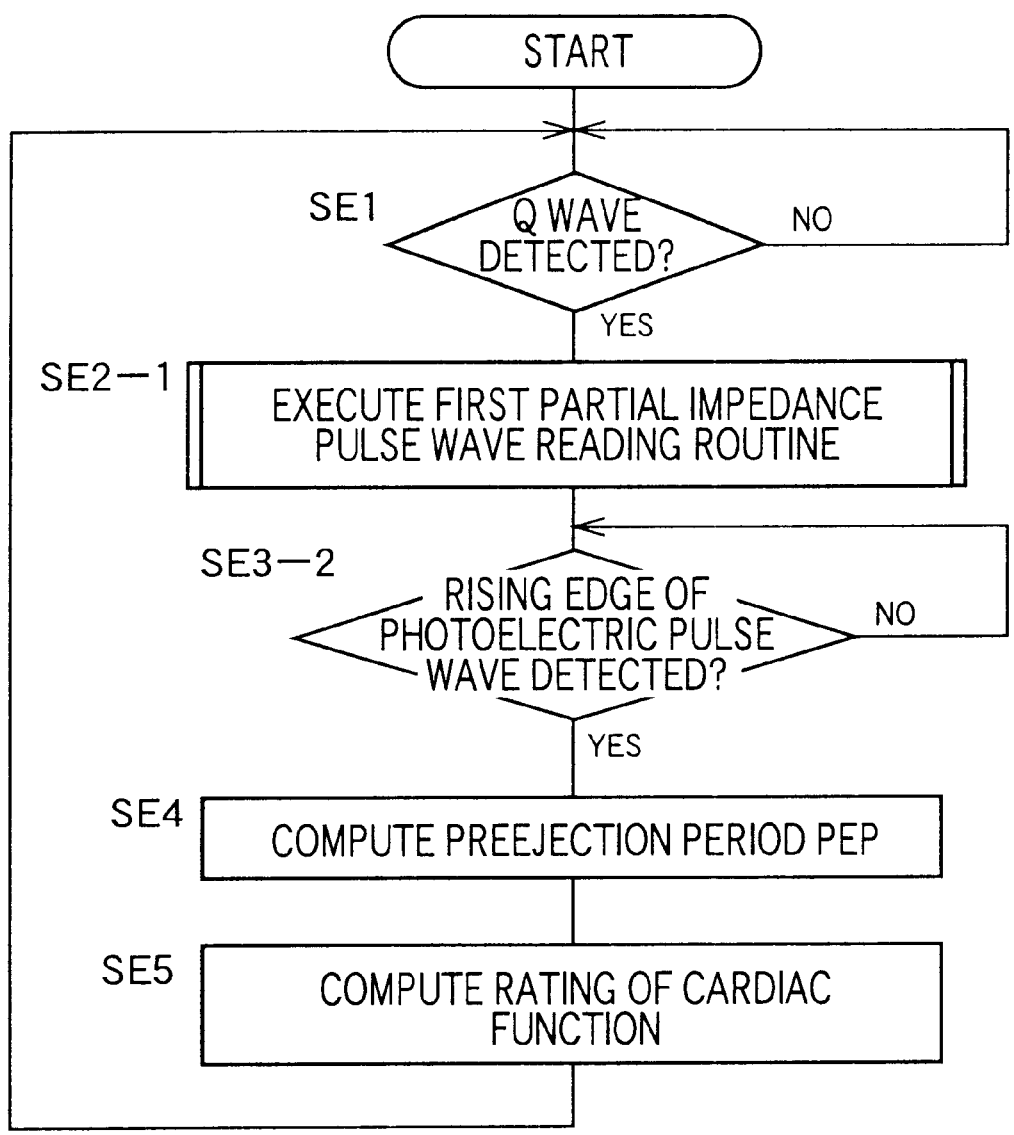

HEARTBEAT SYNCHRONOUS INFORMATION ACQUIRING APPARATUS

BACKGROUND OF THE INVENTION

1. Field of the Invention

This invention relates to a heartbeat synchronous information acquiring apparatus for determining heartbeat synchronous information based on an impedance pulse wave of a living body. The present information also relates to a pulse wave propagation velocity related information acquiring apparatus, a blood pressure monitoring apparatus and a preejection period measuring apparatus adapted to utilize the acquired heartbeat synchronous information. As far as this patent application is concerned, the expression "heartbeat synchronous information" refers to a predetermined part of a heartbeat synchronous pulse wave.

2. Detailed Description of the Related Art

The impedance between two bodily positions with the heart interposed between them involves changes in the impedance attributable to expansions and contractions of the heart that are expressed in the form of an impedance pulse wave composed of heartbeat synchronous components. Apparatus for acquiring various pieces of bio-information by utilizing the heartbeat synchronous information determined as a function of the impedance pulse wave have been proposed to date.

For instance, the applicant of the present patent application has proposed in Japanese Patent Application No. 8-142597 an apparatus for determining heartbeat synchronous information as a function of the impedance pulse wave of a living body and measuring the pulse wave propagation velocity at which a pulse wave propagates in a living body by utilizing the obtained heartbeat synchronous information. Additionally, the applicant of the present patent application has proposed in Japanese Patent Application No. 8-142596 a blood pressure monitoring apparatus for determining heartbeat synchronous information as a function of the impedance pulse wave of a living body, continually computing the pulse wave propagation velocity at which the pulse wave propagates in a living body by utilizing the obtained heartbeat synchronous information and then monitoring a blood pressure based on the obtained pulse wave propagation velocity. Furthermore, the applicant of the present patent application has proposed in Japanese Patent Application No. 8-142598 a preejection period measuring apparatus for computing a preejection period from a time lag between a predetermined part of an induced electro-cardiac wave and a corresponding predetermined part of the impedance pulse wave (or heartbeat synchronous information) of a living body.

When acquiring various pieces of bio-information by utilizing the heartbeat synchronous information determined as a function of the impedance pulse wave of a living body, it is absolutely essential that the heartbeat synchronous information is determined accurately. However, the impedance of a living body is in fact a micro-signal that needs to be amplified by about 10,000 times (to about 80 dB) when it is to be perceived as a signal. As the micro-signal is amplified, induction noise surrounding a subject and radiation noise from unrelated devices become apparent making the signal less recognizable. Additionally, the blood of the subject moving through blood vessels can give rise to noise along with the impedance pulse wave. Furthermore, the impedance can change as the subject moves, which in turn moves electrodes fitted to the subject. Therefore, the noise detected along with the impedance pulse wave can sometimes make it impossible to accurately determine the heartbeat synchronous information of the subject. For instance, when determining the heartbeat synchronous information from consecutive peaks of heartbeats in the impedance pulse wave, the amplitudes of the peaks of high noise can be greater than those of the peaks of the heartbeats. Consequently, noise which shows a large amplitude can be determined as heartbeat synchronous information.

SUMMARY OF THE INVENTION

In view of the above identified circumstances, the object of the present invention is to provide a heartbeat synchronous information acquiring apparatus that can accurately determine heartbeat synchronous information as well as a pulse wave propagation velocity related information acquiring apparatus, a blood pressure monitoring apparatus, and a preejection period measuring apparatus adapted to utilize the acquired heartbeat synchronous information.

As a result of intensive research efforts carried but to achieve the above object, the inventor of the present invention has found that it is possible to accurately determine the heartbeat synchronous information by extracting an impedance pulse wave for a predetermined period, which is a time span long enough to generate such heartbeat synchronous information, out of a continuously detected impedance pulse wave. This is done by using an induced electro-cardiac wave adapted to produce a signal greater than a signal of an impedance of a living body, and hence less affected by noise. The heartbeat synchronous information is then determined from an extracted partial impedance pulse wave because the heartbeat synchronous information is not affected by noise other than that of the extracted part. This invention is based on this finding.

The First Aspect of the Invention

In the first aspect of the invention, there is provided a heartbeat synchronous information acquiring apparatus provided with an impedance pulse wave detector for detecting an impedance pulse wave of a living body, containing heartbeat synchronous components, between a pair of electrodes fitted to predetermined positions of the living body with the heart interposed between them. This is done in order to acquire the heartbeat synchronous information, generated synchronously with heartbeats of the living body, based on the impedance pulse wave. The apparatus is composed of (a) an induced electro-cardiac wave detection device for continuously detecting an induced electro-cardiac wave of the living body, and (b) a gate means for extracting a partial impedance pulse wave from the impedance pulse wave by taking in the impedance pulse wave for an intake period based on a time of detection of a predetermined part of the induced electro-cardiac wave by the electro-cardiac wave detection device. There is also (c) a heartbeat synchronous information determining means for determining a periodically appearing predetermined part of the partial impedance pulse wave extracted by the gate means as heartbeat synchronous information.

Advantages the First Aspect of the Invention

With the above described arrangement, the partial impedance pulse wave is extracted by the gate means from the impedance pulse wave. The partial impedance pulse wave is detected by the impedance pulse wave detector by taking in the impedance pulse wave for the intake period based on the time of detection of the predetermined part of the induced electro-cardiac wave. The periodically appearing predetermined part of the partial impedance pulse wave extracted by the gate means is determined as heartbeat synchronous information by the heartbeat synchronous information determining means. Thus, it is now possible to accurately acquire heartbeat synchronous information.

Other Modes of Carrying out the Invention in the First Aspect

Preferably, the intake period of the gate means is from the end of a predetermined first time period starting from the time of detection of the predetermined part of the induced electro-cardiac wave by the electro-cardiac wave detection device to the end of a predetermined second time period starting from the time of detection of the predetermined part. The second time period is longer than the first time period. With this arrangement, the intake period is determined only based on a part of the induced electro-cardiac wave that is less affected by noise so that the intake period can be determined accurately, and it is no longer necessary to provide an additional device for determining the intake period. It will be appreciated that, if the intake period is not determined accurately, the partial impedance pulse wave may contain unnecessary parts, or may not contain the necessary part, which is the heartbeat synchronous information.

Preferably, the heartbeat synchronous information acquiring apparatus is further composed of a light source for irradiating the skin of the living body with light, a photo detector for detecting transmitted or reflected light originating from the light source, and a photoelectric pulse wave sensor for detecting the photoelectric pulse wave at a bodily part irradiated with light emitted from the light source. The intake period of the gate means is from the end of the first time period starting from the time of detection of the predetermined part of the induced electro-cardiac wave by the electro-cardiac wave detection device to the time of detection of the predetermined part of the photoelectric pulse wave by the photoelectric pulse wave sensor. With this arrangement, the end of the intake period can be determined accurately because the photoelectric pulse wave detected by the photoelectric pulse wave sensor is largely free of electromagnetic noise. It will be appreciated that, if the intake period is not determined accurately, the partial impedance pulse wave may contain unnecessary parts, or may not contain the necessary part, which is the heartbeat synchronous information.

The Second Aspect of the Invention

In the second aspect of the invention, there is provided a blood pressure monitoring apparatus for monitoring the blood pressure of a living body. The apparatus is composed of (a) a blood pressure measuring means for measuring the blood pressure of the living body by using a cuff for pressing the artery of the living body, and (b) an induced electro-cardiac wave detection device for continuously detecting an induced electro-cardiac wave of said living body. There is also (c) an impedance pulse wave detector, for detecting an impedance pulse wave of a living body containing heartbeat synchronous components, between a pair of electrodes fitted to predetermined positions of the living body with the heart interposed between them, (d) a gate means for extracting a partial impedance pulse wave from the impedance pulse wave by taking in the impedance pulse wave for an intake period based on a time of detection of a predetermined part of the induced electro-cardiac wave by the electro-cardiac wave detection device, and (e) a pulse wave detector fitted to a part of the living body for detecting a pulse wave propagating through the artery of the living body In addition there is (f) a pulse wave propagation velocity related information computing means for continually computing information on a pulse wave propagation velocity based on the partial impedance pulse wave and the pulse wave propagating through the artery of the living body, and (g) a propagation velocity related information versus blood pressure relationship determining means for determining the relationship between propagation velocity related information computed by the pulse wave propagation velocity related information computing means and a blood pressure measured by the blood pressure measuring means at each time of such measurement. Also there is (h) a monitored blood pressure determining means for continually determining a value of the monitored blood pressure from the corresponding relationship between the propagation velocity related information and the blood pressure as determined by the propagation velocity related information versus blood pressure relationship determining means based on the actual pulse wave propagation velocity related information computed by the pulse wave propagation velocity related information computing means.

Advantages of the Second Aspect of the Invention

With the above described arrangement, each time the blood pressure is measured by the blood pressure measuring means, the propagation velocity related information versus blood pressure relationship determining means determines the corresponding relationship between the propagation velocity related information computed by the pulse wave propagation velocity related information computing means and the blood pressure measured by the blood pressure measuring means. The monitored blood pressure determining means continually determines the value of the monitored blood pressure from the corresponding relationship between the propagation velocity related information and the blood pressure. The blood pressure is determined by the propagation velocity related information versus blood pressure relationship determining means based on the actual pulse wave propagation velocity related information computed by the pulse wave propagation velocity related information computing means. The pulse wave propagation velocity related information computed by the pulse wave propagation velocity related information computing means is accurate because it is computed based on the partial impedance pulse wave taken in only in the intake period as determined by the gate means based on the time of detection of the predetermined part of the induced electro-cardiac wave. Therefore the value of the monitored blood pressure is highly reliable because it is continually determined by the monitored blood pressure determining means based on the accurate pulse wave propagation velocity related information.

Other Modes of Carrying out the Invention in the Second Aspect

Preferably, the blood pressure monitoring apparatus further includes a monitored blood pressure abnormality judging means for judging the normality or abnormality of the value of the monitored blood pressure as determined by said monitored blood pressure determining means. This is done by referring to a predetermined judgment reference range and triggering the operation of the blood pressure measuring means when the value of the monitored blood pressure is judged to be an abnormal value. With this arrangement, whenever the value of the monitored blood pressure is judged to be an abnormal value, an operation of measuring the blood pressure, using a cuff, is carried out immediately by the blood pressure measuring means and the corresponding relationship between the propagation velocity related information and the blood pressure is determined for another time by the propagation velocity related information versus blood pressure relationship determining means. Therefore, an updated and hence reliable blood pressure value is automatically obtained by means of the cuff whenever an abnormal value is observed for the monitored blood pressure so improving the reliability of the succeeding operation of monitoring the blood pressure.

Preferably, the blood pressure monitoring apparatus further includes a display for showing the trend of the monitored blood pressure values that are continually determined by the monitored blood pressure determining means. With this arrangement, the trend in the changes in the blood pressure that have been observed can be accurately recognized so making the doctor's diagnosis easier and more accurate.

Preferably, the display is adapted to show an alarm for whenever the monitored blood pressure value is judged to be abnormal by the monitored blood pressure abnormality judging means. With this arrangement, by way of the alarm, the operator/doctor is reliably made aware of an abnormal condition of the living body or, at least, an abnormal condition of the blood pressure monitoring apparatus.

Preferably, the pulse wave detector is composed of the cuff which is wound around a living body and a cuff pulse wave discriminating circuit for extracting a cuff pulse wave that is a pressurized vibration of the cuff. With this arrangement, if the pulse wave detector is used with the blood pressure measuring apparatus, the cuff of the blood pressure measuring apparatus can be shared with the pulse wave detector for the purpose of pulse wave detection. This arrangement is a great advantage in terms of cost and simplicity.

Preferably, the pulse wave detector is composed of a pressure pulse wave sensor for detecting a pressure pulse wave that is generated in the artery of the living body as the artery is pressed via the skin of the living body. With this arrangement, particularly when it is used with a continuous blood pressure measuring apparatus for continuously measuring an arterial pressure by detecting the pressure pulse wave of the radial artery by means of the pressure pulse wave sensor, the pressure pulse wave sensor of the continuous blood pressure measuring apparatus can be shared by the pulse wave detector to reduce the cost of the latter.

The Third Aspect of the Invention

In the third aspect of the invention, there is provided a blood pressure monitoring apparatus provided with a blood pressure measuring means for measuring the blood pressure of a living body by periodically shifting a pressure of a cuff that is fitted to and pressing against the living body in a predetermined cycle based on a pulse synchronous wave generated in the process of shifting the pressure pressing against the living body. The apparatus is composed of (a) an electro-cardiac wave detection device for continuously detecting an induced electro-cardiac wave of the living body, and (b) an impedance pulse wave detector, for detecting an impedance pulse wave of the living body containing heartbeat synchronous components, between a pair of electrodes fitted to predetermined positions of the living body with the heart interposed between them. There is also (c) a gate means for extracting a partial impedance pulse wave from the impedance pulse wave by taking in the impedance pulse wave for an intake period based on a time of detection of a predetermined part of the induced electro-cardiac wave by the electro-cardiac wave detection device, and (d) a pulse wave detector fitted to a part of the living body for detecting a pulse wave propagating through an artery of the living body. In addition there is (e) a pulse wave propagation velocity related information computing means for continually computing information on a pulse wave propagation velocity based on the partial impedance pulse wave and the pulse wave propagating through the artery of the living body, and (f) a monitored blood pressure change judging means for judging a change in a blood pressure of the living body based on any change in the pulse wave propagation velocity related information, continually computed by the pulse wave propagation velocity related information computing means, which exceeds a predetermined judgment reference value.

Advantages of the Third Aspect of the Invention

With the above described arrangement, a change in the blood pressure of the living body is judged by the monitored blood pressure change judging means based on any change in the pulse wave propagation velocity related information, continually computed by the pulse wave propagation velocity related information computing means, which exceeds the predetermined judgment reference value. The pulse wave propagation velocity related information computed by the pulse wave propagation velocity related information computing means is accurate and highly reliable because it is computed based on the partial impedance pulse wave taken in only in the intake period. The partial impedance pulse wave taken in only in the intake period is determined by the gate means based on the time of detection of the predetermined part of the induced electro-cardiac wave and the judgment on the change in the blood pressure of the living body that is done by the monitored blood pressure change judging means based on the accurate pulse wave propagation velocity related information.

Other Modes of Carrying out the Invention in the Third Aspect

Preferably, the monitored blood pressure change judging means is adapted to trigger the operation of the blood pressure measuring means when it judges a change in the blood pressure of the living body to be abnormal. Then, whenever it is judged by the monitored blood pressure change judging means that an abnormal condition exists with respect to the blood pressure of the living body, an operation of measuring the blood pressure, using the cuff, is carried out immediately by the blood pressure measuring means. Therefore, an updated and hence reliable blood pressure value is automatically obtained by means of the cuff at the time of judgment on the change in the blood pressure of the living body.

Other Modes of Carrying out the Invention in the Second and Third Aspects

Preferably, the intake period of the gate means of the blood pressure monitoring apparatus is from the end of a predetermined first time period, starting from the time of detection of the predetermined part of the induced electro-cardiac wave by the electro-cardiac wave detection device, to an end of a predetermined second time period, starting from the time of detection of the predetermined part. The second time period is longer than the first time period. With this arrangement, the intake period is determined only based on a part of the induced electro-cardiac wave that is less affected by noise so that the intake period can be determined accurately, and it is no longer necessary to provide an additional device for determining the intake period.

Preferably, the pulse wave detector includes a photoelectric pulse wave sensor for detecting a photoelectric pulse wave at a bodily part irradiated with light which includes a light source for irradiating the skin of the living body with light and a photodetector for detecting transmitted or reflected light originating from the light source. The intake period of the gate means is from the end of the first time period, starting from the time of detection of the predetermined part of the induced electro-cardiac wave by the electro-cardiac wave detection device, to the time of detection of the predetermined part of the photoelectric pulse wave by the photoelectric pulse wave sensor. With this arrangement, pulse wave propagation velocity related information can be continually computed by the pulse wave propagation velocity related information computing means based on the partial impedance pulse wave and the photoelectric pulse wave. The end of the intake period during which the impedance pulse wave is taken in by the gate means is determined based on the photoelectric pulse wave so that the photoelectric pulse wave sensor for computing the pulse wave propagation velocity related information can also be advantageously used for determining the end of the intake period. The intake period can be determined accurately because the photoelectric pulse wave detected by the photoelectric pulse wave sensor is largely free of electromagnetic noise.

Preferably, the impedance pulse wave detector of the blood pressure monitoring apparatus includes an impedance detector for detecting an impedance of the living body between the two electrodes, fitted to predetermined positions of the living body, with the heart of the living body interposed between them. There is also an impedance pulse wave discriminator for discriminating the impedance pulse wave, containing heartbeat synchronous components, from the impedance of the living body detected by the impedance detector. The impedance obtained by way of the pair of electrodes, fitted to predetermined positions of the living body with the heart interposed between them, includes a respiration impedance wave that changes synchronously with a respiration of the living body and the impedance pulse wave that changes synchronously with the heartbeat of the living body. The respiration impedance wave and the impedance pulse wave are laid one on top of the other so that the impedance pulse wave can be easily isolated to the great advantage of the apparatus.

Preferably, the pulse wave detector is composed of a photoelectric pulse wave sensor including a light source for emitting rays of red light or infrared rays adapted to be reflected by hemoglobin toward the skin of the living body, and a photo detector for detecting transmitted or reflected rays of red light or infrared rays originating from the light source. With this arrangement, when the photoelectric pulse wave sensor is used with a pulse oximeter which includes a photoelectric pulse wave sensor for detecting the pulse wave by using light showing two wavelengths for irradiation, the photoelectric pulse wave sensor of the pulse oximeter can be shared by the pulse wave detector to reduce the cost of the latter.

The Fourth Aspect of the Invention

In the fourth aspect of the invention, there is provided a pulse wave propagation velocity related information acquiring apparatus for acquiring information relating to a propagation velocity of a pulse wave propagating through an artery of a living body. The apparatus is composed of (a) an electro-cardiac wave detection device for continuously detecting an induced electro-cardiac wave of the living body, and (b) an impedance pulse wave detector for detecting an impedance pulse wave of the living body, containing heartbeat synchronous components, between a pair of electrodes fitted to predetermined positions of the living body with the heart interposed between them. There is also (c) a gate means for extracting a partial impedance pulse wave from the impedance pulse wave by taking in the impedance pulse wave for an intake period based on the time of detection of a predetermined part of the induced electro-cardiac wave by the electro-cardiac wave detection device, and (d) a pulse wave detector fitted to a part of the living body for detecting the pulse wave propagating through the artery of the living body. In addition there is (e) a pulse wave propagation velocity related information computing means for computing information on the velocity of the pulse wave propagating through the living body based on a time difference obtained by subtracting a second time difference from a first time difference. The first time difference is computed as the time difference between a time a predetermined part in the induced electro-cardiac wave detected by the induced electro-cardiac wave detection device periodically appears and a time a predetermined part in the pulse wave detected by the pulse wave detector periodically appears. The second time difference is computed as the time difference between a time the predetermined part in the induced electro-cardiac wave periodically appears and a time a predetermined part in the partial impedance pulse wave extracted by the gate means periodically appears.

Advantages of the Fourth Aspect of the Invention

With the above described arrangement, the partial impedance pulse wave is extracted by the gate means from the impedance pulse wave detected by the impedance pulse wave detector by taking in the impedance pulse wave for an intake period based on the time of detection of the predetermined part of the induced electro-cardiac wave. The pulse wave propagation velocity related information computing means computes the first time difference which is the time difference between the time the predetermined part in the induced electro-cardiac wave detected by the induced electro-cardiac wave detection device periodically appears and the time the predetermined part in the pulse wave detected by the pulse wave detector periodically appears. The pulse wave propagation velocity related information computing means computes the second time difference which is the time difference between the time the predetermined part in the induced electro-cardiac wave periodically appears and the time the predetermined part in the partial impedance pulse wave extracted by the gate means periodically appears. Then, the pulse wave propagation velocity related information computing means computes information on the velocity of the pulse wave propagating through the living body based on the time difference obtained by subtracting the second time difference from the first time difference. In other words, the second time difference is computed by using the periodically appearing predetermined part of the impedance pulse wave that is relatively free from noise and therefore accurate. Then, the pulse wave propagation velocity related information is computed based on the accurate second time difference and therefore it is accurate and reliable.

The Fifth Aspect of the Invention

In the fifth aspect of the invention, there is provided a pulse wave propagation velocity related information acquiring apparatus for acquiring information relating to a propagation velocity of a pulse wave propagating through an artery of a living body. The apparatus is composed of (a) an electro-cardiac wave detection device for continuously detecting an induced electro-cardiac wave of the living body, and (b) an impedance pulse wave detector for detecting an impedance pulse wave of the living body, containing heartbeat synchronous components, between a pair of electrodes fitted to predetermined positions of the living body with the heart interposed between them. There is (c) a gate means for extracting a partial impedance pulse wave from the impedance pulse wave by taking in the impedance pulse wave for an intake period based on a time of detection of a predetermined part of the induced electro-cardiac wave by the electro-cardiac wave detection device, and (d) a pulse wave detector fitted to a part of the living body for detecting the pulse wave propagating through the artery of the living body. In addition there is (e) a pulse wave propagation velocity related information computing means for computing information on a velocity of the pulse wave propagating through the living body based on a time difference between a time a predetermined part in the partial impedance pulse wave extracted by the gate means periodically appears and a time a predetermined part in the pulse wave detected by the pulse wave detector periodically appears.

Advantages of the Fifth Aspect of the Invention

With the above described arrangement, the partial impedance pulse wave is extracted by the gate means from the impedance pulse wave detected by the impedance pulse wave detector by taking in the impedance pulse wave for the intake period based on the time of detection of a predetermined part of the induced electro-cardiac wave. The pulse wave propagation velocity related information computing means computes information on the pulse wave propagation velocity based on the time difference between the time the predetermined part in the partial impedance pulse wave extracted by the gate means periodically appears and the time the predetermined part in the pulse wave detected by the pulse wave detector periodically appears. In other words, the time difference is computed by using the periodically appearing predetermined part of the impedance pulse wave that is relatively free from noise as a starting point and therefore it is accurate. Then, the pulse wave propagation velocity related information is computed based on the accurate time difference and therefore it is accurate and reliable.

Other Modes of Carrying out the Invention in the Fourth and Fifth Aspects

Preferably, the impedance pulse wave detector of the pulse wave propagation velocity related information acquiring apparatus includes an impedance detector for detecting the impedance of the living body between the two electrodes fitted to predetermined positions of the living body with the heart of the living body interposed between them, and an impedance pulse wave discriminator for discriminating the impedance pulse wave containing heartbeat synchronous components from the impedance of the living body detected by the impedance detector. The impedance, obtained by way of the pair of electrodes fitted to predetermined positions of the living body with the heart interposed between them, includes a respiration impedance wave that changes synchronously with a respiration of the living body and an impedance pulse wave that changes synchronously with the heartbeat of the living body. The respiration impedance wave and the impedance pulse wave are laid one on top of the other so that the impedance pulse wave can be easily isolated to the great advantage of the apparatus.

Preferably, the pulse wave detector is composed of a cuff to be wound around the living body and a cuff pulse wave discriminating circuit for extracting a cuff pulse wave that is a pressurized vibration of the cuff. With this arrangement, if the pulse wave detector is used with a blood pressure measuring apparatus, the cuff of the blood pressure measuring apparatus can be shared by the pulse wave detector for the purpose of pulse wave detection. This arrangement has a great advantage in terms of cost and simplicity.

Preferably, the pulse wave detector includes a pressure pulse wave sensor for detecting a pressure pulse wave that is generated in the artery of the living body as the artery is pressed via the skin of the living body. With this arrangement, particularly when it is used with a continuous blood pressure measuring apparatus for continuously measuring an arterial pressure by detecting the pressure pulse wave of a radial artery by means of the pressure pulse wave sensor, the pressure pulse wave sensor of the continuous blood pressure measuring apparatus can be shared by the pulse wave detector to reduce the cost of the pulse wave detector.

Preferably, the pulse wave detector is composed of a photoelectric pulse wave sensor, including a light source for irradiating the skin of the living body with rays of light, and a photo detector for detecting transmitted or reflected rays of light originating from the light source. With this arrangement, when it is used with a pulse oximeter which includes a photoelectric pulse wave sensor for detecting the pulse wave by using light showing two wavelengths for irradiation, the photoelectric pulse wave sensor of the pulse oximeter can be shared by the pulse wave detector to reduce the cost of the pulse wave detector.

Preferably, the intake period of the gate means of the pulse wave propagation velocity related information acquiring apparatus is from the end of a predetermined first time period, starting from the time of detection of the predetermined part of the induced electro-cardiac wave by the electro-cardiac wave detection device, to the end of a predetermined second time period, starting from the time of detection of the predetermined part. The second time period is longer than the first time period. With this arrangement, the intake period is determined only based on a part of the induced electro-cardiac wave that is less affected by noise. Therefore, the intake period can be determined accurately and it is no longer necessary to obtain any additional information for determining the intake period.

Preferably, the pulse wave propagation velocity related information acquiring apparatus includes the photoelectric pulse wave sensor as the pulse wave detector. It is also preferable that the intake period of the gate means is from the end of the first time period, starting from the time of detection of the predetermined part of the induced electro-cardiac wave by the electro-cardiac wave detection device, to the time of detection of the predetermined part of the photoelectric pulse wave by the photoelectric pulse wave sensor. With this arrangement, the end of the intake period for the gate means to read the impedance pulse wave is determined based on the photoelectric pulse wave. Therefore, the photoelectric pulse wave sensor for computing the pulse wave propagation velocity related information can also be used for determining the end of the intake period. The end of the intake period can be determined accurately because the photoelectric pulse wave detected by the photoelectric pulse wave sensor is largely free of electromagnetic noise.

The Sixth Aspect of the Invention

In the sixth aspect of the invention, there is provided a preejection period measuring apparatus for measuring a preejection period from the start of a contraction of the heart of a living body to the time when blood is ejected out from the heart by the heartbeat. The apparatus is composed of (a) an electro-cardiac wave detection device for detecting an induced electro-cardiac wave of the living body, and (b) an impedance pulse wave detector for detecting an impedance pulse wave of a living body containing heartbeat synchronous components between a pair of electrodes fitted to predetermined positions of the living body with the heart interposed between them. There is also (c) a gate means for extracting a partial impedance pulse wave from the impedance pulse wave by taking in the impedance pulse wave for an intake period as determined based on the time of detection of a predetermined part of the induced electro-cardiac wave by the electro-cardiac wave detection device, and (d) a pulse wave detector fitted to a part of the living body for detecting a pulse wave propagating through an artery of the living body. In addition there is (f) a preejection period computing means for computing the preejection period by subtracting a second time difference from a first time difference. The first time difference is computed as the time difference between a time a predetermined part in the induced electro-cardiac wave detected by the induced electro-cardiac wave detection device periodically appears and a time a predetermined part in the pulse wave detected by the pulse wave detector periodically appears. The second time difference is computed as the time difference between a time a predetermined part in partial impedance pulse wave extracted by the gate means periodically appears and a time the predetermined part in the pulse wave detected by the pulse wave detector periodically appears.

Advantages of the Sixth Aspect of the Invention

With the above described arrangement, the partial impedance pulse wave is extracted by the gate means from the impedance pulse wave detected by the impedance pulse wave detector by taking in the impedance pulse wave for the intake period as determined based on the time of detection of the predetermined part of the induced electro-cardiac wave. The preejection period computing means computes the first time difference which is the time difference between the time the predetermined part in the induced electro-cardiac wave detected by the induced electro-cardiac wave detection device periodically appears and the time the predetermined part in the pulse wave detected by the pulse wave detector periodically appears. The preejection period computing means also computes the second time difference which is the time difference between the time the predetermined part in partial impedance pulse wave extracted by the gate means periodically appears and the time the predetermined part in the pulse wave detected by the pulse wave detector periodically appears, and then computes the preejection period by subtracting the second time difference from the first time difference. In other words, the second time difference is computed by using as a starting point the periodically appearing predetermined part of the impedance pulse wave that is relatively free from noise, and therefore it is accurate. Then, the preejection period is computed by subtracting the accurate second time difference from the first time difference, and therefore it is accurate and reliable.

The Seventh Aspect of the Invention

In the seventh aspect of the invention, there is provided a preejection period measuring apparatus for measuring a preejection period from the start of a contraction of the heart of a living body to a time when blood is ejected out from the heart by the heartbeat. The apparatus is composed of (a) an electro-cardiac wave detection device for detecting an induced electro-cardiac wave of the living body, and (b) an impedance pulse wave detector for detecting an impedance pulse wave of the living body between a pair of electrodes fitted to predetermined positions of the living body with the heart interposed between them. There is also (c) a gate means for extracting a partial impedance pulse wave from the impedance pulse wave by taking in the impedance pulse wave for an intake period as determined based on a time of detection of a predetermined part of the induced electro-cardiac wave by the electro-cardiac wave detection device. In addition there is (d) a preejection period computing means for computing the preejection period as a time difference between a time a predetermined part in the induced electro-cardiac wave detected by the electro-cardiac wave detection device periodically appears and a time a predetermined part in the partial impedance pulse wave extracted by the gate means periodically appears.

Advantages of the Seventh Aspect of the Invention

With the above described arrangement, the partial impedance pulse wave is extracted by the gate means from the impedance pulse wave detected by the impedance pulse wave detector by taking in the impedance pulse wave for the intake period as determined based on the time of detection of the predetermined part of the induced electro-cardiac wave. The preejection period computing means computes the preejection period as the time difference between the time the predetermined part in the induced electro-cardiac wave detected by the electro-cardiac wave detection device periodically appears and the time the predetermined part in the partial impedance pulse wave extracted by the gate means periodically appears. In other words, the preejection period is computed by using as a terminating point a periodically appearing predetermined part of the impedance pulse wave that is relatively free from noise, and therefore accurate. According to the seventh aspect of the invention, since a microphone for detection the cardiac operation of beating out blood is not used, the preejection period can be measured accurately if the heart sound contains noises.

Other Modes of Carrying out the Invention in the Sixth and Seventh Aspects

Preferably, the preejection period measuring apparatus further includes a cardiac function assessing means for assessing a cardiac function of the living body based on the preejection period computed by the preejection period computing means. With this arrangement, the cardiac function can be assessed accurately when compared with the assessment of the cardiac function conducted based on the preejection period determined by using a microphone.

Preferably, the intake period of the gate means of the preejection period measuring apparatus is from the end of a predetermined first time period starting from the time of detection of the predetermined part of the induced electro-cardiac wave by the electro-cardiac wave detection device to the end of a predetermined second time period starting from the time of detection of the predetermined part. The second time period is longer than the first time period. With this arrangement, the intake period is determined only based on a part of the induced electro-cardiac wave that is less affected by noise so that the intake period can be determined accurately, and it is no longer necessary to obtain any additional information for determining the intake period.

BRIEF DESCRIPTION OF THE DRAWINGS

FIG. 34 is a flow chart of an operation of an electronic control device of the embodiment of the blood pressure measuring apparatus of FIG. 33, illustrating the operation of computing the preejection period.

DESCRIPTION OF THE PREFERRED EMBODIMENTS

Figure 1:
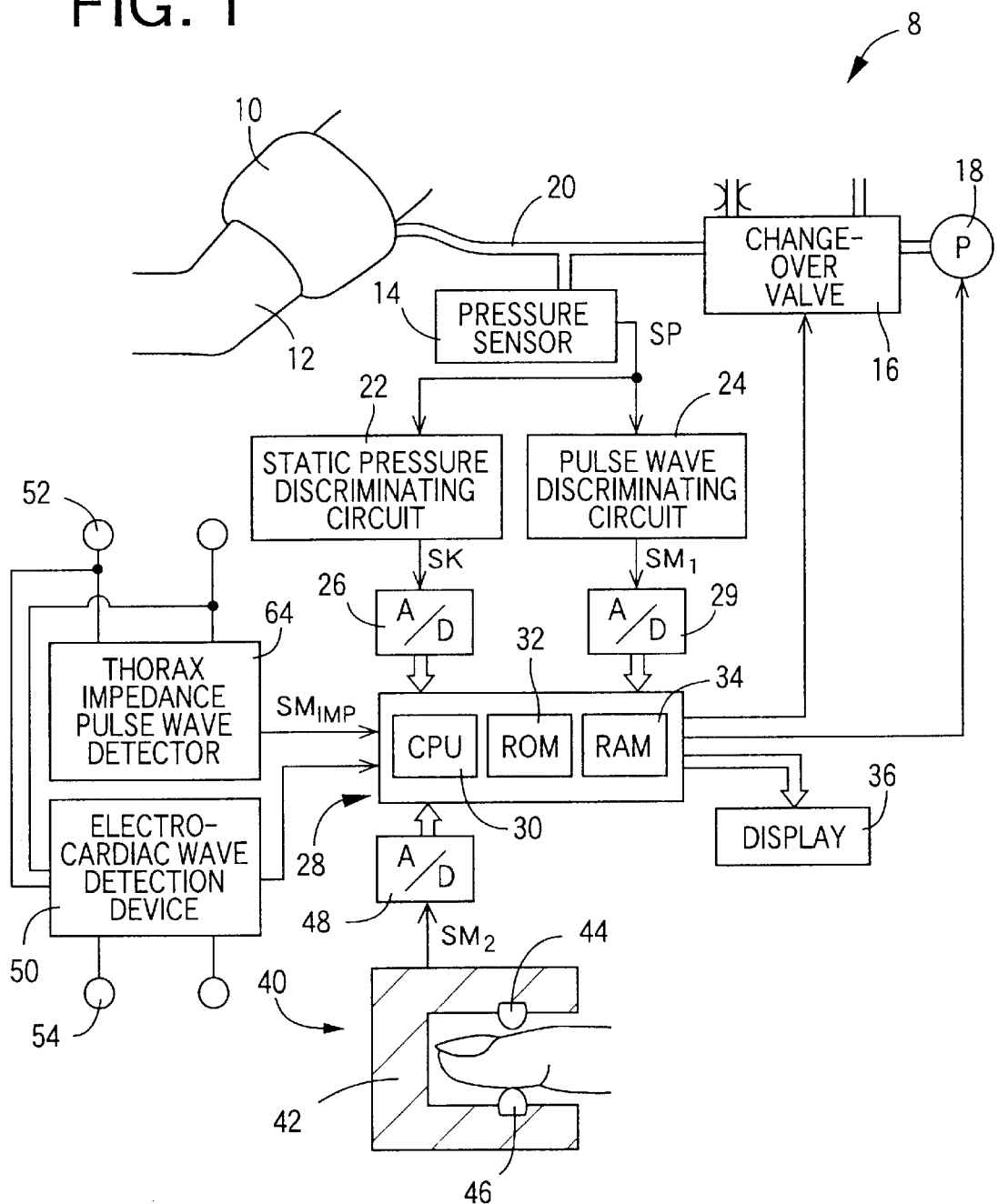
FIG. 1 is a block diagram of an embodiment of a blood pressure monitoring apparatus according to the invention.

Now, the present invention will be described by referring to the accompanying drawings that illustrate preferred embodiments of the invention. FIG. 1 is a schematic block diagram of a blood pressure monitoring apparatus 8 provided with a heartbeat synchronous information acquiring apparatus according to the invention.

Referring to FIG. 1, the blood pressure monitoring apparatus 8 is composed of a cuff 10 to be wound around an upper arm 12 of a subject, a pressure sensor 14, a changeover valve 16 and an air pump 18. The pressure sensor 14, the changeover valve 16 and the air pump 18 are connected to the cuff 10 by way of piping 20. The changeover valve 16 is adapted to select a pressure application mode for allowing pressure to be applied to the inside of the cuff 10, a slow depressurizing mode for slowly depressurizing the inside of the cuff 10, and a quick depressurizing mode for quickly depressurizing the inside of the cuff 10.

The pressure sensor 14 is adapted to detect the internal pressure of the cuff 10 and supply a pressure signal SP representing the detected pressure to a static pressure discriminating circuit 22 and a plurality of pulse wave discriminating circuits 24. The static pressure discriminating circuit 22 is provided with a low pass filter and adapted to discriminate a cuff pressure signal SK, representing a cuff pressure Pc which is a pressure constantly existing in the cuff and contained in the pressure signal SP, from the pressure signal SP and to transmit the cuff pressure signal SK to an electronic control device 28 by way of an A/D converter 26.

The pulse wave discriminating circuits 24 are provided with a band pass filter and adapted to discriminate a pulse wave signal $SM_1$, which is the oscillating component of the pressure signal SP in terms of frequency, from the pressure signal SP and to supply the pulse wave signal $SM_1$ to the electronic control device 28 by way of another A/D converter 29. A cuff pulse wave represented by the pulse wave signal $SM_1$ is a wave oscillating under pressure that is generated in an artery in the upper arm synchronously with the heartbeat of the subject and transmitted to the cuff 10. The cuff 10, the pressure sensor 14 and the pulse wave discriminating circuit 24 operate as a cuff pulse wave sensor.

The electronic control device 28 is in fact a microcomputer which is composed of a CPU 30, a ROM 32, a RAM 34 and an I/O port (not shown). The CPU 30 executes a program stored in advance in the ROM 32 for processing signals, utilizing a storage feature of the RAM 34, and outputs ejection signals from the I/O port to control the changeover valve 16. The CPU 30 also shows the operation on a display 36.

Referring also to FIG. 1, a photoelectric pulse wave sensor 40 also operates as a pulse wave detector for detecting a pulse wave propagating through the artery of the living body. It has a structure similar to the one used with a pulse meter and is typically adapted to be fitted to a fingertip. The photoelectric pulse wave sensor 40 includes a housing 42 that can accommodate part of a living body. A light emitting element 44 operating as a light source for irradiating rays of red light or infrared rays in a wavelength band that hemoglobin can reflect toward the epidermis of a living body and a photo detector 46 for detecting scattered light from the epidermis are arranged in the housing 42. The photoelectric pulse wave sensor 40 outputs a photoelectric pulse wave signal $SM_2$ and supplies it to the electronic control device 28. The photoelectric pulse wave signal $SM_2$ is a signal that pulsates once for each heartbeat, and corresponds to a volume of hemoglobin or blood in blood capillaries in the epidermis.

In FIG. 1, electro-cardiac wave detection device 50 is composed of a pair of electrodes 52 to be fitted to the thorax of the living body with the heart interposed between them, and is adapted to continuously detect an induced electro-cardiac wave, or obtain an electrocardiogram, showing an operating electric potential of the cardiac muscle of the living body. The induced electro-cardiac wave is detected, or an electrocardiogram is obtained, by way of a plurality of electrodes made to adhere to predetermined positions of the living body, and an electro-cardiac induction signal representing the detected electrocardiographally induced wave is supplied to the electronic control device 28 by way of an A/D converter (not shown).

Figure 2:
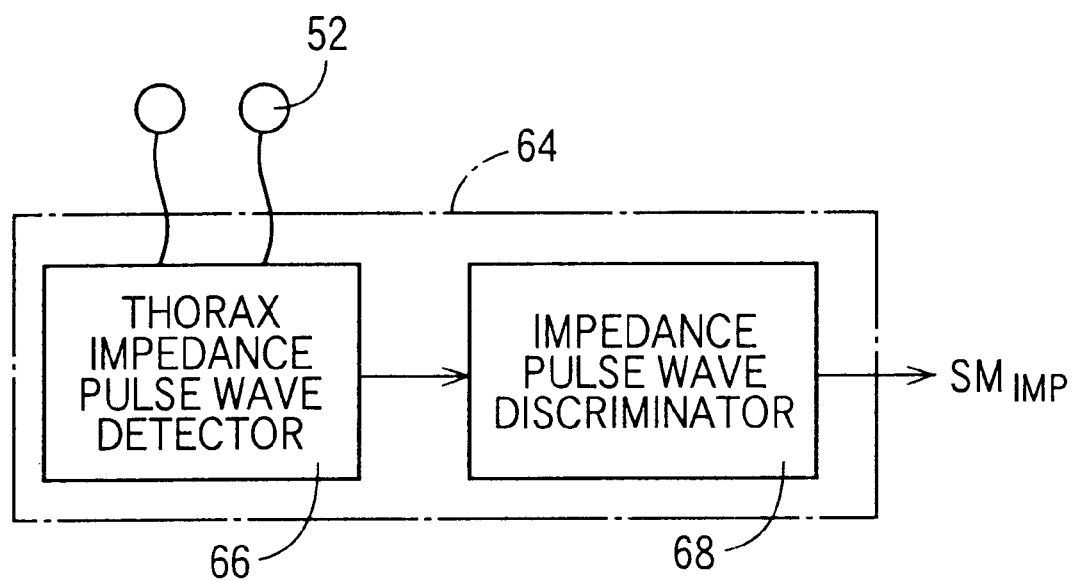
FIG. 2 is a block diagram of a thorax impedance pulse wave detector of FIG. 1.
Figure 4:
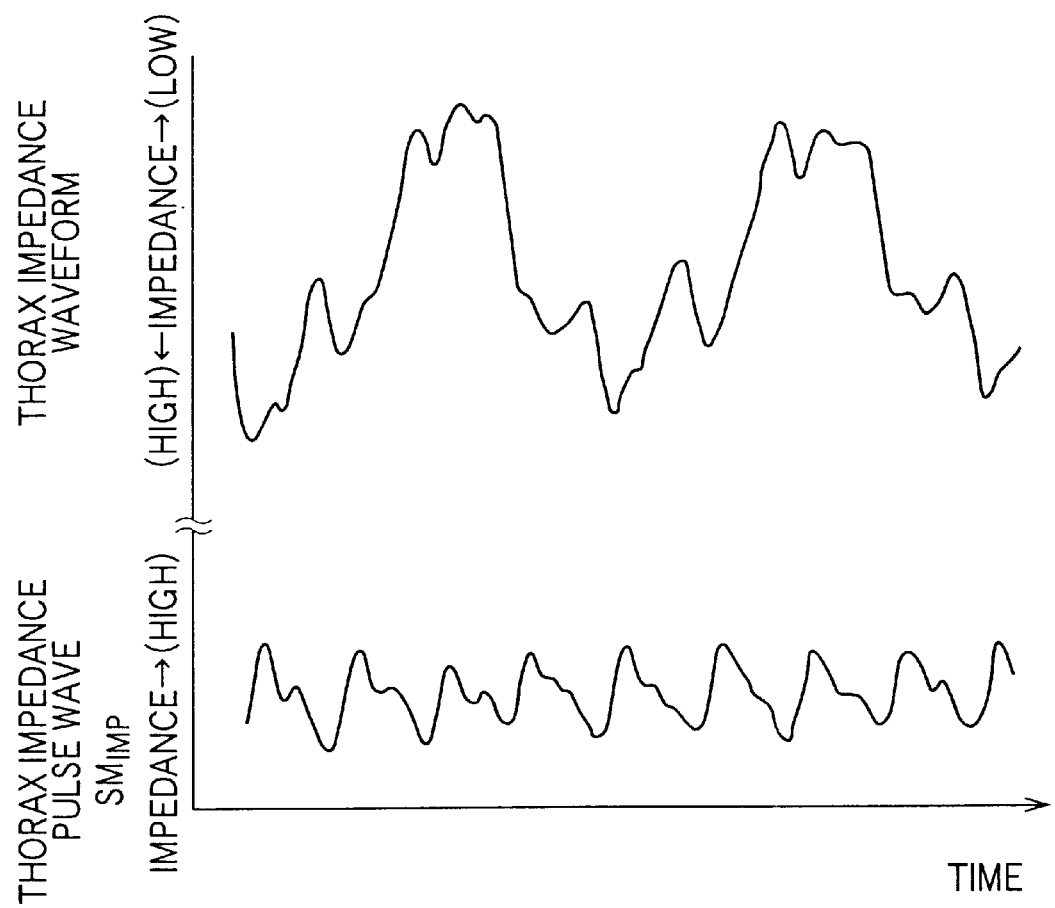
FIG. 4 is a graph showing a thorax impedance pulse wave detected by the thorax impedance pulse wave detector of FIG. 1 in comparison with a waveform of the thorax impedance.

In FIG. 1, a thorax impedance pulse wave detector 64 includes a pair of electrodes to be fitted to the epidermis of the thorax of the living body at positions with the heart interposed between them, and typically has a configuration as shown in FIG. 2. Referring to FIG. 2, the thorax impedance pulse wave detector 64 is composed of a pair of electrodes 52 to be fitted to the thorax of the living body that are adapted to also operate as the electrodes of an electrocardiograph, a thorax impedance detector 66 for detecting an impedance in the thorax, by way of the pair of electrodes 52, and outputting a signal representing the waveform of the thorax impedance as shown in the upper half of FIG. 6. There is also an impedance pulse wave discriminator 68 provided with a band pass filter for a band between about 0.5 and 30 Hz and adapted to discriminate a thorax impedance pulse wave signal $SM_{IMP}$ from the heartbeat synchronous signal, or the heartbeat. The impedance pulse wave signal $SM_{IMP}$ has a base wave with a frequency the same as that of the heartbeat synchronous signal, or the heartbeat, and is contained in the signal output from the thorax impedance detector 66. The thorax impedance pulse wave detector 64 outputs the signal $SM_{IMP}$ representing the thorax impedance pulse wave as shown in the lower half of FIG. 4. Note that the signal representing the thorax impedance waveform as shown in the upper half of FIG. 6 contains a respiration synchronous signal that corresponds to the changes in a volume of air in the thorax, and the thorax impedance pulse wave signal $SM_{IMP}$ that is the heartbeat synchronous signal corresponding to the changes in a volume of blood in the heart. Also note that the vertical axis in the upper half of FIG. 4 represents an impedance that is low when located at a high position, whereas the vertical axis in the lower half of FIG. 4 represents an impedance that is high when located at a high position. In other words, a rising edge of the thorax impedance pulse wave $SM_{IMP}$ in the lower half of FIG. 4 indicates the start of a contraction of the heart (left ventricle).

Figure 3:
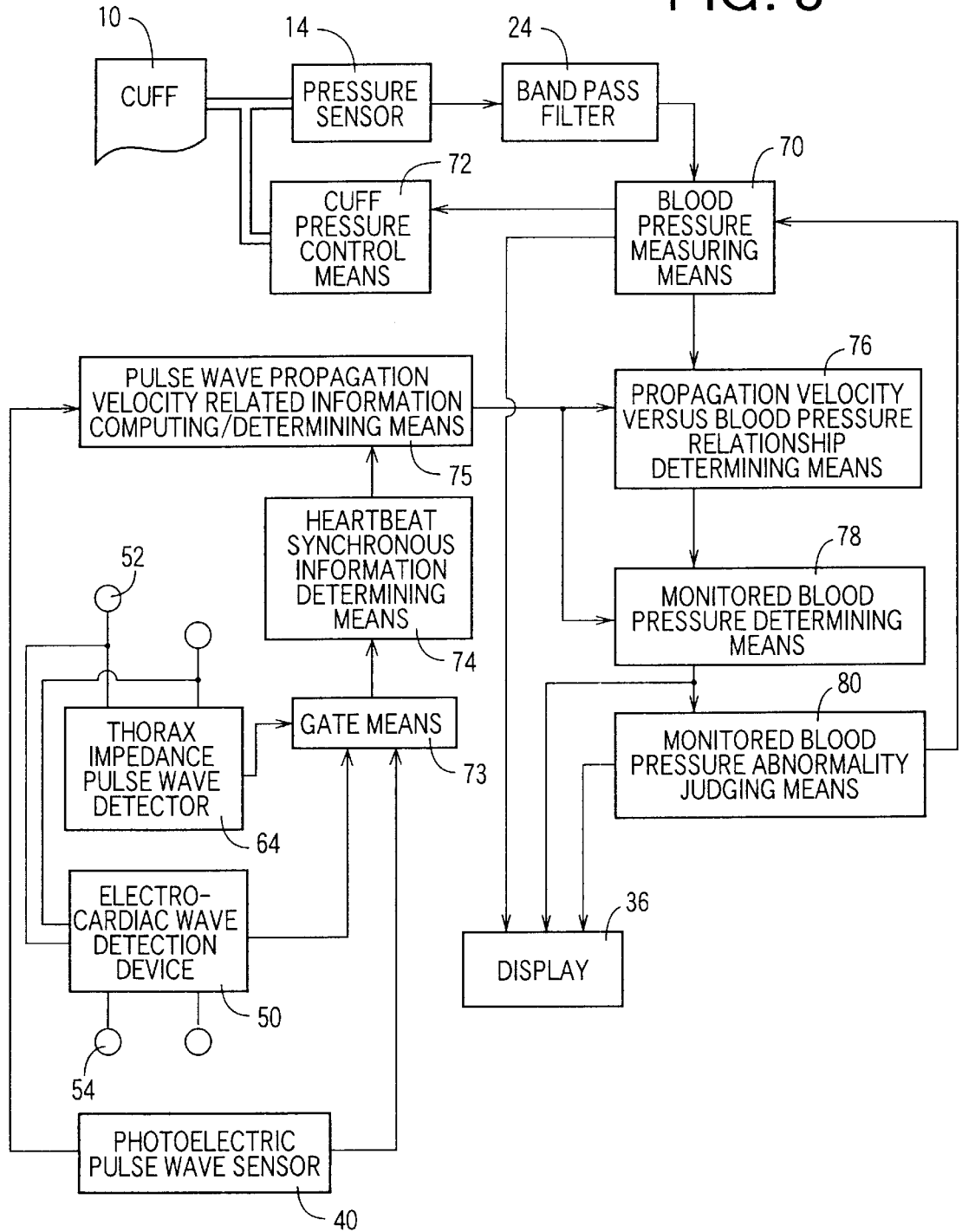
FIG. 3 is a block diagram of an electronic control device of the embodiment of FIG. 1, illustrating the control function thereof.
Figure 7:
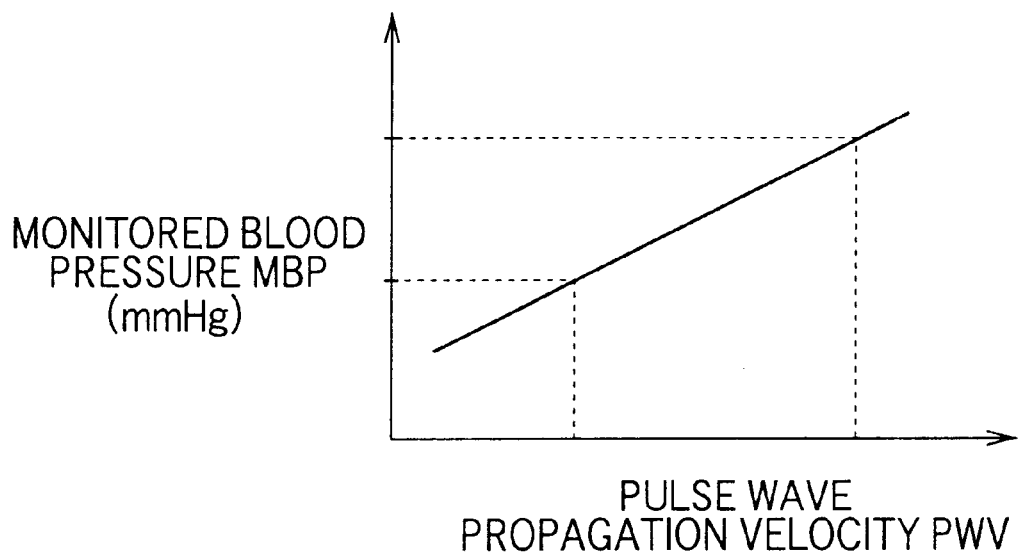
FIG. 7 is a graph of a propagation velocity versus blood pressure relationship that can be used for monitoring the blood pressure in the embodiment of FIG. 1.

FIG. 3 is a schematic block diagram illustrating the functional features of a principal part of the electronic control device 28 of the blood pressure monitoring apparatus 8. Referring to FIG. 3, a cuff pressure control means 72 changes the pressure of the cuff 10 according to a well known measuring procedure during a measuring period of the blood pressure measuring means 70 that is triggered to cyclically operate within a predetermined period for the purpose of the calibration of the propagation velocity versus blood pressure relationship as shown in FIG. 7. For instance, the cuff pressure control means 72 may raise the pressure of the cuff 10 to a high target level selected to be equal to about 180 mmHg that is higher than the highest blood pressure of the living body, and then gradually lower the pressure at a rate of about 3 mmHg/sec during the measuring period when a blood pressure measuring algorithm is executed. When an operation of measuring the blood pressure is over, the cuff pressure control means 72 completely releases the internal pressure of the cuff 10.

The blood pressure measuring means 70 measures the highest blood pressure $BP_{ISYS}$, the mean blood pressure $BP_{MEAN}$ and the lowest blood pressure $BP_{DIA}$ of the subject. This is done by means of the well known oscillo-metric method based on the changes in the pulse wave obtained as a wave oscillates under pressure during the gradual change in the internal pressure of the cuff 10. The pressure results are shown on the display 36.

Figure 5:
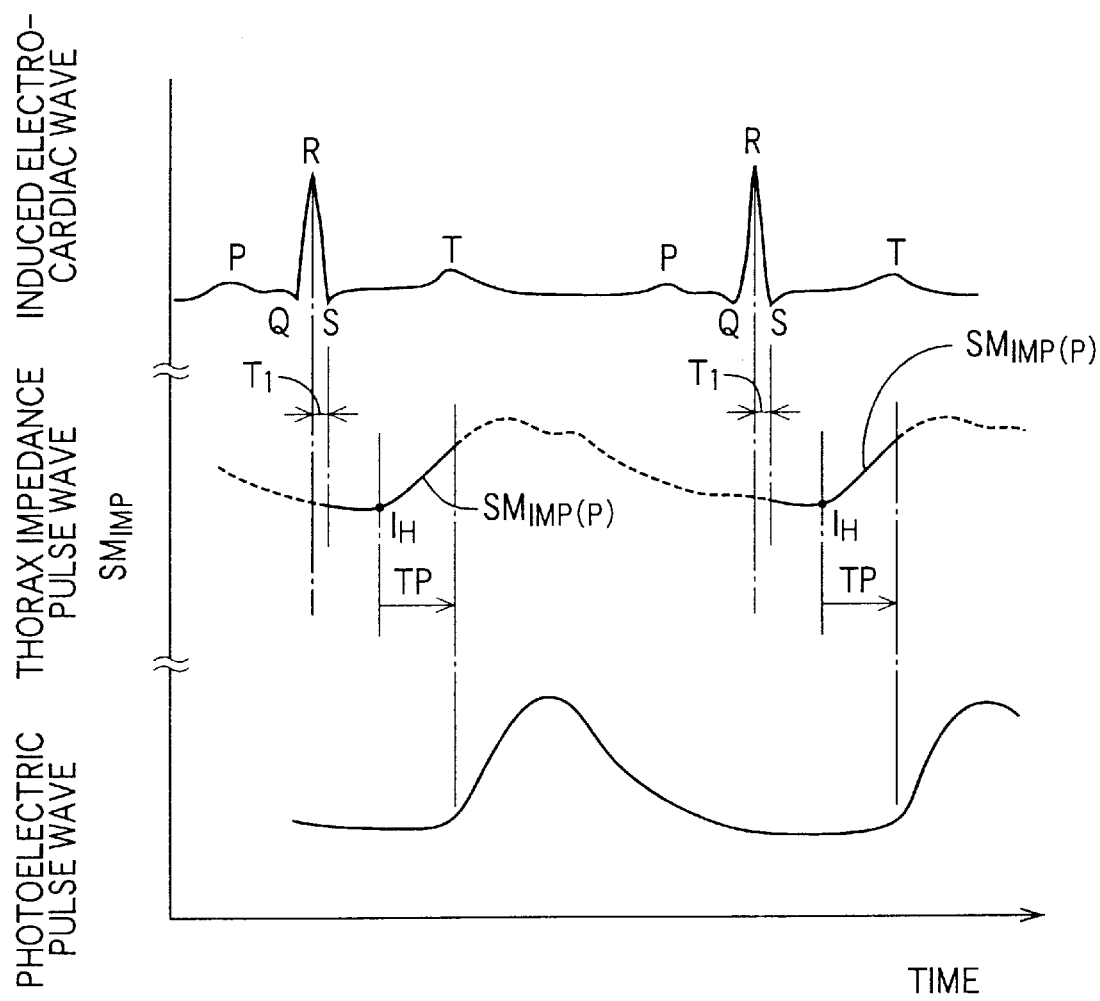
FIG. 5 is a timing chart illustrating a partial impedance pulse wave $SM_{IMP(P)}$ taken in under the control of the electronic control device of the embodiment of FIG. 1 and a propagation time TP determined by the electronic control device.

The gate means 73 takes in the thorax impedance pulse wave $SM_{IMP}$ that is continuously detected by the thorax impedance pulse wave detector 64 in each intake period, and extracts a partial impedance pulse $SM_{IMP(P)}$ of that period from the thorax impedance pulse wave $SM_{IMP}$ it takes in. Each intake period is defined as a period starting from a first time $T_1$ after the time when a predetermined part, for example an R wave, of the induced electro-cardiac wave is detected by the electro-cardiac wave detection device 50 to a time when a predetermined part, for example a rising edge or a peak, of the photoelectric pulse wave $SM_2$ is detected by the photoelectric pulse wave sensor. The first time $T_1$ is determined based on one or more than one test conducted in advance so as to make it shorter than a period from the time when the predetermined part of the photoelectric pulse wave appears to a time when the predetermined part of the impedance pulse wave $SM_{IMP}$, to be used as heartbeat synchronous information, appears. For instance, if the appearance of the R wave in the induced electro-cardiac wave is selected as the starting point of the first time $T_1$ and a rising edge of the impedance pulse wave $SM_{IMP}$ is used as heartbeat synchronous information, the first time $T_1$ is about 50 (msec). If the photoelectric pulse wave sensor 40 is fitted to a finger tip, a rising edge of the photoelectric pulse wave $SM_{IMP}$ is delayed by about 300 (msec) from the time of the appearance of the R wave in the induced electro-cardiac wave so that the intake period of the thorax impedance pulse wave will be about 250 (msec). In FIG. 5, each part shown by a solid line in the graph of the thorax impedance pulse wave $SM_{IMP}$ indicates a partial impedance pulse wave $SM_{IMP(P)}$.

Referring back to FIG. 3, heartbeat synchronous information determining means 74 detects a predetermined part that periodically appears from the partial impedance pulse waves $SM_{IMP(P)}$ consecutively extracted by the gate means 73 and selects the predetermined part as heartbeat synchronous information $I_H$. For instance, it may select a rising edge of each partial impedance pulse wave $SM_{IMP(P)}$ M as heartbeat synchronous information $I_H$.

Figure 6:
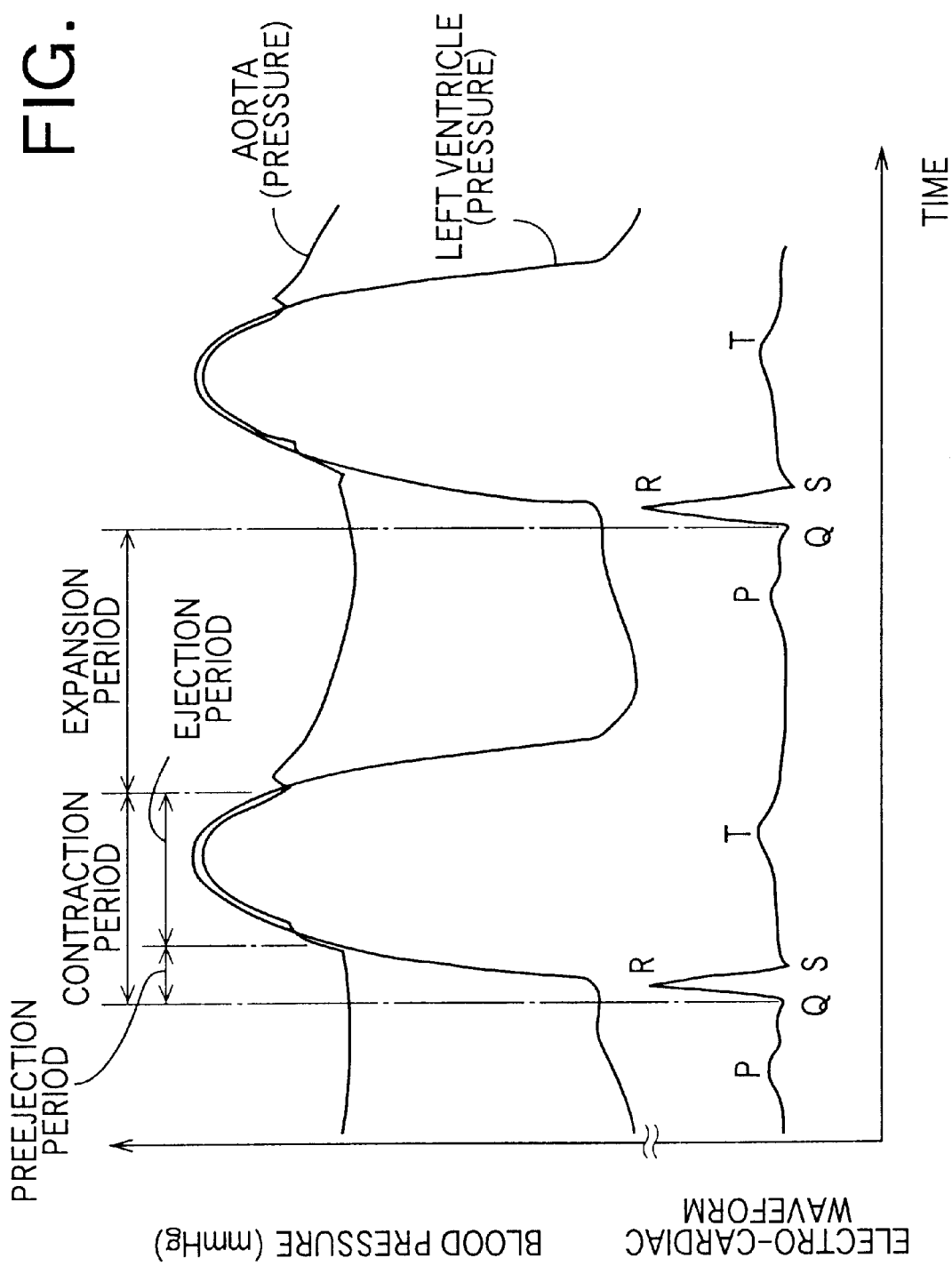
FIG. 6 is a graph illustrating the preejection period from a Q wave of an induced electro-cardiac wave to the time when the aortic valve is opened to eject out blood.

A pulse wave propagation velocity related information computing means 75 computes for each partial thorax impedance pulse wave a pulse wave propagation velocity PWV based on the heartbeat synchronous information $I_H$, selected by the heartbeat synchronous information determining means 74, and the pulse wave that is being propagated through the artery of the living body as detected by the photoelectric pulse wave sensor 40. The pulse wave propagation velocity related information computing means 75 includes a propagation velocity computing means for computing a propagation time TP (sec). The propagation time TP (sec) is the time difference between the heartbeat synchronous information $I_H$ corresponding to a time the predetermined part in the partial impedance pulse wave $SM_{IMP(P)}$ periodically appears, for example a rising edge, and a time the predetermined part in the photoelectric pulse wave $SM_2$ periodically appears, for example a rising edge. More specifically, the pulse wave propagation velocity related information computing means 75 computes a plurality of propagation velocity values PWV (m/sec) based on the propagation time TP computed by the propagation time computing means, using a preselected formula 1 below. In the formula 1, $L_1$ is a distance of propagation from the heart to the bodily position where the photoelectric pulse wave sensor 40 is fitted and which is specified in advance by testing. A rising edge of the partial impedance pulse wave $SM_{IMP(P)}$ indicates a time when the volume of blood in the left ventricle of the heart starts decreasing. In other words, it indicates the time when a preejection period PEP ends and a ejection period starts, as shown in FIG. 6. Therefore, the propagation time TP (sec) does not include the preejection period PEP and hence is not affected by an unstable cardiac muscle so that the pulse wave propagation velocity PWV can be determined accurately.

$$PWV = L_1/TP \quad (1)$$

Referring back to FIG. 3, propagation velocity related information versus blood pressure relationship determining means 76 determines the relationship between the blood pressure BP, measured by the blood pressure measuring means 70, and the pulse wave propagation velocity PWV or the propagation time TP computed by the pulse wave propagation velocity related information computing means 75. If, for example, the pulse wave propagation velocity PWV is used as pulse wave propagation velocity related information, the propagation velocity and the blood pressure will show a relationship as indicated by the graph in FIG. 7 and expressed by a formula $MBP = \alpha \cdot PWV + \beta$. In formula MBP $\alpha$ is a constant representing the gradient of the graph, $\beta$ is a constant representing the intercept and MBP is the monitored blood pressure. If the relationship of MBP=f (PWV) is determined from a pair of blood pressure values BP and the pulse wave propagation velocity PWV which is obtained when the blood pressure values BP are observed, the constants $\alpha$ and $\beta$ will represent respective general values that are statistically determined and vary depending on sex and age. However, if the relationship of MBP=f (PWV) is determined from the pulse wave propagation velocity PWV and two or more than two pairs of blood pressure values BP, the constants $\alpha$ and $\beta$ will be determined as values specific to the living body. The constants $\alpha$ and $\beta$ may be corrected each time the blood pressure is measured by the learning function of the blood pressure measuring means 70.

A monitored blood pressure determining means 78 continually determines the monitored blood pressure MBP from the propagation velocity versus blood pressure relationship MBP =f (PWV) or the propagation time versus blood pressure relationship MBP=f (TP) as determined by the propagation velocity related information versus blood pressure determining means 76 based on the actual pulse wave propagation velocity PWV or the actual propagation time TP computed by the pulse wave propagation velocity related information computing means 75. The monitored blood pressure determining means 78 then causes the display 36 to continuously show the blood pressure values MPB it has determined in order to show the trend. If the highest blood pressure $BP_{SYS}$ is used as the blood pressure value BP observed by the blood pressure measuring means 70 for the propagation velocity related information versus blood pressure relationship determining means 76 to determine the relationship MBP=f (PWV) or MBP=f (TP), the monitored blood pressure MBP refers to the highest blood pressure. Similarly, if the means blood pressure $BP_{MEAN}$ or the lowest blood pressure $BP_{DIA}$ is used, the monitored blood pressure MBP refers to the mean blood pressure or the lowest blood pressure, whichever is appropriate.

A monitored blood pressure abnormality judging means 80 compares the monitored blood pressure MBP as determined by the monitored blood pressure determining means 78 and a predetermined judgment reference range and determines that the monitored blood pressure is abnormal when it is found to be outside of the judgment reference range. Then, it causes the display 36 to show the abnormal condition of the blood pressure and starts driving the blood pressure measuring means 70 in order to re-determine the pulse wave propagation velocity related information versus blood pressure relationship. The above judgment reference range is used to detect if the blood pressure of the living body is abnormally high or low. If the monitored blood pressure MBP refers to the highest blood pressure, the judgment reference range will typically be between about 90 and 180 mmHg.

Figure 8:
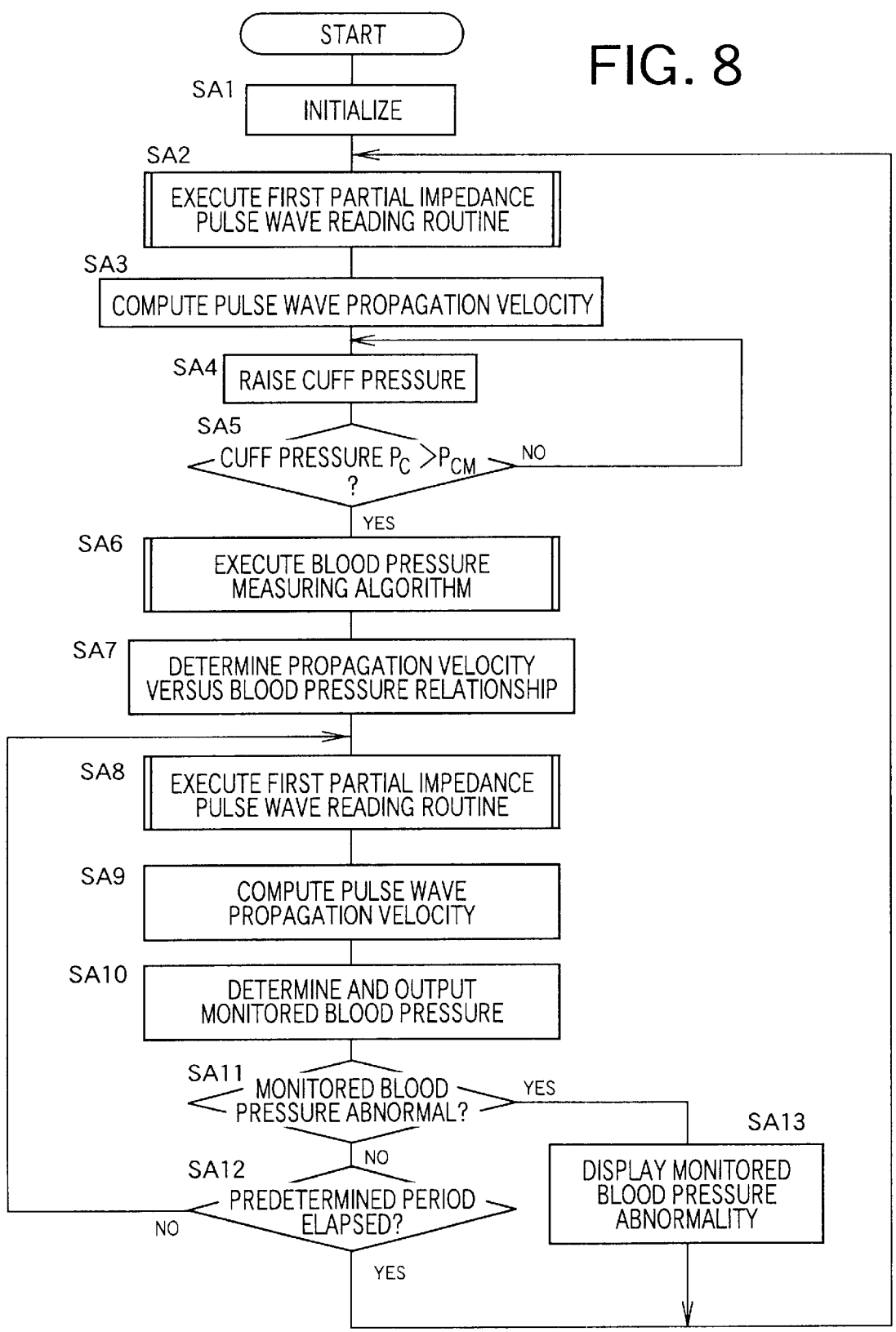
FIG. 8 is a flow chart of an operation of the electronic control device of the embodiment of FIG. 1.

FIG. 8 is a flow chart illustrating a control operation of the electronic control device 28. Note that, in this flow chart, the pulse wave propagation velocity PWV is used as pulse wave propagation velocity related information. In Step SA1 (the expression of Step will be omitted hereafter), an initial processing operation of clearing the counters and registers (not shown) is conducted. Then, in SA2, a first partial impedance pulse wave reading routine is executed. This routine will be described in greater detail by referring to FIG. 9 hereafter.

Figure 9:
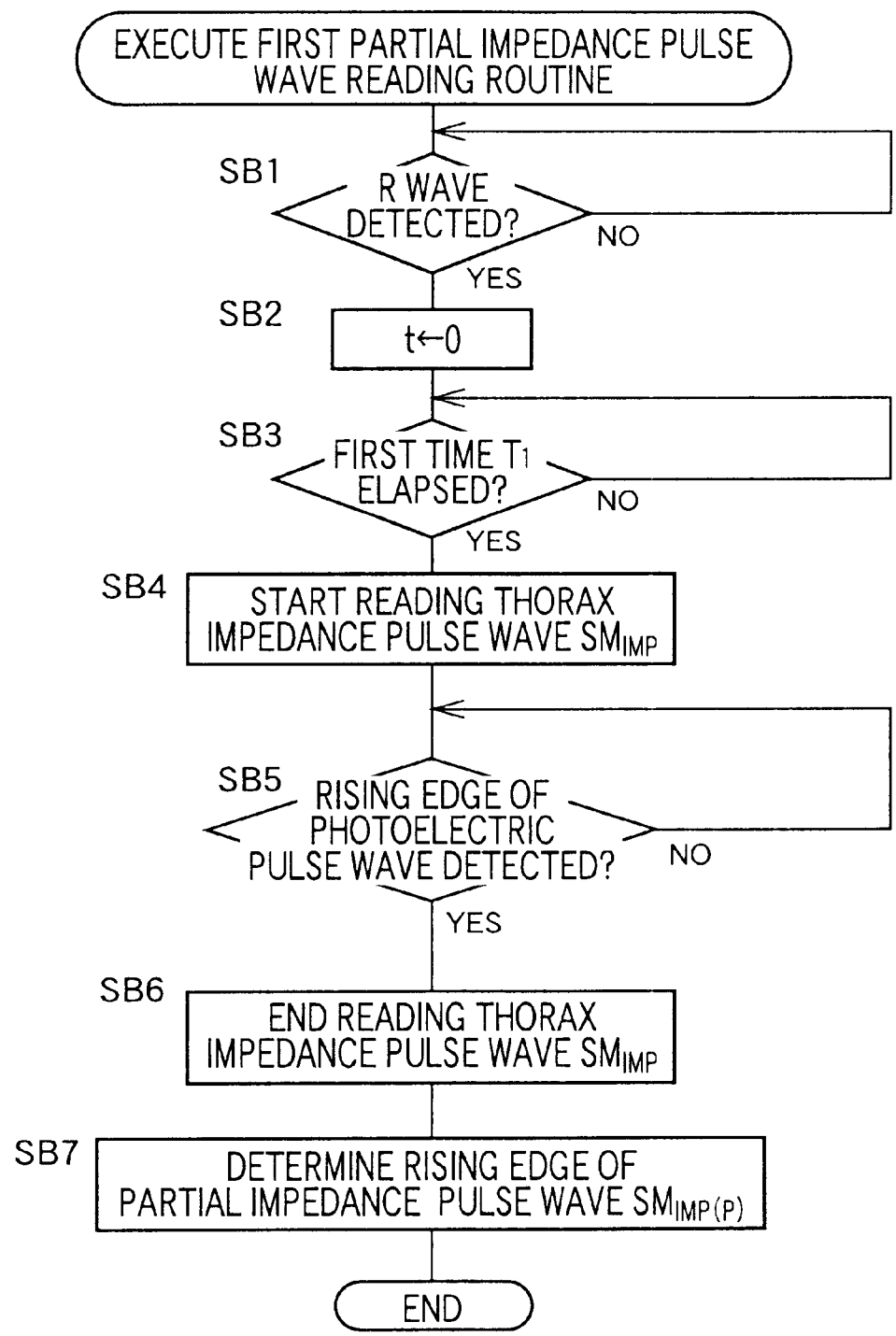
FIG. 9 is a flow chart of a first partial impedance pulse wave reading routine that is executed in SA2 and SA8 of the flow chart of FIG. 8.

Referring now to FIG. 9 which shows the first partial impedance pulse wave reading routine, firstly in SB1 it is determined whether the R wave of the induced electro-cardiac wave is detected or not. If it is determined that the R wave is not detected, the operation of SB1 is repeated. If, on the other hand, it is determined that the R wave is detected, timer t is set to "0" in the next step, or SB2.

In SB3, it is determined by the timer t whether the first time period $T_1$ that is defined to be equal to 50 msec in advance has elapsed or not. If it is determined that the first time period has not yet elapsed, the operation in SB3 is repeated and the device 28 is held in a standby state. If, on the other hand, it is determined by the timer t that the first time period has elapsed, the operation proceeds to SB4, where the operation of reading the thorax impedance pulse wave $SM_{IMP}$ starts.

Then, in SB5, it is determined whether a rising edge of the photoelectric pulse wave $SM_2$ is detected or not. If it is determined that a rising edge is not detected, the operation of SB5, or that of reading the thorax impedance pulse wave $SM_{IMP}$, is repeated. If, on the other hand, it is determined that a rising edge is detected, the device 28 proceeds to SB6, where the operation of reading the thorax impedance pulse wave $SM_{IMP}$ is terminated. It will be appreciated that SB1 through SB6 above correspond to an operation of the gate means 73 of this embodiment.

Subsequently, in SB7 that corresponds to the operation of the heartbeat synchronous information determining means 74, a rising edge of the partial impedance pulse wave $SM_{IMP(P)}$ that the gate means takes in during the period from the start of a reading operation in SB4 to the end of a reading operation in SB6 is selected as heartbeat synchronous information $I_H$.

Returning to FIG. 8, in SA3 that corresponds to the operation of the pulse wave-propagation velocity related information computing means 75, the time difference, or the propagation time TP (sec), between the time when the heartbeat synchronous information $I_H$ as determined in SB7 in FIG. 9 is produced and the time when a rising edge of the photoelectric pulse wave $SM_2$ is detected in SB5, is determined. Then the pulse wave propagation velocity PWV (m/sec) is computed, by using the formula 1 above and the obtained propagation time TP, immediately before a cuff pressure rise.

Then, in SA4 that corresponds to the operation of the cuff pressure control means 72, the changeover valve 16 is switched to the pressure application mode, and the air pump 18 is driven to operate to rapidly raise the internal pressure of the cuff 10 for the purpose of measuring the blood pressure.

Then, in SA5, it is determined whether the cuff pressure $P_c$ has risen above a preselected target pressure $P_{CM}$ that is equal to 180 mmHg or higher. If it is determined that the cuff pressure has not exceeded the target pressure, the operations of SB4 and SB5 are repeated to allow the cuff pressure $P_c$ to keep on rising. However, if it is determined that the cuff pressure has exceeded the target pressure in SA5 as a result of the rise of the cuff pressure $P_c$, a preselected blood pressure measuring algorithm that corresponds to the operation of the blood pressure measuring means 70 is executed in SA6. More specifically, the operation of the air pump 18 is stopped and the changeover valve 16 is switched to the slow depressurizing mode to gradually lower the internal pressure of the cuff 10 at a predetermined rate of about 3 mmHg/sec. As a result, the highest blood pressure $BP_{SYS}$, the mean blood pressure $BP_{MEAN}$ and the lowest blood pressure $BP_{DIA}$ of the subject are measured by means of the well known oscillo-metric method based on the changes in the pulse wave that are represented by the pulse wave signal $SM_1$ which is continuously obtained during the process of slowly lowering the blood pressure. At the same time, a frequency of the pulse is determined-based on the intervals separating consecutive pulses. Then, the obtained blood pressure and the frequency of the pulse are shown on the display 36 and the changeover valve 16 is switched to the rapid depressurizing mode to quickly reduced the internal pressure of the cuff 10.

Then, in SB7 that corresponds to the operation of the propagation velocity related information versus blood pressure relationship determining means 76, the relationship between the pulse wave propagation velocity PWV obtained in SA3 and the blood pressure $BP_{SYS}$, $BP_{MEAN}$ or $BP_{DIA}$ obtained in SB6 by means of the cuff 10 is determined. More specifically, as the blood pressure values $BP_{SYS}$, $BP_{MEAN}$ and $BP_{DIA}$ are obtained in SA6, the relationship (MBP= $\alpha \cdot PWV + \beta$) between the pulse wave propagation velocity PWV and the monitored blood pressure MBP is determined based on one of the blood pressure values $BP_{SYS}$, $BP_{MEAN}$ or $BP_{DIA}$ and the pulse wave propagation velocity PWV.

After determining the propagation velocity versus blood pressure relationship in a manner as described above, the first partial impedance pulse wave reading routine is executed in SA8. Then, in SB9 corresponding to the operation of the pulse wave propagation velocity related information computing means 75, the pulse wave propagation velocity PWV is determined by using the newly obtained heartbeat synchronous information $I_H$ (a rising edge of the partial impedance pulse wave $SM_{IMP(P)}$) and a rising edge of the photoelectric pulse wave $SM_2$ based on the time difference between a periodic time of appearance of the heartbeat synchronous information $I_H$ and a periodic time when a rising edge of the photoelectric pulse wave $SM_2$ is detected as in SA3.

Then, in SB10 that corresponds to the operation of the monitored blood pressure determining means 78, the monitored blood pressure MBP is determined from the propagation velocity versus blood pressure relationship (MBP= $\alpha \cdot PWV + \beta$), as determined in SA7, based on the pulse wave propagation velocity PWV obtained in SDA9, and output to the display 36 to show the trend of monitored blood pressure values MBP corresponding to heartbeats.

Then, in SA11 that also corresponds to the operation of the monitored blood pressure determining means 78, it is determined whether the monitored blood pressure as obtained in SA10 exceeds the predetermined judgment reference range or not. If it is determined in SA11 that the monitored blood pressure does not exceed the judgment reference range, the operation of SA12 is executed. If, on the other hand, it is determined in SB11 that the monitored blood pressure does exceed the judgment reference range, the display 36 shows the abnormal blood pressure level in SA13. In other words, SA11 and SA13 correspond to the operation of the monitored blood pressure abnormality judging means 80. After SA13, the steps from SA2 are repeated to redefine the propagation velocity versus blood pressure relationship (MBP=$\alpha \cdot PWV + \beta$).

In SA12, it is determined whether a predetermined period of about 15 to 20 minutes that is the calibration period has elapsed since the measurement of the blood pressure by means of the cuff 10 in SA6 or not. If it is determined that the calibration time has not elapsed in SA12, the blood pressure monitoring routine from and including SA8 onwards is repeated and the monitored blood pressure value MBP is determined consecutively for each heartbeat. At the same time, the display 36 shows the trend of the monitored blood pressure values MBP against time. If, on the other hand, it is determined that the calibration time has elapsed in SA12, the cuff calibration routine from and including SA2 onwards is re-executed to redefine the relationship (MBP=α·PWV+β).

As described above, with this embodiment, the gate means 73 (SB1 through SB6) extracts the partial impedance pulse wave $SM_{IMP(P)}$ from the thorax impedance pulse wave $SM_{IMP}$ detected by the thorax impedance pulse wave detector 64. This is done over an intake period defined as a period starting from a first time $T_1$ after the time when the R wave of the induced electro-cardiac wave is detected to the time when a rising edge of the photoelectric pulse wave $SM_2$ is detected. Then, the heartbeat synchronous information determining means 74 (SB7) selects a rising edge of the partial impedance pulse wave $SM_{IMP(P)}$ that periodically appears as heartbeat synchronous information $I_H$. Thus, it is possible to accurately determine the heartbeat synchronous information $I_H$. Additionally, since the photoelectric pulse wave $SM_2$ that is detected by the photoelectric pulse wave sensor 40 is largely free of noise it is possible to accurately determine the end of the period for reading the thorax impedance pulse wave $SM_{IMP}$.

Furthermore, with this embodiment, as the blood pressure values $BP_{SYS}$, $BP_{MEAN}$ and $BP_{DIA}$ are obtained by the blood pressure measuring means 70 (SA6), the propagation velocity related information versus blood pressure relationship determining means 76 (SA6) determines the relationship (MBP=α·PWV+β) between the blood pressure $BP_{SYS}$, $BP_{MEAN}$ or $BP_{DIA}$ measured by the blood pressure measuring means 70 (SA6) and the pulse wave propagation velocity PWV computed by the pulse wave propagation velocity related information computing means 75 (SA5). Then, the monitored blood pressure determining means 78 (SA10) continually computes the monitored blood pressure values MBP from the propagation velocity versus blood pressure relationship as determined by the propagation velocity related information versus blood pressure relationship determining means 76 (SA6) This is done based on the actual pulse wave propagation velocity PWV computed by the pulse wave propagation velocity related information computing means 75 (SA3 or SA9) The pulse wave propagation velocity PWV determined by the pulse wave propagation velocity related information computing means 75 (SA3 or SA9) is accurate because it is computed based on the partial impedance pulse wave $SM_{IMP(P)}$ that is taken in for the intake period as determined based on the time when the R wave of the induced electro-cardiac wave is detected by the gate means 75 (SB1 through SB6). Thus, the monitored blood pressure values MBP that are consecutively determined by the monitored blood pressure determining means 78 (SA10) are based on the accurately computed pulse wave propagation velocity PWV and hence highly reliable.

Additionally, with this embodiment, when the monitored blood pressure abnormality judging means 80 (SA11, SA13) judges that the monitored blood pressure MBP is abnormal because it exceeds the judgment reference range, the blood pressure measuring means 70 (SA6) restarts the operation of measuring the blood pressure and the velocity related information versus blood pressure relationship determining means 76 (SA7) redefines the relationship between the pulse wave propagation velocity and the blood pressure (MBP=α·PWV+β). Thus, when the monitored blood pressure shows an abnormal value, the abnormal blood pressure is monitored automatically and highly reliably by means of the cuff. This in turn enhances the reliability of the subsequent operation of monitoring the blood pressure.

Moreover, with this embodiment, the display 36 shows the trend of the monitored blood pressure values MBP as determined consecutively by the blood pressure determining means 78 (SA10) so that the trend in the changes in the blood pressure can be easily recognized by the doctor enabling an accurate diagnosis.

Finally, with this embodiment, when the monitored blood pressure value MBP is judged to be abnormal by the monitored blood pressure abnormality judging means 80 (SA11, SA13) this is shown by the display 36. In this way the doctor is quickly made aware of the abnormal value of the monitored blood pressure MBP and therefore the condition of the living body or the blood pressure monitoring apparatus.

Now, another embodiment of the invention will be described. Note that, in the following description, the components which are the same as those of the preceding embodiment are denoted by the corresponding reference symbols, and will not be described any further.

Figure 10:
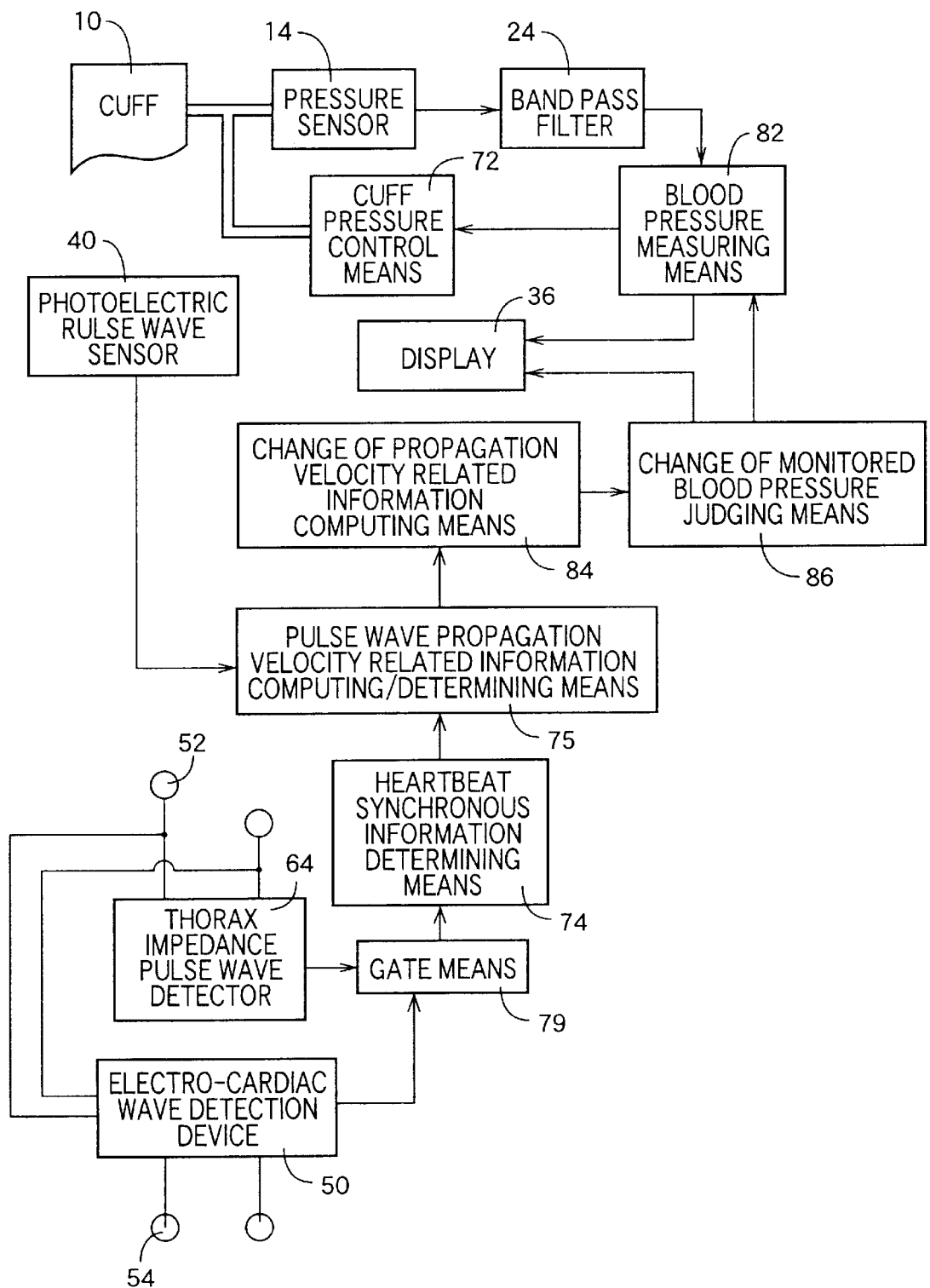
FIG. 10 is a block diagram of an electronic control device of another embodiment of the invention, illustrating the control function thereof.
Figure 11:
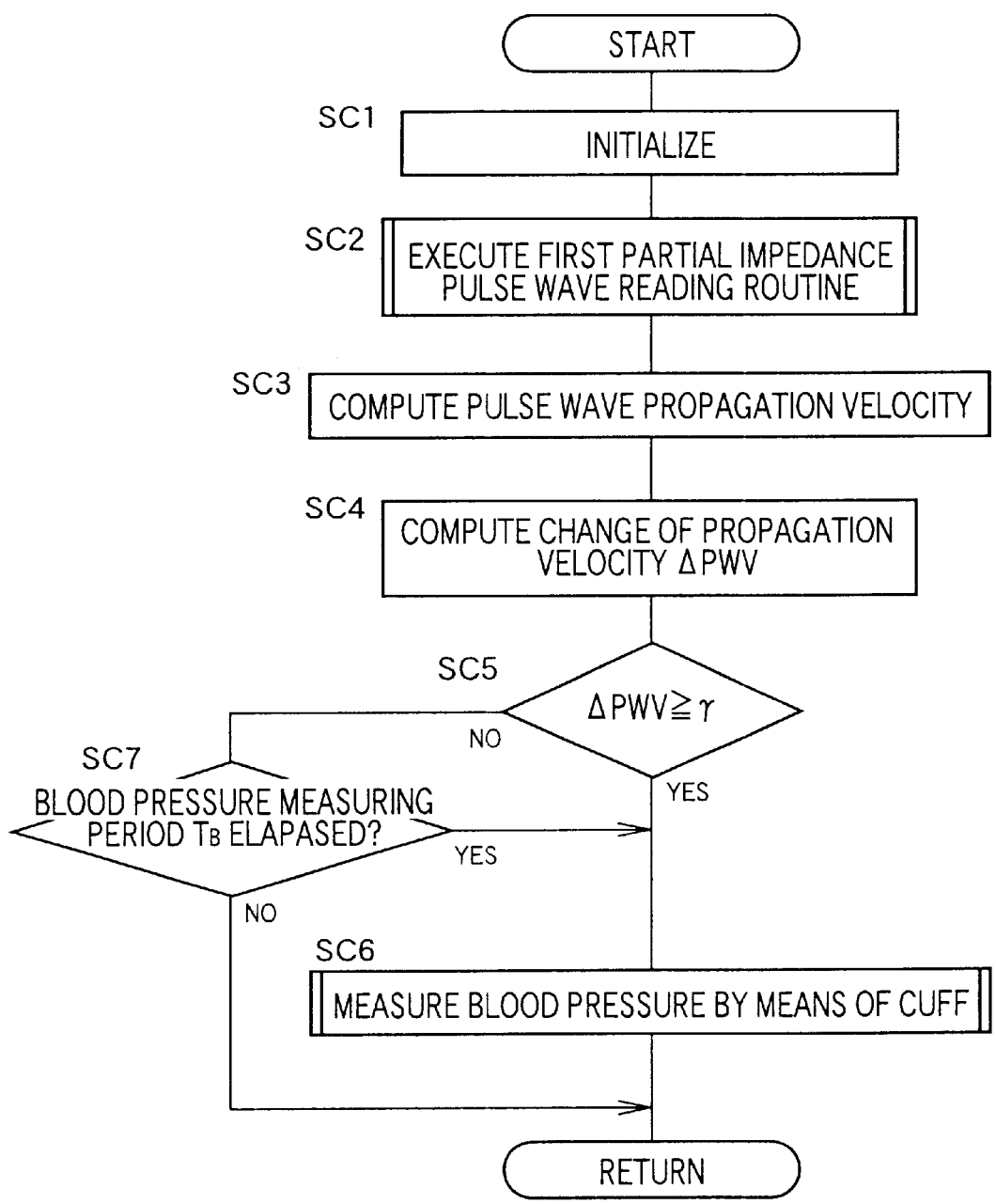
FIG. 11 is a flow chart of an operation of the electronic control device of the embodiment of FIG. 10.

FIGS. 10 and 11 are a schematic block diagram of this embodiment of the blood pressure monitoring apparatus according to the invention that corresponds to the third aspect of the invention and a flow chart of the operation of the embodiment respectively. While this embodiment of the blood pressure monitoring apparatus has mechanisms and a circuit configuration that are common to the first embodiment of FIG. 1, it differs from the second embodiment in terms of the method used by the electronic control device 28 to determine the intake period for taking in the thorax impedance pulse wave $SM_{IMP}$ and the method of monitoring the blood pressure. In this embodiment, the end of the intake period for taking in the thorax impedance pulse wave $SM_{IMP}$ is determined by the time elapsed since the predetermined part of the induced electro-cardiac wave is detected. While the blood pressure is measured periodically by means of the cuff 10 in each blood pressure measuring period $T_B$, fluctuations in the blood pressure are monitored by determining whether the change in the pulse wave propagation velocity PWV, or ΔPWV, exceeds a predetermined judgment reference value γ or not. Whenever the blood pressure is not measured and it is found that the change in the pulse wave propagation velocity, or ΔPWV, exceeds the predetermined judgment reference value γ, the cuff 10 is used to measure the blood pressure in order to update the monitored blood pressure value.

FIG. 10 is a schematic block diagram of the electronic control device 28 of this embodiment of the blood pressure monitoring apparatus. Referring to FIG. 10, a gate means 79 takes in the thorax impedance pulse wave $SM_{IMP}$ that is continuously detected by the thorax impedance pulse wave detector 64 in each intake period, and extracts the partial impedance pulse $SM_{IMP(P)}$ of that period out of the thorax impedance pulse wave $SM_{IMP}$ it takes in. Each intake period is defined as a period starting from the first time $T_1$ after the time when a predetermined part of the induced electro-cardiac wave, for example the R wave, is detected by the electro-cardiac wave detection device 50 to the time when the second time $T_2$ has elapsed since the time when the predetermined part of the induced electro-cardiac wave has been detected. The first time $T_1$ is determined as in the first embodiment and may typically be 50 (msec). On the other hand, while the second time $T_2$ is logically longer than the first time $T_1$, it is determined based on one or more tests conducted in advance so as to make it just long enough, for example 150 (msec), to contain the predetermined part of the thorax impedance pulse wave $SM_{IMP}$, for example a rising edge. The predetermined part of the thorax impedance pulse wave $SM_{IMP}$ is to be used for computing pulse wave propagation velocity related information. If the first time $T_1$ is 50 (msec) and the second time $T_2$ is 150 (msec), the intake period is 100 (msec).

A blood pressure measuring means 82 is triggered to operate in every blood pressure measuring period $T_B$, and measures the blood pressure using a well known method involving the use the cuff 10, like the blood pressure measuring means 70 of the first embodiment, to update the blood pressure value shown on the display 36. A change of propagation velocity related information computing means 84 computes the change $\Delta PWV$ (or $\Delta TP$) in the pulse wave propagation velocity PWV (or the propagation time TP) that is computed by the pulse wave propagation velocity related information computing means 75 for each heartbeat. It may be appreciated that the change $\Delta PWV$ (or $\Delta TP$) refers to the rate or amount of change relative to the mean value $PWV_{AV}$ or $TP_{AV}$ of the pulse wave propagation velocity values PWV (or the propagation time values TP), consecutively determined by the pulse wave propagation velocity related information computing means 75, or relative to the last pulse wave propagation velocity value PWV (or the propagation time value TP) obtained when the blood pressure is measured by the blood pressure measuring means 82.

A change of monitored blood pressure judging means 86 judges the change in the blood pressure of the living body based on whether the change $\Delta PWV$ (or $\Delta TP$) in the pulse wave propagation velocity related information as computed by the change of propagation velocity related information computing means 84 exceeds the predetermined reference value $\gamma$ or not. The change of monitored blood pressure judging means 86 then causes the display 36 to show the change in the blood pressure of the living body and at the same time, when necessary, triggers an operation of the blood pressure measuring means 82 to obtain the blood pressure value by using the cuff 10. In other words, the change of monitored blood pressure judging means 86 operates as means for starting a blood pressure measuring operation of the blood pressure measuring means 82 when the change $\Delta PWV$ (or $\Delta TP$) in the pulse wave propagation velocity related information exceeds the predetermined judgment reference value $\gamma$.

Figure 12:
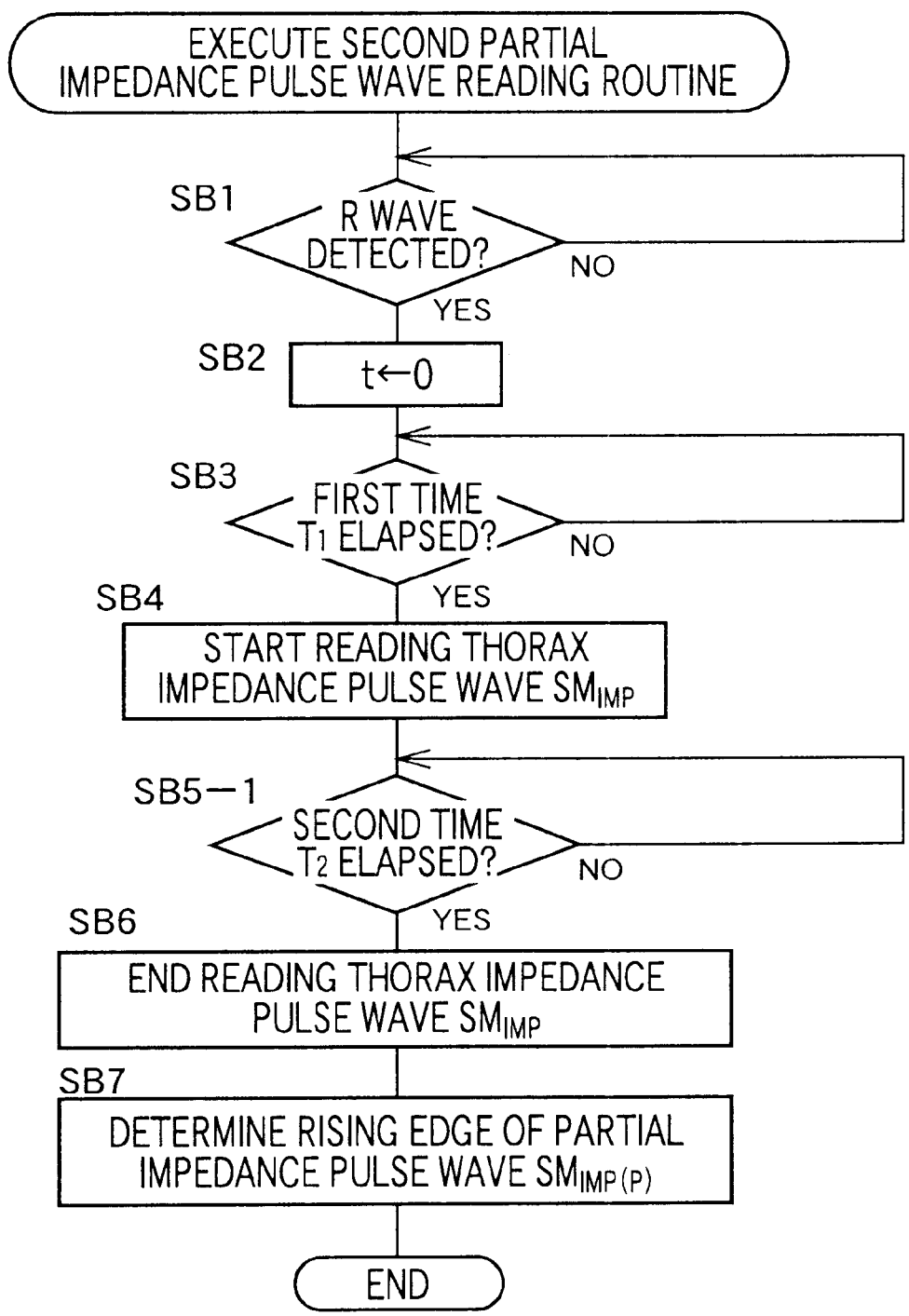
FIG. 12 is a flow chart of a second partial impedance pulse wave reading routine that is executed in SC2 of the flow chart of FIG. 11.

FIG. 11 is a flow chart of the control operation of the electronic control device 28 of this embodiment. Note that, in this flow chart again, the pulse wave propagation velocity PWV is used as pulse wave propagation velocity related information. Referring to FIG. 12, in Step SC1, an initial processing operation is conducted as in SA1 above. Then, in SC2, a second partial impedance pulse wave reading routine shown in FIG. 12 is executed.

The second partial impedance pulse wave reading routine of FIG. 12 is identical to the first partial impedance pulse wave reading routine of FIG. 9 except that SB5 is replaced by SB5-1. Now, SB5-1 will be discussed below.

In SB5-1, it is determined whether the reading of the timer t exceeds the second time $T_2$, which is set to be equal to 150 (msec), or not. In other words, it is determined whether the second time $T_2$ has elapsed since the time when the R wave is detected and the operation of reading the thorax impedance pulse wave $SM_{IMP}$ has started or not. If the second time $T_2$ has not elapsed, the operation of SB5-1 is repeated. If, on the other hand, the second time $T_2$ has elapsed, the control device 28 executes the subsequent SB6 and SB7 to complete the operation of reading the thorax impedance pulse wave $SM_{IMP}$, and selects a rising edge in the obtained partial impedance pulse wave $SM_{IMP(P)}$ as heartbeat synchronous information $I_H$.

Returning to FIG. 11, in SC3 that corresponds to the operation of the pulse wave propagation velocity related information computing means 75, the pulse wave propagation velocity PWV is computed as in SA9 of FIG. 8. Then, in SC4 that corresponds to the operation of the change of propagation velocity related information computing means 84, the change $\Delta PWV$ in the pulse wave propagation velocity PWV is computed. The change $\Delta PWV$ may be determined as an amount of change $(=PWV_i-PWV_{AV})$ or a rate of change $[=(PWV_i-PWV_{AV})/PWV_{AV}]$ relative to the mean value $PWV_{AV}$ $[=(PWV_{i-n}+\ldots+PWV_{i-1}+PWV_1)/(n+1)]$, or as the amount of change $(=PWV_i-PWV_m)$ or the rate of change $[=(PWV_i-PWV_m)/PWV_m]$ relative to a pulse wave propagation velocity $PWV_m$ obtained at the last blood pressure measuring operation using the cuff.

Then, in SC5 corresponding to the operation of the change of monitored blood pressure judging means 86, it is judged whether the change $\Delta PWV$ in the pulse wave propagation velocity PWV exceeds the predetermined judgment reference value $\gamma$ or not. The predetermined judgment reference value $\gamma$ is selected based on one or more tests conducted in advance so as to judge if the blood pressure of the subject has changed to such an extent that it particularly needs attention when monitoring the cardiac condition of the subject.

If the change $\Delta PWV$ in the pulse wave propagation velocity PWV exceeds a predetermined judgment reference value $\gamma$ (in SC5) it signifies that the blood pressure of the subject has changed significantly so that an operation of measuring the blood pressure of the subject, using the cuff, is started immediately. Also, a character or a symbol indicating a significant change in the monitored blood pressure and the value of the actual measured blood pressure, obtained by using the cuff 10 (in SC6), are shown on the display 36. If, on the other hand, the change $\Delta PWV$ in the pulse wave propagation velocity PWV does not exceed a predetermined judgment reference value $\gamma$ (in SC5), the judging operation in SC7 is carried out. In SC7, it is determined whether the pre-selected blood pressure measuring period $T_B$ has passed since the last measurement, using the cuff, in SC6 or not. The blood pressure measuring period $T_B$ is typically relatively long and may be between a little more than ten minutes and several tens of minutes.

If the pre-selected blood pressure measuring period $T_B$ has not passed since the last measurement (in SC7), the routine is suspended and the steps from SC1 and on are repeated. If, on the other hand, the pre-selected blood pressure measuring period $T_B$ has passed since the last measurement (in SC7) it means that it is time to measure the blood pressure in the current blood pressure measuring period. Therefore, in SC6 that corresponds to the operation of the blood pressure measuring means 82, the highest blood pressure value $BP_{SYS}$ and the lowest blood pressure value $BP_{DIA}$ are obtained and shown on the display 36 to complete the routine.

As described above, with this embodiment, the change of propagation velocity related information computing means 84 (SC4) computes the change $\Delta PWV$ in the pulse wave propagation velocity PWV that is computed by the pulse wave propagation velocity related information computing means 75 (SC3). Also, the change of monitored blood pressure judging means 86 (SC5) judges if the change $\Delta PWV$ in the pulse wave propagation velocity PWV, which is continually computed by the change of propagation velocity related information computing means 84 (SC4), exceeds the predetermined judgment reference value $\gamma$ or not. The pulse wave propagation velocity PWV computed by the pulse wave propagation velocity related information computing means 75 (SC3) is accurate because it is determined based on the partial impedance pulse wave $MP_{IMP(P)}$ that is taken in by the gate means 79 (SB1 through SB6) for 100 (msec) which is determined based on the time when the R wave of the induced electro-cardiac wave is detected. Thus, the judgment on the change in the blood pressure made by the change of monitored blood pressure judging means 86 (SC5) is reliable because it is based on the change ΔPWV in the pulse wave propagation velocity PWV which is accurate. Additionally, with this embodiment, the change of monitored blood pressure judging means 86 (SC5) causes the blood pressure measuring means 82 (SC6) to start to operate depending on its judgment on the change in the blood pressure of the living body. More specifically, when the change of monitored blood pressure judging means 86 (SC5) judges that the change in the blood pressure of the living body is abnormal, the blood pressure measuring means 82 (SC6) immediately measures the blood pressure by means of the cuff. In other words, the blood pressure is measured automatically and highly reliably, by means of the cuff, whenever it is judged that the change in the blood pressure is abnormal.

Finally, with this embodiment, the intake period of the gate means 79 (SB1 through SB6) is determined solely based on the induced electro-cardiac wave that is minimally affected by noise. In other words, the intake period can be determined accurately and reliably as well as any other information required to determine the intake period.

Figure 13:
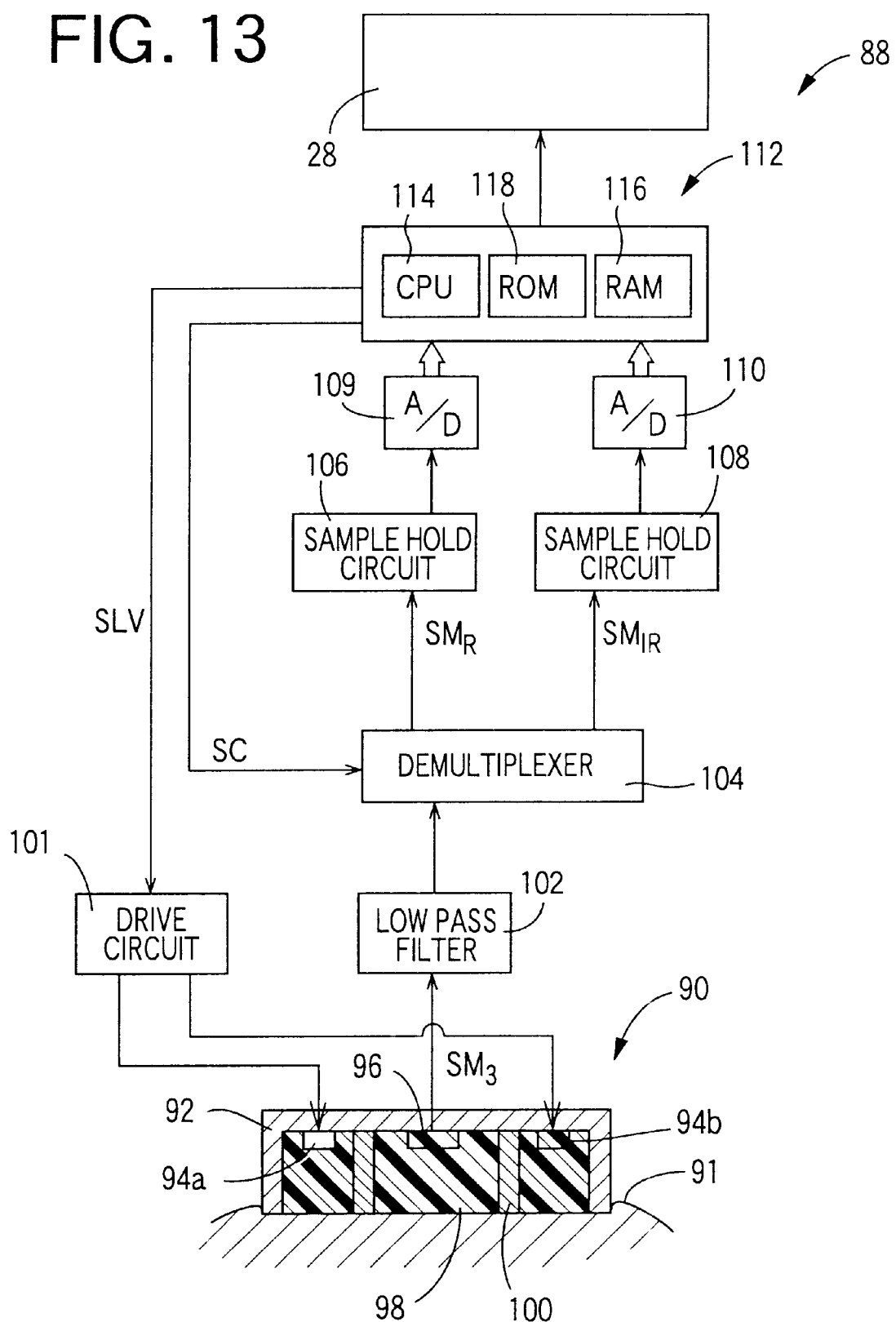
FIG. 13 is a schematic block diagram of a blood pressure monitoring apparatus using a photoelectric pulse wave detection probe provided in a pulse oximeter for measuring the oxygen saturation level in blood.

FIG. 13 schematically illustrates the blood pressure monitoring apparatus that includes a pulse oximeter 88, for observing an oxygen saturation level in the blood, which in turn includes a photoelectric pulse wave detection probe 90 which is used as photoelectric pulse wave sensor (to be referred to simply as probe hereafter). The probe 90 is tightly fitted to a body surface 91 of the subject, typically at the forehead, by means of a holder belt (not shown). The probe 90 is composed of a cup-shaped housing 92 that opens at a side, light emitting elements including a first light emitting element 94a and a second light emitting element 94b (to be referred to indiscriminately as light emitting elements 94 hereafter, whenever it is not necessary to discriminate between them) that are typically LEDs arranged near the outer periphery on the inner surface of the bottom of the housing 92. There is also a light receiving element that is typically a photodiode or a photo transistor, a transparent resin 96 provided integrally in the housing 92 to cover the light emitting elements 94 and the light receiving element 96, and an annular shield member 100 arranged between the light emitting elements 94 and the light receiving element 96 in the housing 92. The annular shield member 100 is for the purpose of blocking beams of light emitted from the light emitting elements 94, which irradiate the body surface 91, and those reflected by the body surface 91, which are directed toward the light receiving element 96.

The first light emitting element 94a emits rays of red light with a wavelength of about 660 nm, whereas the second light emitting element 94b emits infrared rays with a wavelength of about 800 nm. The first light emitting element 94a and the second light emitting element 94b alternately emit rays of light as they are driven alternately by the drive current from drive circuit 101. Rays of light emitted from the light emitting elements 94a and 94b, which irradiate the body surface 91 and then are reflected by an area of the body surface 91 where the blood capillaries are concentrated in the body, are also received by the common light receiving element 96.

The light receiving element 96 outputs a photoelectric pulse wave signal $SM_2$, the magnitude of which reflects the quantity of received light, by way of a low pass filter 102. An amplifier may be arranged between the light receiving element 96 and the low pass filter 102 if appropriate. The low pass filter 102 eliminates any noise because it has a frequency higher than the frequency of the pulse wave of an input photoelectric pulse wave signal $SM_3$ and outputs the signal $SM_3$ that is cleared of noise to a demultiplexer 104. The demultiplexer 104 alternately supplies an electric signal $SM_R$ generated by red light to an I/O port (not shown) of an electronic control device 112 by way of a sample hold circuit 106 and an A/D converter 109, and an electric signal $SM_{IR}$ generated by infrared rays to the I/O port by way of a sample hold circuit 108 and an A/D converter 110. This is done by switching $SM_R$ and $SM_{IR}$ synchronously with the emission of light from the first light emitting element 94a and that of the second light emitting element 94b according to the signal from the electronic control device 112 for measuring the oxygen saturation level. The sample hold circuits 106 and 108 are used to temporarily hold the succeeding electric signals $SM_R$ and $SM_{IR}$ until the converting operations of the A/D converters 109 and 110 on the electric signals $SM_R$ and $SM_{IR}$. The converting operations commence when input electric signals $SM_R$ and $SM_{IR}$ are output sequentially to the A/D converters 109 and 110. Note that the electronic control device 112 is connected to the display for showing the oxygen saturation level in the blood.

The electronic control device 112 is a microcomputer which is composed of a CPU 114, a RAM 116 and a ROM 118, and adapted to communicate with the electronic control device 28. In the electronic control device 112, the CPU 114 executes the program stored in the ROM 118 for measuring the oxygen saturation level in the blood of the subject, utilizing the storage feature of the RAM 34, and causes the measured saturated oxygen level to be shown according to electric signals $SM_R$ and $SM_{IR}$. The CPU 114 also sequentially outputs the electric signals $SM_R$ and $SM_{IR}$ representing the photoelectric pulse wave, as shown in FIG. 5, to the electronic control device 28.

The method for computing the oxygen saturation level is described in Japanese Patent Laid-Open Publication No. Hei. 3-15440 whose applicant is the same as the applicant of the present patent application. More specifically, the oxygen saturation level is determined based on the actual ratio obtained based on a relationship between the ratio of $\{(V_{dR}-V_{SR})/(V_{dR}+V_{SR})\}\{(V_{dIR}-V_{SIR})/(V_{dIR}+V_{SIR})\}$ and the oxygen saturation level. In the above formula, $V_{dR}$ and $V_{SR}$ represent an upper peak value and a lower peak value respectively of the photoelectric pulse wave obtained by using rays of red light, and $V_{dIR}$ and $V_{SIR}$ represent an upper peak value and a lower peak value respectively of the photoelectric pulse wave obtained by using infrared rays. Also, $V_{dR}-V_{SR}$ and $V_{dIR}-V_{SIR}$ represent the amplitude of an AC component of the photoelectric pulse wave obtained by using rays of red light and the amplitude of an AC component of the photoelectric pulse wave obtained by using infrared rays respectively. Also, $V_{dR}+V_{SR}$ and $V_{dIR}+V_{SIR}$ represent twice the amplitude of the DC component of the photoelectric pulse wave obtained by using rays of red light and twice the amplitude of the DC component of the photoelectric pulse wave obtained by using infrared rays respectively.

As described above, in this embodiment, there is the pulse oximeter 88 that includes the photoelectric pulse wave detection probe 90. The probe 90 can also be used as the pulse wave detector so that the cost of the entire apparatus can be reduced in addition to the advantages of the preceding embodiments.

Figure 14:
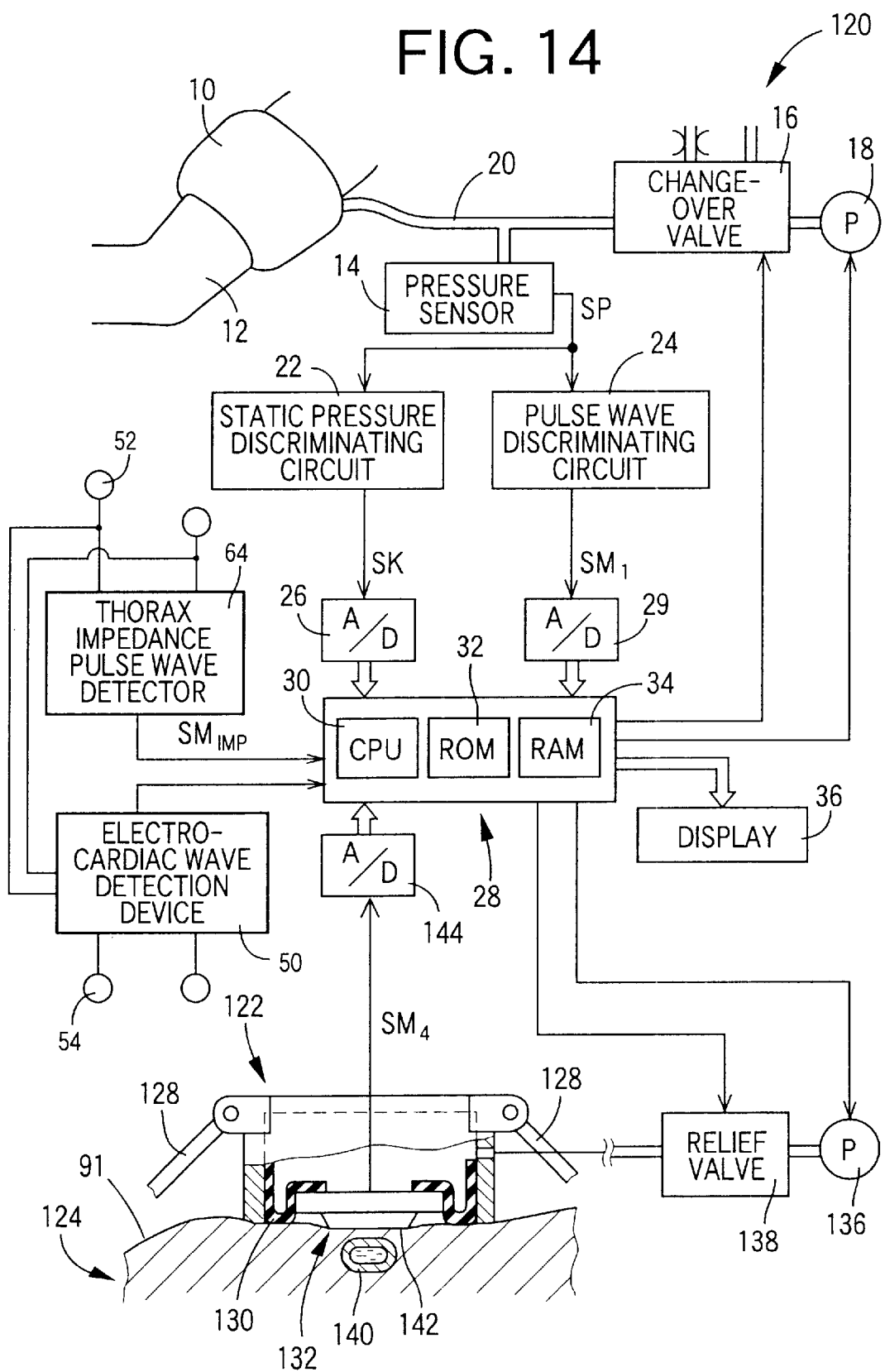
FIG. 14 is a block diagram of still another embodiment of the invention, which is a continuous blood pressure measuring apparatus provided with a pulse wave propagation velocity related information acquiring apparatus.

Now, still another embodiment of the invention will be described below. FIG. 14 is a schematic block diagram of a continuous blood pressure measuring apparatus 120 which includes the pulse wave propagation velocity related information acquiring apparatus as in the fourth aspect of the invention.

Referring to FIG. 14, a pressure pulse wave detection probe 122 is adapted so that it can be removably fitted to a wrist 124 of either the left arm or the right arm. The wave detection probe is preferably fitted at a position downstream from the artery of the upper arm 12, where the cuff 10 is not fitted, in such a way that the open end of a housing 126 operating as a container is disposed opposite the body surface 91. A pressure pulse wave sensor 132 is arranged in the housing 126 so that it is movable relative to the housing 126, and it is adapted to project through the open end of the housing 126 with a diaphragm 130 disposed between them. The housing 126 and the diaphragm 130 form a pressure chamber 134. It is arranged so that pressurized air can be supplied into the pressure chamber 134 from an air pump 136 by way of a relief valve 138. Thus, the pressure pulse wave sensor 132 is pressed against the body surface 91 under a pressure $P_{HD}$ that reflects an internal pressure of the pressure chamber 134. This is done until part of the wall of the blood vessel of a radial artery 140 becomes flattened by the pressing surface of the pressure pulse wave sensor 132.

The pressure pulse wave sensor 132 includes a large number of semiconductor pressure sensing elements (not shown) arranged on a pressing surface of the semiconductor chip which is typically made of a single silicon crystal. As the pressure pulse wave sensor 132 is pressed onto the radial artery 140 under the body surface 91 of the wrist 123, the pressure pulse wave generated by the radial artery 140 is transmitted to the body surface 91. Then, the pressure pulse wave sensor 132 detects the pressure pulse wave and supplies a pressure pulse wave signal $SM_4$, representing the detected pressure pulse wave, to the electronic control device 28 by way of an A/D converter 144. In this embodiment the pressure pulse wave sensor 132 operates as pulse wave detector.

The CPU 30 of the electronic control device 28 executes the program stored in advance in the ROM 32 to output a drive signal to the air pump 136 and the relief valve 138 to regulate the pressure in the pressure chamber 134, and hence the pressure under which the pressure pulse wave sensor 132 is pressed against the skin. As a result, when continuously monitoring the blood pressure, an optimal pressure $P_{HDP}$ of the pressure pulse wave sensor 132 is determined based on the pressure pulse wave continuously obtained in the process of changing the internal pressure of the pressure chamber 134. The relief valve 138 is controlled so as to maintain the optimal pressure $P_{HDP}$ of the pressure pulse wave sensor 132.

Figure 15:
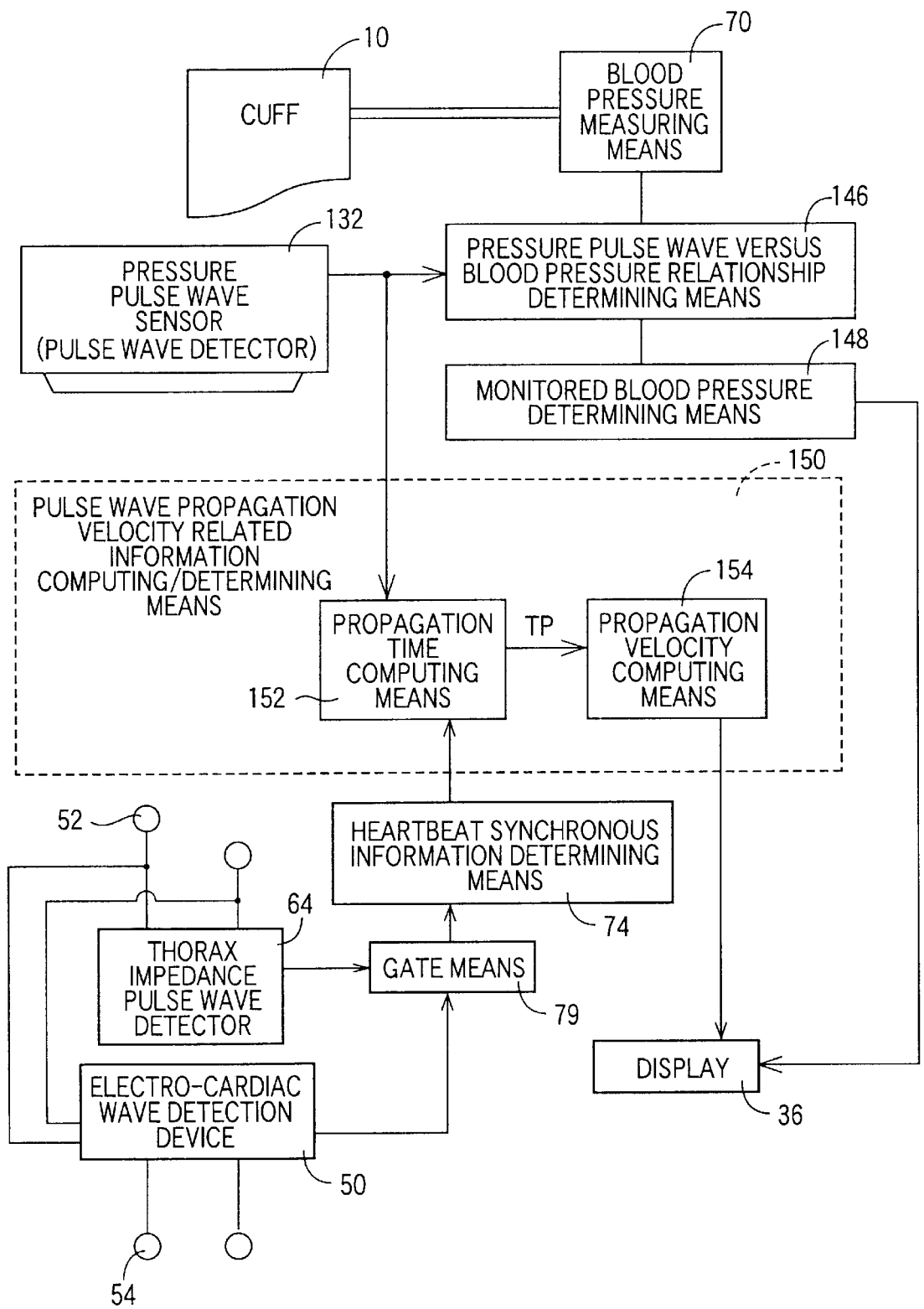
FIG. 15 is a block diagram of the electronic control device of the continuous blood pressure measuring apparatus of FIG. 14, illustrating the control function thereof.
Figure 16:
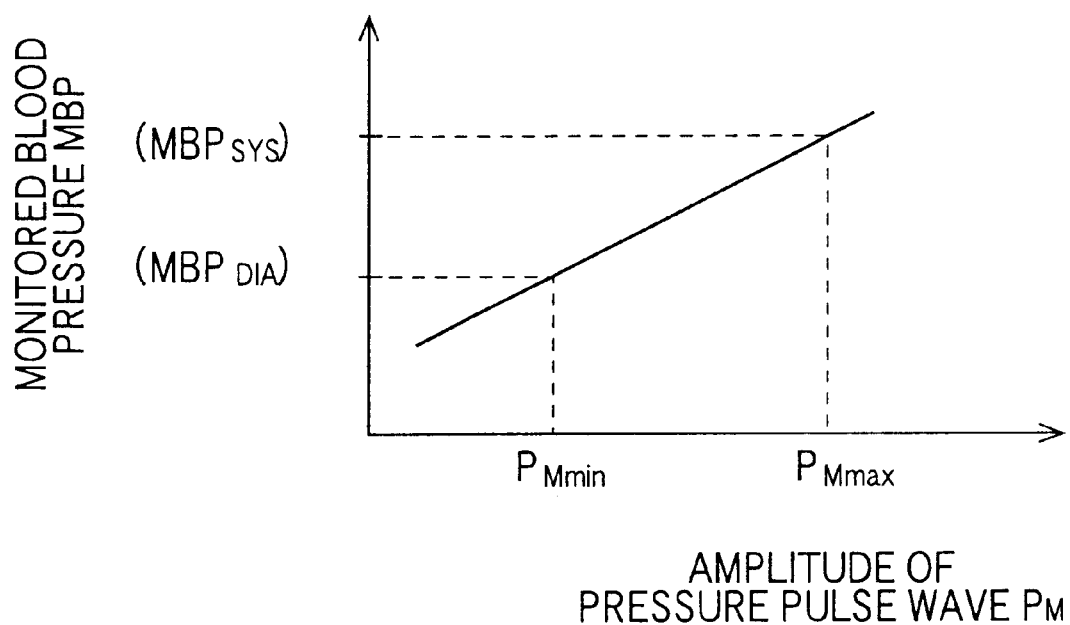
FIG. 16 is a graph of a relationship that can be used in the embodiment of FIG. 14.

FIG. 15 is a schematic block diagram illustrating the control operation of the electronic control device 28 of the continuous blood pressure measuring apparatus 120. Referring to FIG. 15, a pressure pulse wave versus blood pressure relationship determining means 146 determines the relationship between the amplitude of a pressure pulse wave $P_M$ and the monitored blood pressure MBP for each subject based on the amplitude of the pressure pulse wave $P_M$ detected by the pressure pulse wave sensor 132 and the blood pressure BP measured by the blood pressure measuring means 70. The relationship is typically indicated by a graph as shown in FIG. 16 and expressed by a formula MBP=A·$P_M$+B, where A is a constant representing the gradient of the graph, and B is a constant representing the intercept.

Monitored blood pressure value determining means 148 sequentially determines the highest blood pressure $MBP_{M\text{-}SYS}$ and the lowest blood pressure $MBP_{DIA}$ (monitored blood pressure) based on the highest value $P_{Mmax}$ (upper peak value) and the lowest value $P_{Mmin}$ (lower peak value) in the amplitude of the pressure pulse wave detected by the pressure pulse wave sensor 132 by using the above relationship, and causes the monitored blood pressure value MBP to be continuously shown on the display 36.

A pulse wave propagation velocity related information computing means 150 is composed of a propagation time computing means 152 and a propagation velocity computing means 154. The propagation time computing means 152 computes a time difference between a time a predetermined part periodically appears in the induced electro-cardiac wave and a time a predetermined part periodically appears in the pressure pulse wave. For example, a first time difference $TD_{RP}$ which is the time difference between a time a Q wave of the induced electro-cardiac wave periodically appears and a time a rising edge of the pressure pulse wave periodically appears. The propagation time computing means also computes a time difference between a time a predetermined part periodically appears in the induced electro-cardiac wave and a time a predetermined part periodically appears in the partial impedance pulse wave $SM_{IMP(P)}$. For example, a second time difference $TD_{RI}$ which is the time difference between a time the Q wave of the induced electro-cardiac wave periodically appears and a time a rising edge of the partial impedance pulse wave $SM_{IMP(P)}$ periodically appears. Then, the second time difference $TD_{RI}$ is subtracted from the first time difference $TD_{RP}$ to obtain the propagation time TP from the heart to the wrist 124 where the effect of the pressure pulse wave sensor 132 reaches. Since the second time difference $TD_{RI}$ corresponds to the preejection period PEP in FIG. 6, the propagation time does not include the preejection period PEP.

The propagation velocity computing means 154 computes the propagation velocity PWV (m/sec) based on the propagation time TP computed by means of a predefined formula 2 below. In the formula 2 below, $L_2$ is a distance from the left ventricle of the heart to a bodily position where the pressure pulse wave sensor 132 is fitted and pressed against it. The distance $L_2$ is defined in advance based on tests.

$$PWV = L_2/TP \qquad (2)$$

Figure 17:
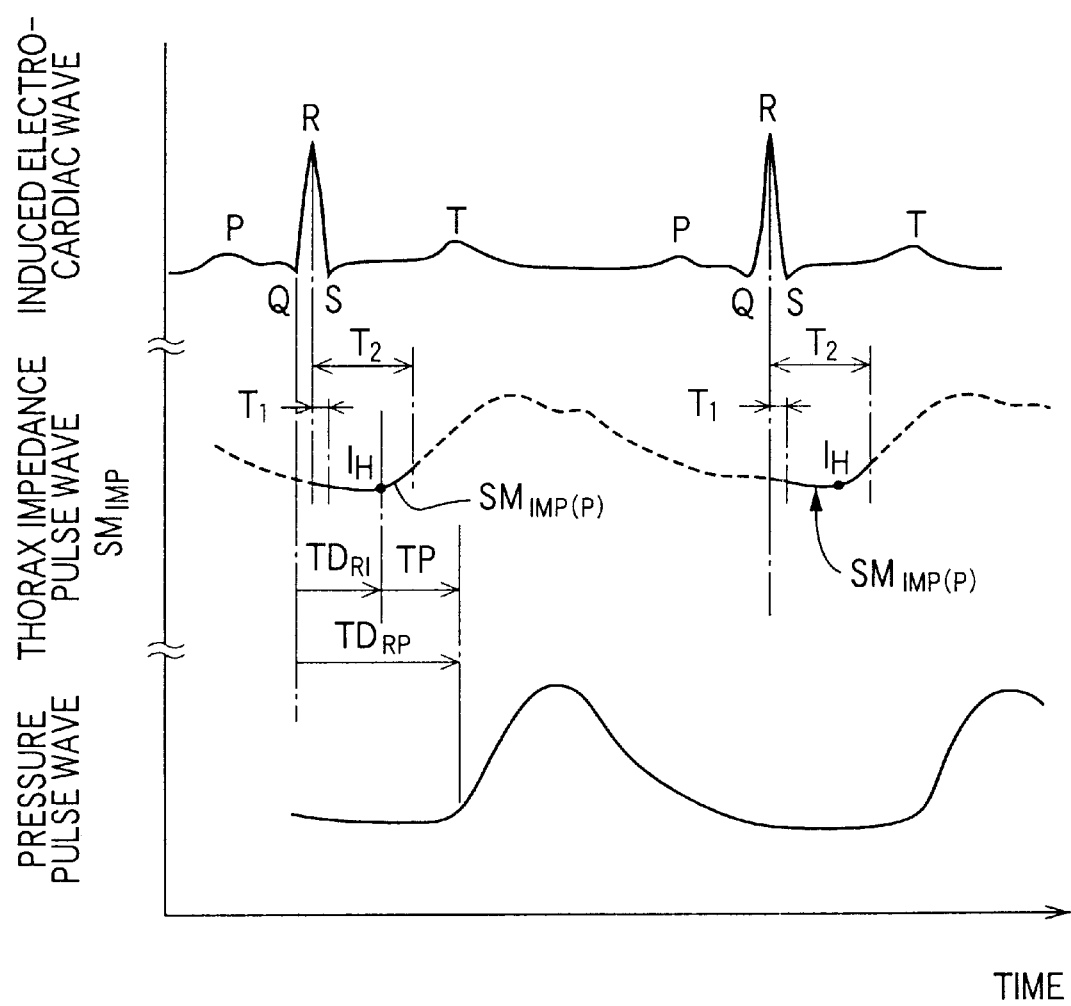
FIG. 17 is a timing chart illustrating a partial impedance pulse wave $SM_{IMP(P)}$ taken in under the control of the electronic control device of the embodiment of FIG. 14 as well as a first time difference $TD_{RP}$, a second time difference $TD_{RI}$ and a propagation time TP determined by the electronic control device.
Figure 18:
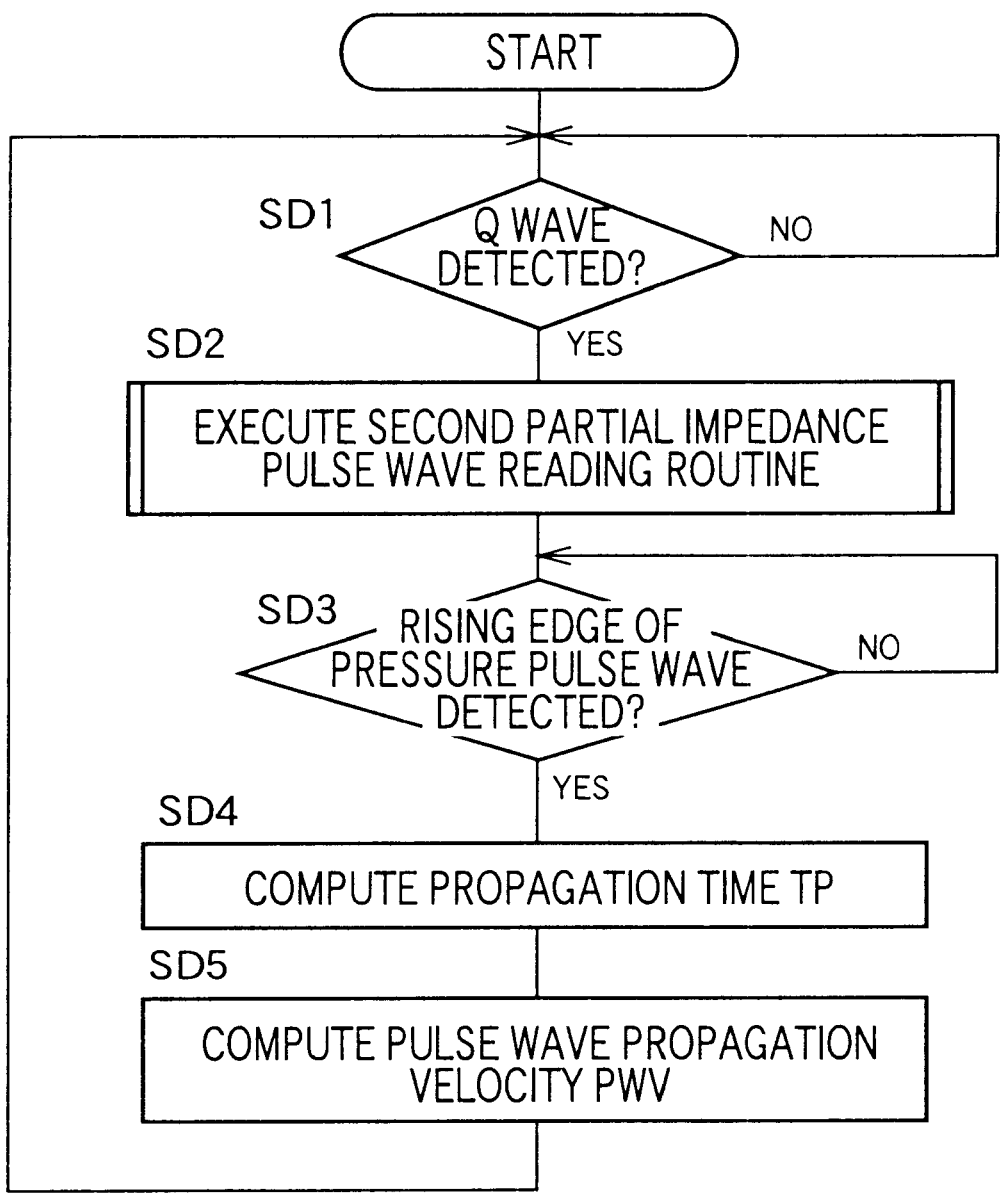
FIG. 18 is a flow chart of the operation of the electronic control device of the embodiment of the continuous blood pressure measuring apparatus of FIG. 14, illustrating the operation of computing the pulse wave propagation velocity.

FIG. 18 is a flow chart of an operation of computing the pulse wave propagation velocity of the electronic control device 28 of the continuous blood pressure measuring apparatus 120. Referring to FIG. 18, in SD1, it is determined whether the Q wave of the induced electro-cardiac wave is detected by the electro-cardiac wave detection device 50 or not. If the Q wave of the induced electro-cardiac wave is not detected, the operation of SD1 is repeated. If, on the other hand, the Q wave of the induced electro-cardiac wave is detected, the electronic control device proceeds to SD2 where the second partial impedance pulse wave $SM_{IMP(P)}$ reading routine, as illustrated in detail in FIG. 12, is executed. This is done so that the partial impedance pulse wave $SM_{IMP(P)}$ is read as part of the thorax impedance pulse wave $SM_{IMP}$ between the end of the first time $T_1$ and the end of the second time $T_2$, and a rising edge of the partial impedance pulse wave $SM_{IMP(P)}$ is selected as heartbeat synchronous information $I_H$. The end of the first time $T_1$ is made to be equal to 50 msec. starting from the detection of the R wave of the induced electro-cardiac wave, and the end of the second time $T_2$ is made to be equal to 150 msec. In FIG. 17, each part shown by a solid line in the graph indicates a partial impedance pulse wave $SM_{IMP(P)}$ which is read by the second partial impedance pulse wave reading routine.

Next in SD3, the pressure pulse wave sensor 132 determines whether a rising edge of the pressure pulse wave is detected or not. If a rising edge of the pressure pulse wave is not detected, the operation of SD3 is repeated. If, on the other hand, a rising edge of the pressure pulse wave is detected, SD4 and SD5 that correspond to the operation of the pulse wave propagation velocity related information computing means 150 are carried out.

In SD4 that corresponds to the propagation time computing means 152, the first time difference $TD_{RP}$ which is the time difference between a time the Q wave of the induced electro-cardiac wave periodically appears and a time a rising edge of the pressure pulse wave periodically appears, and the second time difference $TD_{RI}$ which is a time difference between a time the Q wave of the induced electro-cardiac wave periodically appears and a time a rising edge of the partial impedance pulse wave $SM_{IMP(P)}$ periodically appears are computed. The second time difference $TD_{RI}$ is subtracted from the first time difference $TD_{RP}$ to determine the propagation time TP from the heart to the wrist 124 where the effect of the pressure pulse wave sensor 143 reaches.

Then, in SD5 corresponding to the operation of the propagation velocity computing means 154, the pulse wave propagation velocity PWV is computed based on the propagation time TP determined in SD4 by using the formula (2) that is stored in advance. The obtained pulse wave propagation velocity PWV may be used to estimate the extent of arteriosclerosis and peripheral resistance according to an algorithm (not shown), or used by the pressure pulse wave versus blood pressure relationship determining means 146 to estimate the blood pressure at the start of an operation for determining the relationship.

As described above, with this embodiment, the gate means 79 (SB1 through SB6) takes in the partial impedance pulse wave $SM_{IMP(P)}$ as part of the thorax impedance pulse wave $SM_{IMP}$ detected by the thorax impedance pulse wave detector 64 between the end of the first time $T_1$ starting from the detection of the R wave of the induced electro-cardiac wave and the end of the second time $T_2$. Then, the propagation time computing means 152 (SD4) computes the first time difference $TD_{RP}$ which is the time difference between a time the Q wave of the induced electro-cardiac wave is periodically detected by the electro-cardiac wave detection device 50 and a time a rising edge of the pressure pulse wave is periodically detected by the pressure pulse wave sensor 132, and the second time difference $TD_{RI}$ which is the time difference between a time the Q wave of the induced electro-cardiac wave is periodically detected and a time a rising edge of the partial impedance pulse wave $SM_{IMP(P)}$, extracted by the gate means 79 (SB1 through SB6), is periodically detected. Then, the propagation time computing means 152 (SD4) subtracts the second time difference $TD_{RI}$ from the first time difference $TD_{RP}$ to determine the propagation time TP. As a result the pulse wave propagation velocity PWV is computed based on the time difference TP. Thus, the second time difference $TD_{RI}$ is accurate because it is computed by using a rising edge of the partial impedance pulse wave $SM_{IMP(P)}$ that is largely unaffected by noise. Therefore, the obtained pulse wave propagation velocity PWV is accurate because the time difference TP and the pulse wave propagation velocity PWV are computed based on the accurately determined second time difference $TD_{RI}$.

Additionally, in this embodiment, a pressure pulse wave sensor 132 that is used for continuously measuring the arterial pressure by detecting the pressure pulse wave of the radial artery 140 is also used as pulse wave detector so that the cost of the entire apparatus can be reduced in addition to other advantages.

Finally, with this embodiment, the intake period of the gate means 79 (SB1 through SB6) is determined solely based on the induced electro-cardiac wave that is minimally affected by noise. In other words, the intake period can be determined accurately and reliably as well as any other information required to determine the intake period.

Figure 19:
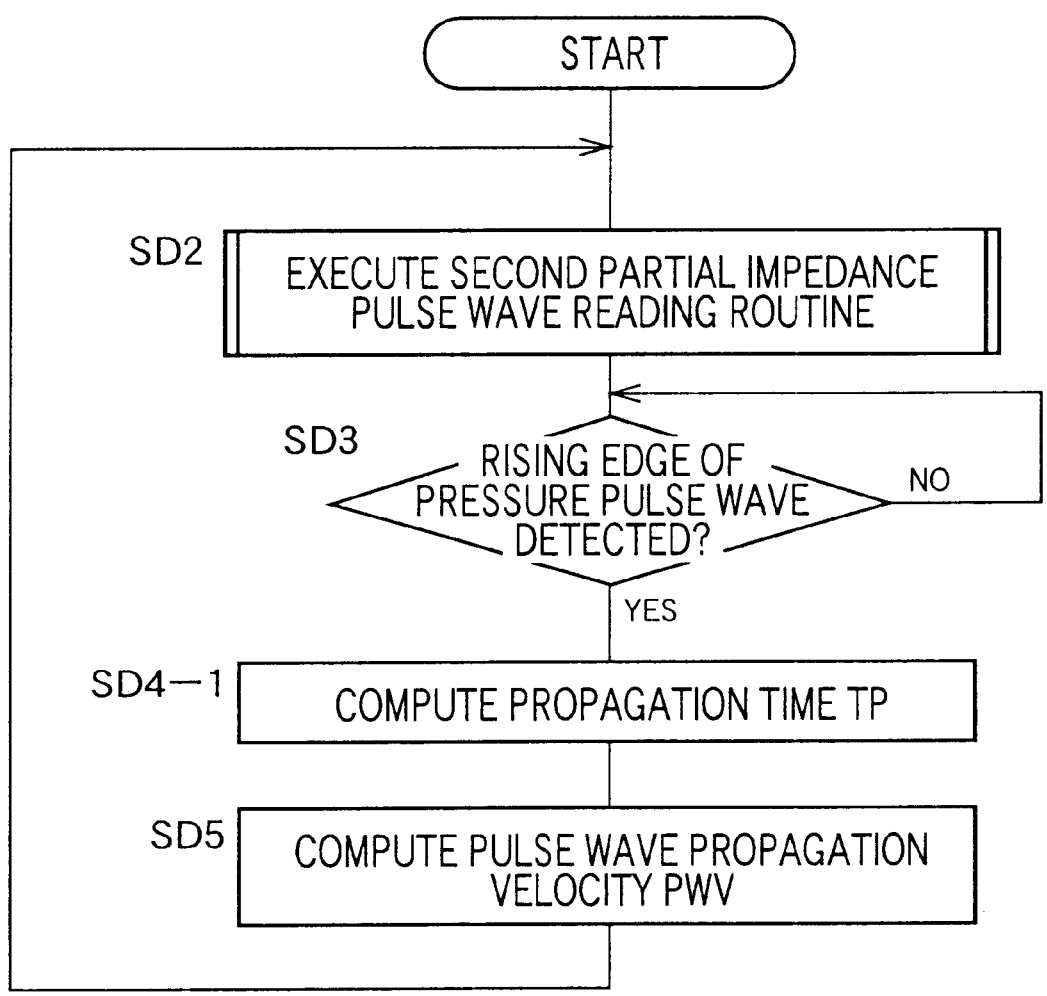
FIG. 19 is a flow chart of an operation of an electronic control device of still another embodiment of the invention, illustrating the operation of computing the pulse wave propagation velocity.

Now, still another embodiment of the pulse wave propagation velocity related information acquiring apparatus according to the invention that is used for a continuous blood pressure monitoring apparatus will be described. FIG. 19 is a flow chart of the operation of the electronic control device 28 of the apparatus with a configuration the same as its counterpart of FIG. 14. The flow chart of FIG. 19 is the same as that of FIG. 18 except that SD1 of FIG. 18 is removed and SD4 of FIG. 18 is replaced by SD4-1 in FIG. 19. Now, only SD4-1 that differentiates the operation of the electronic control device 28 of this embodiment will be described below.

In SD4-1 of FIG. 19 that corresponds to the operation of propagation time computing means 154, the propagation time TP from a rising edge of the partial impedance pulse wave $SM_{IMP(P)}$ detected and selected as heartbeat synchronous information $I_H$ in SD2 to a rising edge of the pressure pulse wave detected in SD3, or from the heart to the wrist 124 where the effect of the pressure pulse wave sensor 132 reaches is directly computed.

With this embodiment, the gate means 79 (SB1 through SB6) takes in the partial impedance pulse wave $SM_{IMP(P)}$ as part of the thorax impedance pulse wave $SM_{IMP}$ detected by the thorax impedance pulse wave detector 64 between the end of the first time $T_1$ starting from the detection of the R wave of the induced electro-cardiac wave and the end of the second time $T_2$. Then, the propagation time computing means 152 (SD4) computes the propagation time TP from a rising edge of the partial impedance pulse wave $SM_{IMP(P)}$ extracted by the gate means (SB1 through SB6) to a rising edge of the pressure pulse wave detected by the pressure pulse wave sensor 132. Subsequently, the propagation velocity computing means 154 (SD5) computes the pulse wave propagation velocity PWV based on the obtained time difference TP. Thus, the time difference TP is accurate because it is computed based on a rising edge of the partial impedance pulse wave $SM_{IMP(P)}$ that is largely unaffected by noise. Therefore, the obtained pulse wave propagation velocity PWV is accurate because it is computed based on the accurately determined time difference TP.

Figure 20:
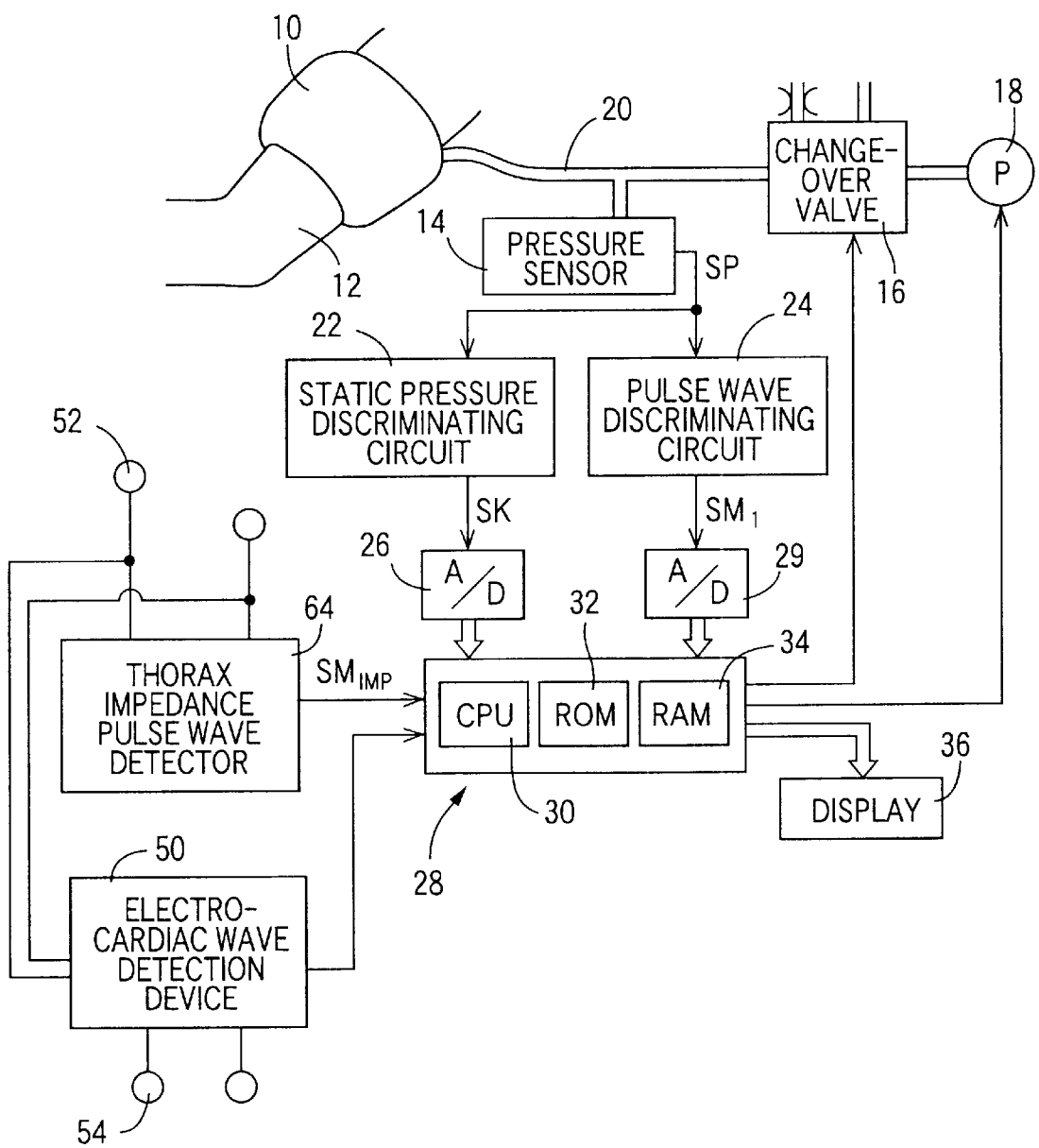
FIG. 20 is a block diagram of still another embodiment of a blood pressure measuring apparatus provided with a pulse wave propagation velocity related information acquiring apparatus.
Figure 21:
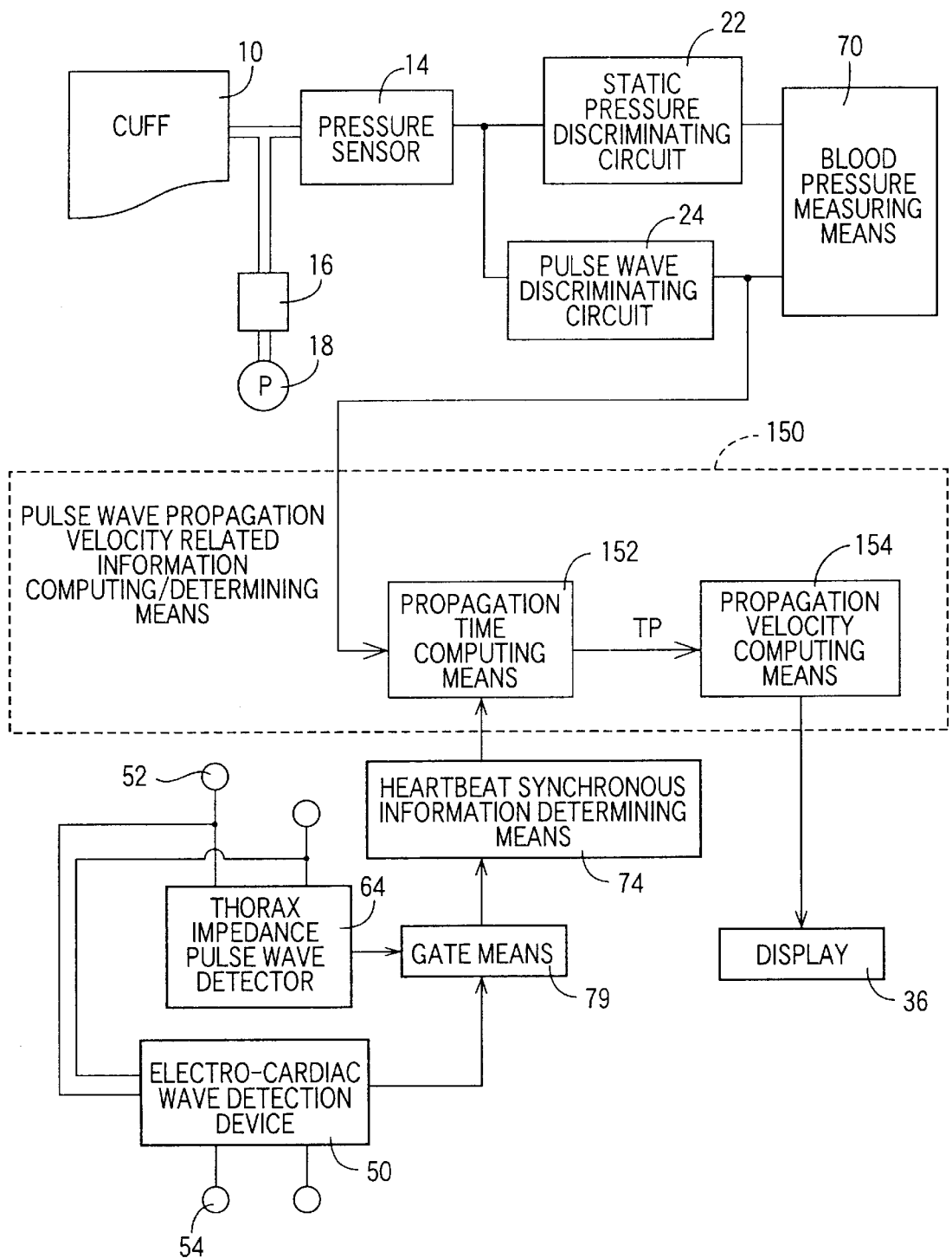
FIG. 21 is a block diagram of an electronic control device of the blood pressure measuring apparatus of FIG. 20, illustrating the control function thereof.
Figure 22:
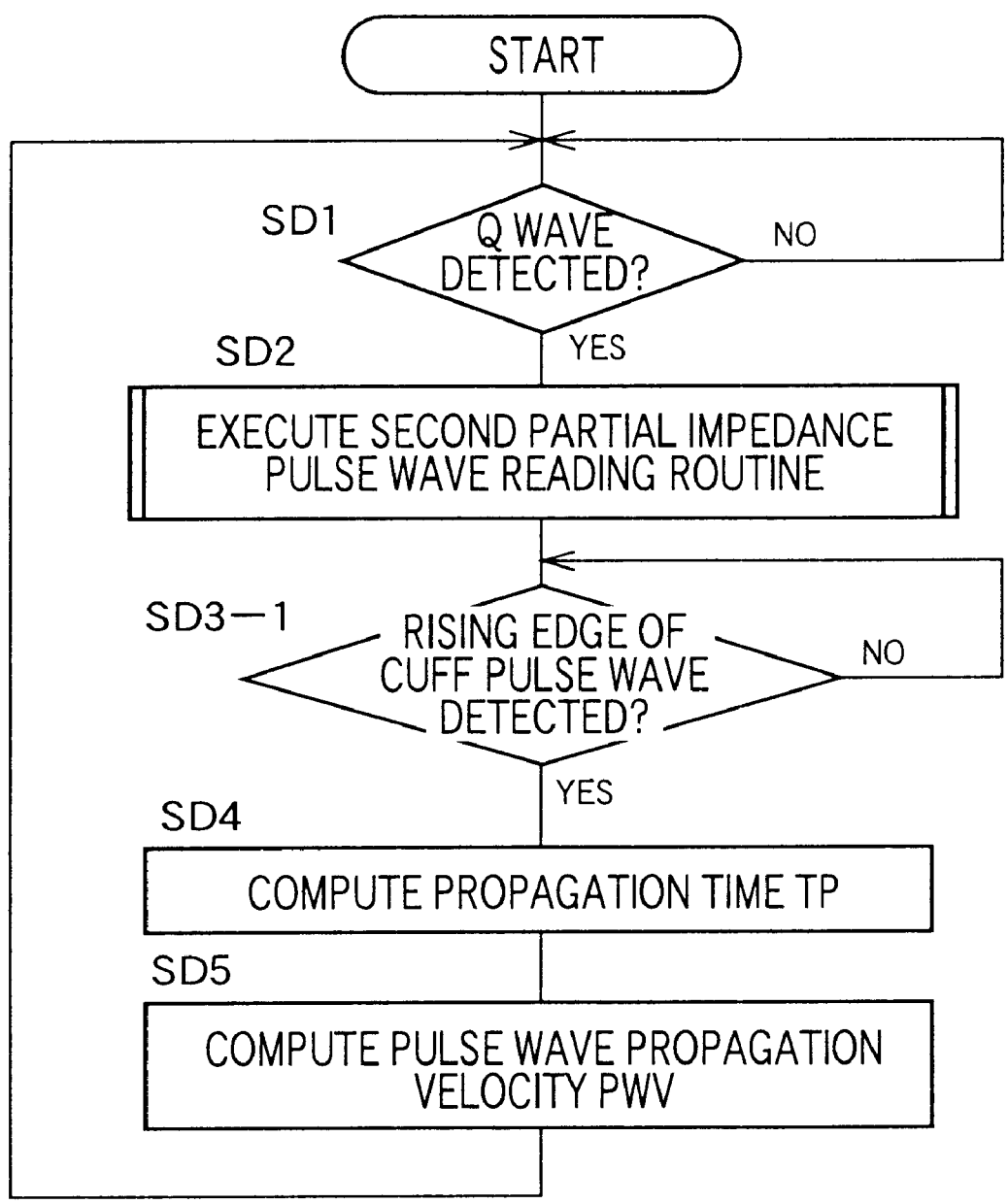
FIG. 22 is a flow chart of an operation of the electronic control device of the embodiment of FIG. 20, illustrating the operation of computing the pulse wave propagation velocity.

Now, still another embodiment of the pulse wave propagation velocity related information acquiring apparatus according to the invention will be described below by referring to FIGS. 20 through 22, of which FIGS. 20 and 21 correspond to FIGS. 14 and 15 of the above described embodiment and FIG. 22 corresponds to FIG. 18. This embodiment differs from that of FIGS. 14 and 15 in that the pulse wave detector is composed of the cuff 10, the pressure sensor 14 and the pulse wave discriminating circuit 24. Also, this embodiment differs from that of FIGS. 14 and 15 in that a cuff pulse wave is used in place of a pressure pulse wave and it is not composed of a pressure pulse wave versus blood pressure relationship determining means 146 and a monitored blood pressure determining means 148.

With this embodiment, the propagation time computing means 152 (SD4) computes the first time difference $TD_{RP}$ which is the time difference between a time the Q wave of the induced electro-cardiac wave periodically appears and a time a rising edge of the cuff pulse wave that can be detected under pressure of the cuff 10 that is lower than the average blood pressure periodically appears. The propagation time computing means 152 (SD4) also computes the second time difference $TD_{RI}$ which is the time difference between a time the Q wave of the induced electro-cardiac wave periodically appears and a time a rising edge of the partial impedance pulse wave $SM_{IMP(P)}$ periodically appears, and then subtracts the second time difference $TD_{RI}$ from the first time difference $TD_{RP}$ to determine the propagation time TP. Then, the propagation velocity computing means 154 (SD5) computes the pulse wave propagation velocity PWV based on the time difference TP. Thus, in this embodiment again, the second time difference $TD_{RI}$ is accurate because it is computed by using a rising edge of the partial impedance pulse wave $SM_{IMP(P)}$ that is largely unaffected by noise. Therefore, the pulse wave propagation velocity PWV obtained is accurate because the time difference TP and the pulse wave propagation velocity are computed based on the accurately determined second time difference $TD_{RI}$.

Additionally, with this embodiment, the pulse wave sensor is composed of the cuff 10, the pressure sensor 14 and the pulse wave discriminating circuit 24, which may be shared by the blood pressure measuring apparatus which includes the blood pressure measuring means 70 to reduce the cost of the apparatus.

Figure 23:
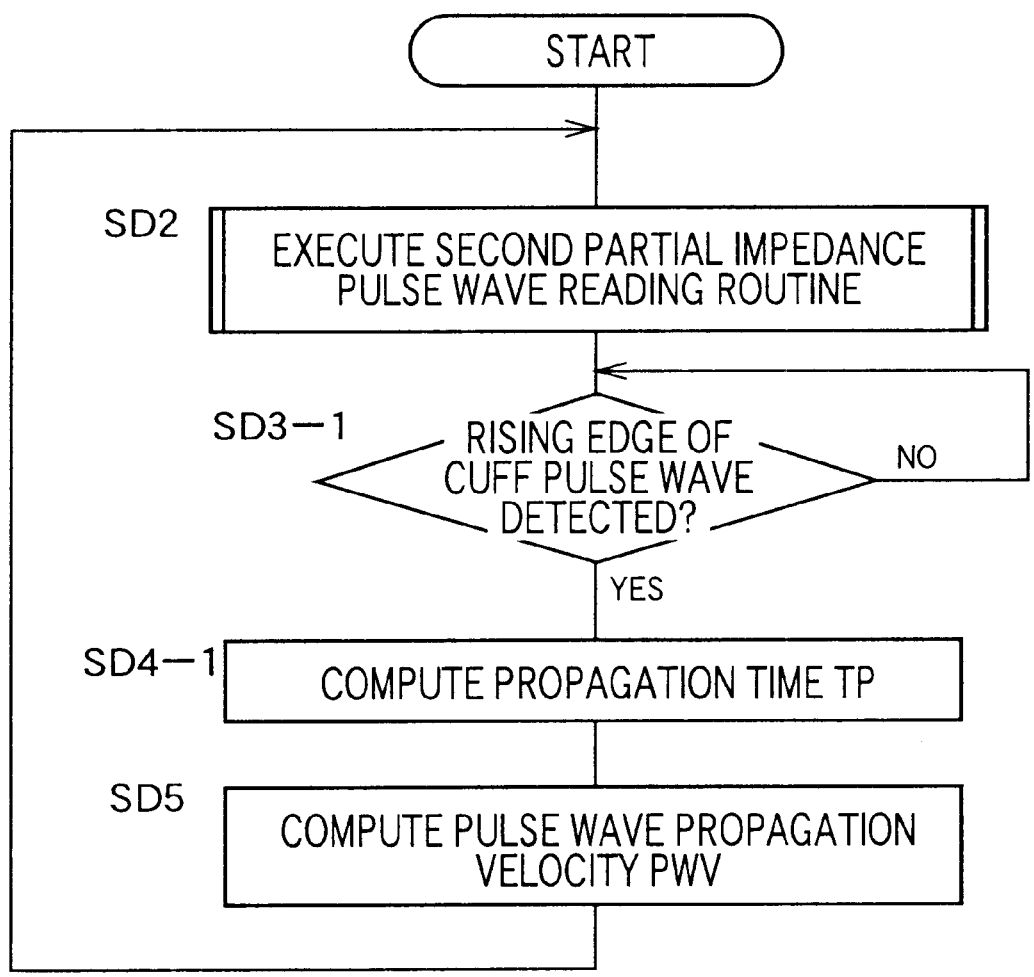
FIG. 23 is a flow chart of an operation of an electronic control device of still another embodiment of the invention, illustrating the operation of computing the pulse wave propagation velocity.

Now, still another embodiment of the invention that is a continuous blood pressure measuring apparatus will be described. FIG. 23 is a flow chart of the operation of the electronic control device 28 of the embodiment which has a configuration similar to that of FIG. 20. The flow chart of FIG. 23 is the same as that of FIG. 22 except that SD1 is removed and SD4 is similar to SD4-1 in FIG. 19.

In this embodiment, the propagation time TP from a rising edge of the partial impedance pulse wave $SM_{IMP(P)}$, selected in SB7 of the second partial impedance pulse wave reading routine of SD2, to a rising edge of the cuff pulse wave detected in SD3-1 or from the heart to the upper arm 12, where the cuff 10 is fitted, is directly computed. The net result is similar to that of FIG. 19.

Now, an embodiment of the pulse wave propagation velocity related information acquiring apparatus according to the invention will be described below. This embodiment may be used in a blood pressure measuring apparatus 156 that has a similar configuration to that of FIG. 1 except for the control function of the electronic control device 28. More specifically, the blood pressure measuring apparatus 156 of this embodiment differs from the continuous blood pressure measuring apparatus 120 of FIG. 14 in that it is composed of the photoelectric pulse wave sensor 40 as the pulse wave detector, and the photoelectric pulse wave is used in place of the pressure pulse wave.

Figure 24:
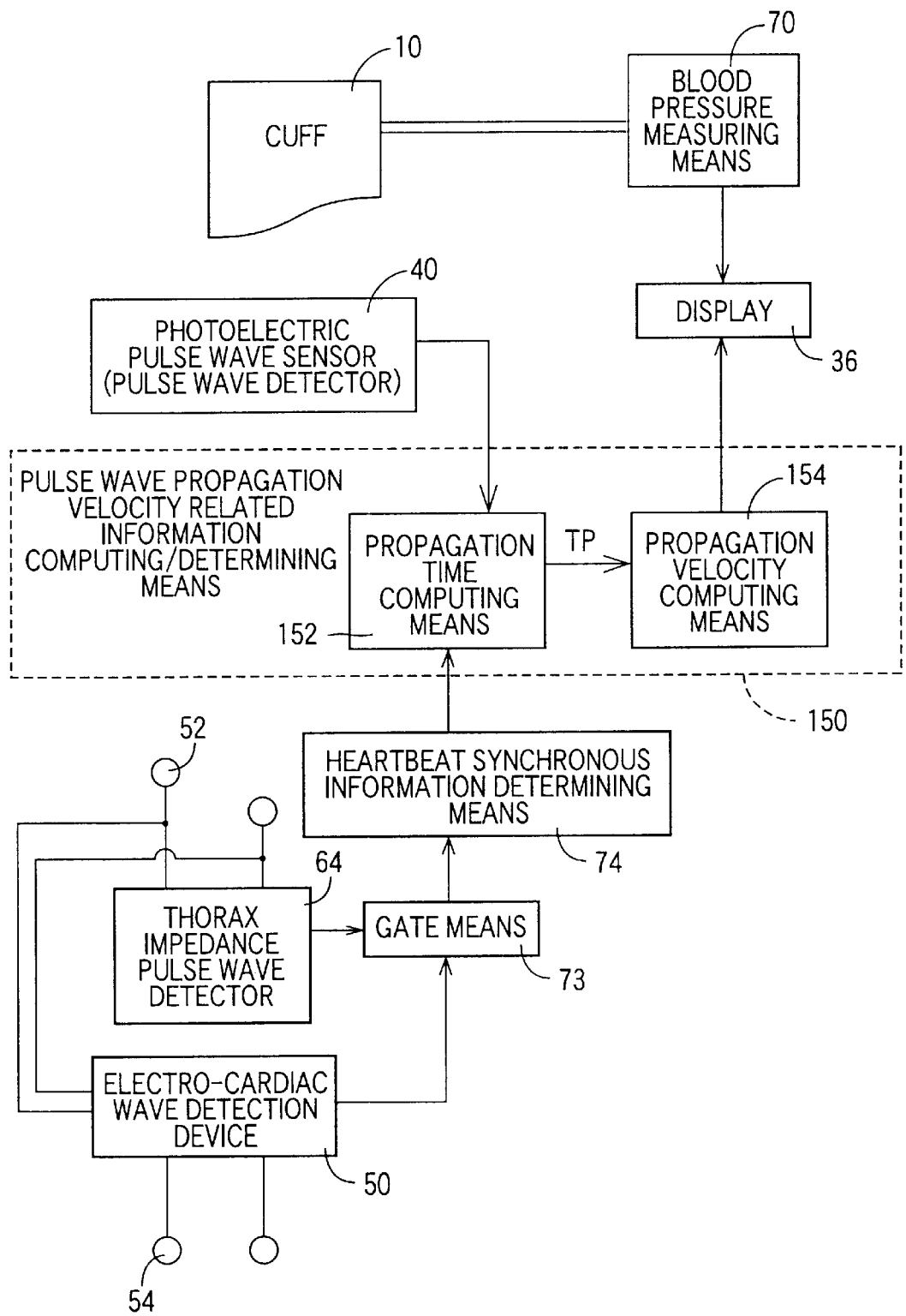
FIG. 24 is a block diagram of an electronic control device of another embodiment of a blood pressure measuring apparatus provided with a pulse wave propagation velocity related information acquiring apparatus, illustrating the control function thereof.
Figure 25:
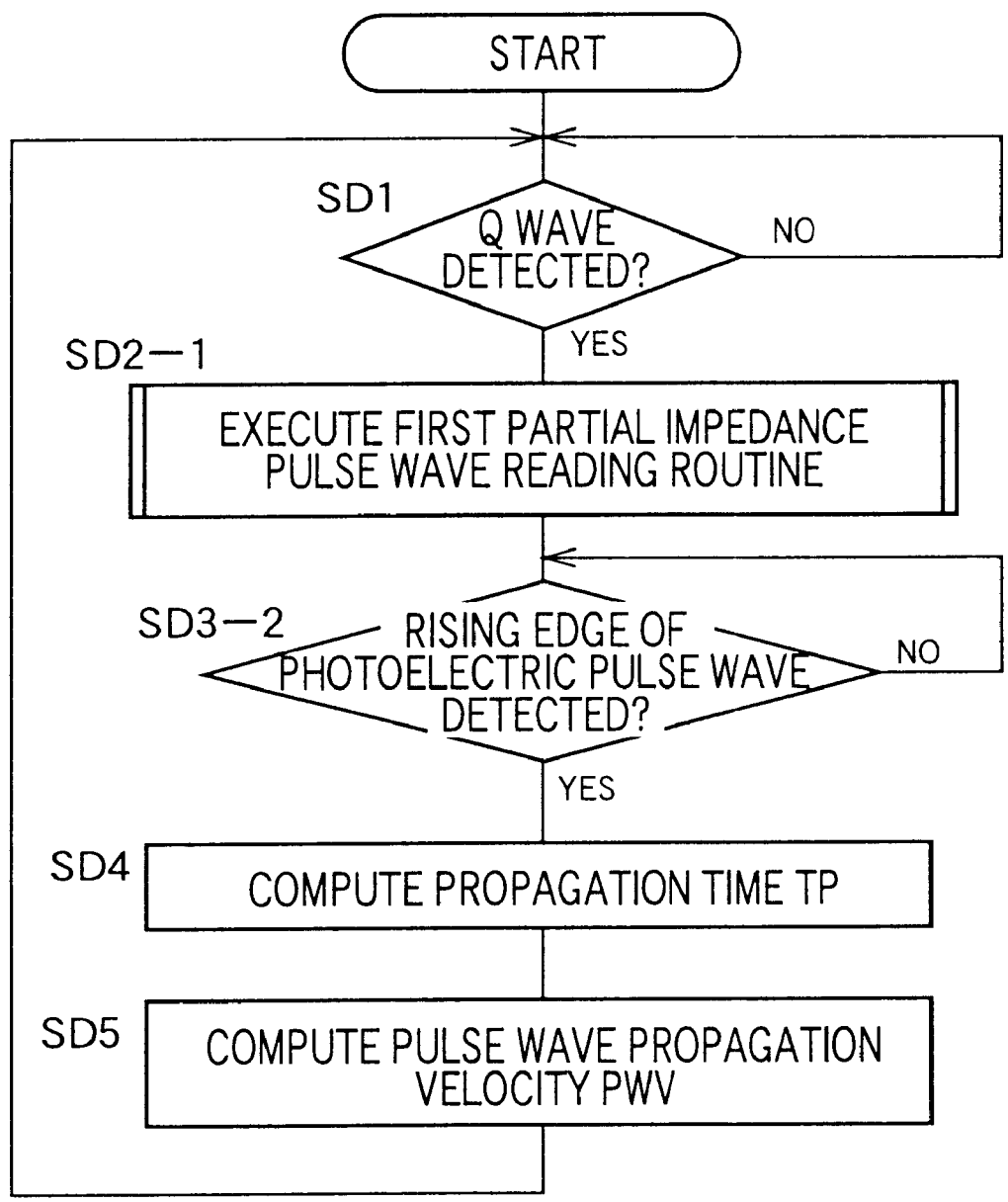
FIG. 25 is a flow chart of an operation of an electronic control device of the embodiment of FIG. 24, illustrating the operation of computing the pulse wave propagation velocity.

FIG. 24 is a schematic block diagram illustrating the functional features of a principal part of the electronic control device 28 of the blood pressure measuring apparatus 156 and FIG. 25 is a flow chart of the operation of the electronic control device 28 for computing the pulse wave propagation velocity. The block diagram of FIG. 24 differs from that of FIG. 15 in that the pressure pulse wave versus blood pressure relationship determining means 146 and the monitored blood pressure determining means 148 of FIG. 15 are removed. Also, the gate means 79, which is adapted to determine the period for extracting the partial impedance pulse wave $SM_{IMP(P)}$ solely based on the induced electro-cardiac wave in FIG. 15, is replaced by the gate means 73, which is adapted to determine the period of extracting the partial impedance pulse wave $SM_{IMP(P)}$ based on the induced electro-cardiac wave and the photoelectric pulse wave. The flow chart of FIG. 25 differs from that of FIG. 22 in that SD2 for executing the second partial impedance pulse wave reading routine of FIG. 22 is replaced by SD-1 for executing the first partial impedance pulse wave reading routine, and SD3 for detecting a rising edge of the pressure pulse wave in FIG. 22 is replaced by SD3-2 for detecting a rising edge of the photoelectric pulse wave. In this embodiment, as in the case of the immediately preceding embodiment, the propagation time computing means 152 (SD4) computes the first time difference $TD_{RP}$ which is the time difference between a time the Q wave of the induced electro-cardiac wave periodically appears and a time a rising edge of the cuff pulse wave that can be detected under pressure of the cuff 10 that is lower than the average blood pressure periodically appears. The propagation time computing means 152 (SD4) also computes the second time difference $TD_{RI}$ which is the time difference between a time the Q wave of the induced electro-cardiac wave periodically appears and a time a rising edge of the partial impedance pulse wave $SM_{IMP(P)}$ periodically appears, and then subtracts the second time difference $TD_{RI}$ from the first time difference $TD_{RP}$ to determine the propagation time TP. Then, the propagation velocity computing means 154 (SD5) computes the pulse wave propagation velocity PWV based on the time difference TP. Therefore, this embodiment provides advantages which are the same as those of the embodiment of FIG. 20. Additionally, since the end of the intake period of the gate means (SB1 through SB5) is determined based on the photoelectric pulse wave, the photoelectric pulse wave sensor 40, which is adapted to compute the pulse wave propagation time TP, can also be used to determine the end of the intake period. Additionally, since the photoelectric pulse wave detected by the photoelectric pulse wave sensor 40 is largely free from electromagnetic noise, the end of the intake period can be determined accurately.

Furthermore, this embodiment is designed to include a photoelectric pulse wave sensor 40 operating as a pulse wave detector. When the pulse oximeter is also included, as illustrated in FIG. 13, which is provided with the photoelectric pulse wave sensor for detecting the pulse wave by using light with two wavelengths for irradiation, the photoelectric pulse wave sensor of the pulse oximeter can be shared by the pulse wave detector to reduce the cost of the pulse wave detector.

Figure 26:
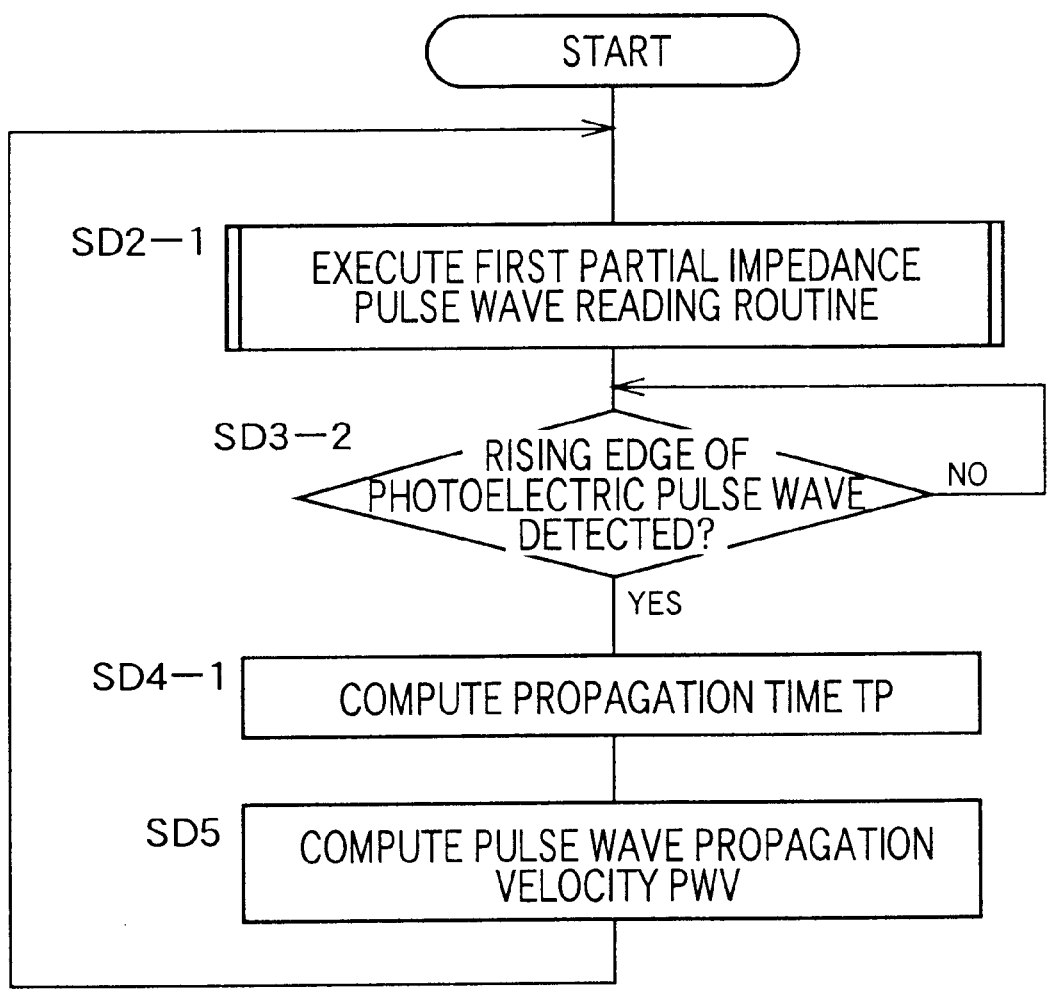
FIG. 26 is a flow chart of an operation of an electronic control device of still another embodiment of the invention, illustrating the operation of computing the pulse wave propagation velocity.

Now, still another embodiment of the invention will be described below. FIG. 26 is a flow chart of the operation of the electronic control device 28 of this embodiment of the blood pressure measuring apparatus with a configuration the same as the blood pressure measuring apparatus 156 of FIG. 24. The flow chart of FIG. 26 is the same as that of FIG. 25 except that SD1 is removed therefrom and SD4 of FIG. 25 is replaced by SD4-1 that is similar to its counterpart of FIG. 19.

With this embodiment, the propagation time TP from the rising edge of the partial impedance pulse wave $SM_{IMP(P)}$ selected in SB7 by the first partial impedance pulse wave reading routine of SD2 to the rising edge of the photoelectric pulse wave detected in SD3-2, or from the heart to the fingertip where the photoelectric pulse wave sensor 132 is fitted, is directly computed. This arrangement provides the same advantages as those of the arrangement of FIG. 25.

Figure 27:
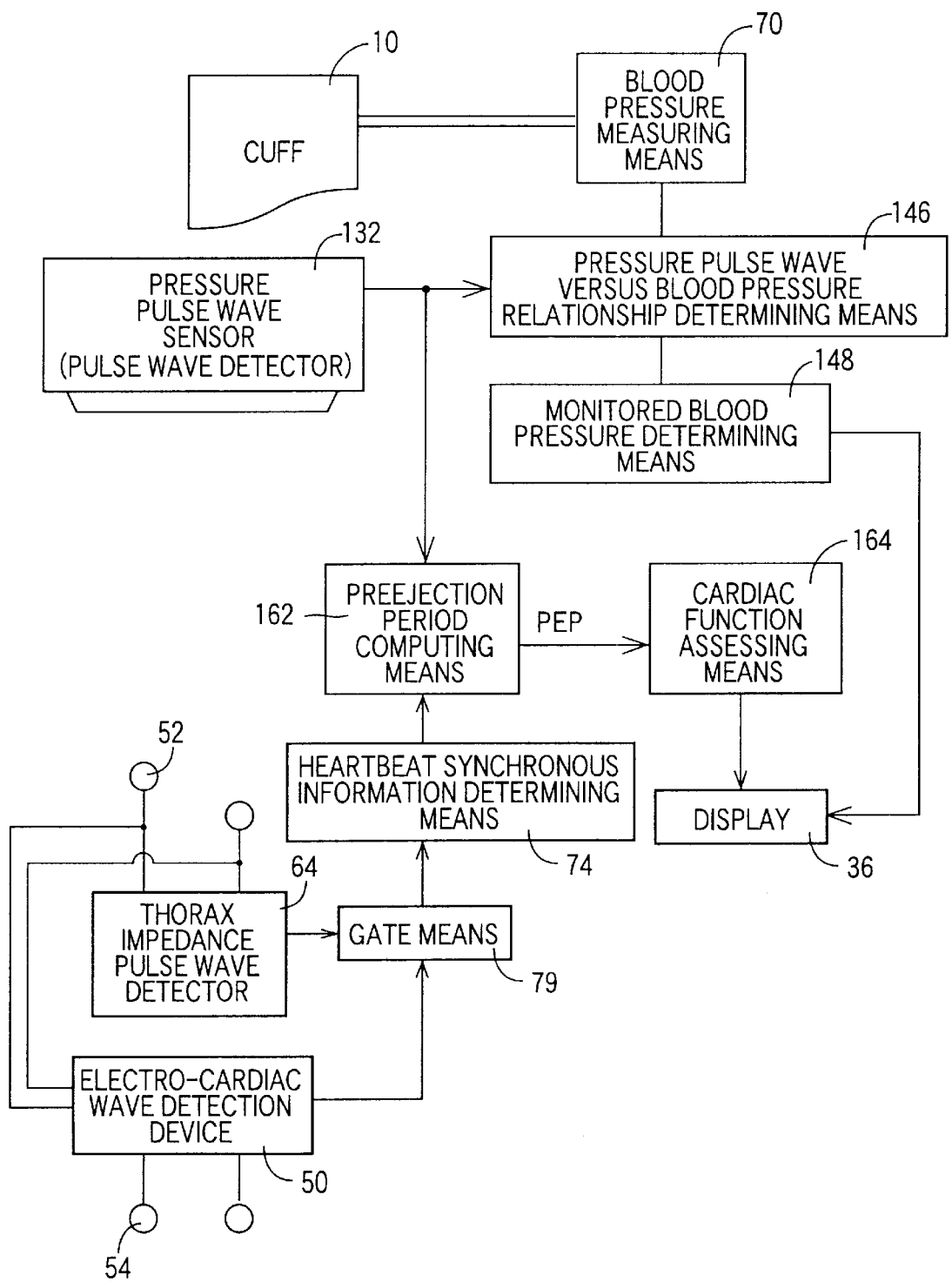
FIG. 27 is a block diagram of another embodiment of a continuous blood pressure measuring apparatus according to the invention and provided with a preejection period measuring apparatus.

Still another embodiment of the invention will now be described below. FIG. 27 is a schematic block diagram of this embodiment of continuous blood pressure measuring apparatus 160 which includes a preejection period measuring apparatus or a cardiac function assessing apparatus. Note that this embodiment of continuous blood pressure measuring apparatus 160 has a configuration which is the same as that of the continuous blood pressure measuring apparatus 120 of FIG. 14 except for the control function.

Referring to FIG. 17, a preejection period computing means 162 computes the time difference between a time a predetermined part periodically appears in the induced electro-cardiac wave and a time a predetermined part periodically appears in the pressure pulse wave. For example, the first time difference $TD_{RP}$ which is the time difference between a time the Q wave of the induced electro-cardiac wave periodically appears and a time a rising edge of the pressure pulse wave periodically appears. The preejection period computing means 162 also computes the time difference between a time the predetermined part in the partial impedance pulse wave $SM_{IMP(P)}$ periodically appears and a time the predetermined part in the pressure pulse wave periodically appears. For example, the second time difference $TD_{RI}$ which is the time difference between a time a rising edge of the partial impedance pulse wave $SM_{IMP(P)}$ periodically appears and a time a rising edge of the pressure pulse wave periodically appears. Then, the second time difference $TD_{RI}$ is subtracted from the first time difference $TD_{RP}$ to obtain the preejection period PEP (msec) from a time when the heart (left ventricle) starts contracting to a time when the aortic valve is opened to pump out the blood.

The cardiac function assessing means 164 determines a rating E of the cardiac function from a pre-selected relationship based on the preejection period computed by the preejection period computing means 162. For instance, the preejection period PEP, which is expressed in terms of msec, is rated in terms of simple numerical values to produce the rating E of the cardiac function. A formula for producing the rating E of the cardiac function for the preejection period PEP preferably includes parameters such as the age and the sex of the living body which are used to modify the rating process.

Figure 28:
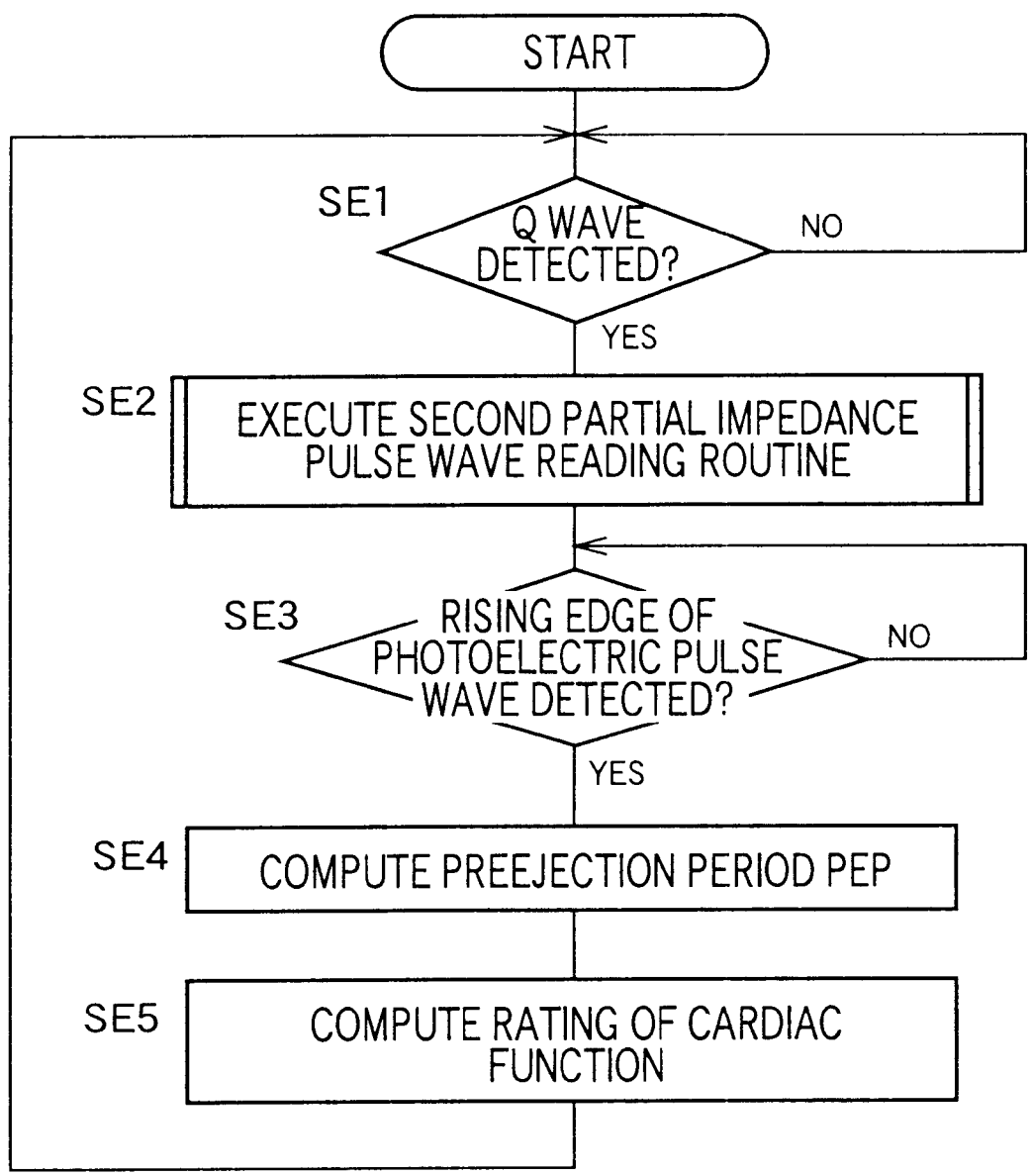
FIG. 28 is a flow chart of an operation of an electronic control device of the embodiment of the continuous blood pressure measuring apparatus of FIG. 27, illustrating the operation of computing the preejection period.

FIG. 28 is a flow chart of the operation of computing the preejection period of the electronic control device 28 of the continuous blood pressure measuring apparatus 160. Referring to FIG. 28, in SE1, it is determined whether the Q wave of the induced electro-cardiac wave is detected by the electro-cardiac wave detection device 50 or not. If the Q wave of the induced electro-cardiac wave is not detected, the operation of SE1 is repeated. If, on the other hand, the Q wave of the induced electro-cardiac wave is detected, the control device 28 proceeds to SE2 where the second partial impedance pulse wave $SM_{IMP(P)}$ reading routine as shown in FIG. 12 in detail is executed. Here a partial impedance pulse wave $SM_{IMP(P)}$ is taken in as part of the thorax impedance pulse wave $SM_{IMP}$, which is between the end of the first time $T_1$ that is made to be equal to 50 msec starting from the detection of the R wave of the induced electro-cardiac wave and the end of the second time $T_2$ that is made equal to 150 msec, and the rising edge of the partial impedance pulse wave $SM_{IMP(P)}$ is selected as heartbeat synchronous information $I_H$. In FIG. 17, each part shown by a solid line in the graph of the thorax impedance pulse wave $SM_{IMP}$ indicates a partial impedance pulse wave $SM_{IMP(P)}$ taken in by the second partial impedance pulse wave reading routine.

Next in SE3, the pressure pulse wave sensor 132 determines whether the rising edge of the pressure pulse wave is detected or not. If the rising edge of the pressure pulse wave is not detected, the operation of SE3 is repeated. If, on the other hand, the rising edge of the pressure pulse wave is detected, SE4 that corresponds to the operation of the preejection period computing means 162 is carried out.

Then, in SE4, as shown in FIG. 17, the first time difference $TD_{RP}$, which is the time difference between a time the Q wave of the induced electro-cardiac wave periodically appears and a time a rising edge of the pressure pulse wave periodically appears, and the second time difference $TD_{RI}$, which is the time difference between a time a rising edge of the partial impedance pulse wave $SM_{IMP(P)}$ periodically appears and a time a rising edge of the pressure pulse wave periodically appears, are computed. Then, the second time difference $TD_{RI}$ is subtracted from the first time difference $TD_{RP}$ to determine the preejection period PEP.

Then, in SE5 that corresponds to the operation of the cardiac function assessing means 164, the rating E of the cardiac function is computed by using a formula that is stored in advance and the actual preejection period PEP.

As described above, with this embodiment, the gate means 79 (SB1 through SB6) takes in a partial impedance pulse wave $SM_{IMP(P)}$ as part of the thorax impedance pulse wave $SM_{IMP}$, detected by the thorax impedance pulse wave detector 64, between the end of the first time $T_1$, starting from the detection of the R wave of the induced electro-cardiac wave, and the end of the second time $T_2$. Then, the preejection period computing means 162 (SE4) computes the first time difference $TD_{RP}$ which is the time difference between a time the Q wave of the induced electro-cardiac wave detected by the electro-cardiac wave detection device 50 periodically appears and a time a rising edge of the pressure pulse wave detected by the pressure pulse wave sensor 132 periodically appears. The preejection period computing means 162 (SE4) also computes the second time difference $TD_{RI}$ which is the time difference between a time a rising edge of the partial impedance pulse wave $SM_{IMP(P)}$ extracted by the gate means 79 (SE2) periodically appears and a time a rising edge of the pressure pulse wave detected by the pressure pulse wave sensor 132 periodically appears, and then subtracts the second time difference $TD_{RI}$ from the first time difference $TD_{RP}$ to determine the preejection period. Thus, the second time difference $TD_{RI}$ is accurate because it is computed by using a rising edge of the partial impedance pulse wave $SM_{IMP(P)}$ that is largely unaffected by noise. Therefore, the preejection period PEP obtained is accurate because it is computed by subtracting the accurate second time difference $TD_{RI}$ from the first time difference $TD_{RP}$.

Additionally, with this embodiment, the intake period of the gate means 79 (SB1 through SB6) is determined solely based on the induced electro-cardiac wave that is minimally affected by noise. In other words, the intake period can be determined accurately and reliably as well any other information required to determine the intake period.

Furthermore, this embodiment includes the cardiac function assessing means 164 (SE5) for assessing the cardiac function of the living body based on the preejection period PEP computed by the preejection period computing means 162 (SE4). With this arrangement, the cardiac function can be assessed accurately when compared with the assessment of the cardiac function conducted based on the preejection period determined by using a microphone.

Finally, in this embodiment, a pressure pulse wave sensor 132 that is used as the pulse wave detector is shared by the continuous blood pressure measuring apparatus 160 for measuring an arterial pressure by detecting the pressure pulse wave of a radial artery so that the cost of the entire apparatus can reduced in addition to the other advantages.

Figure 29:
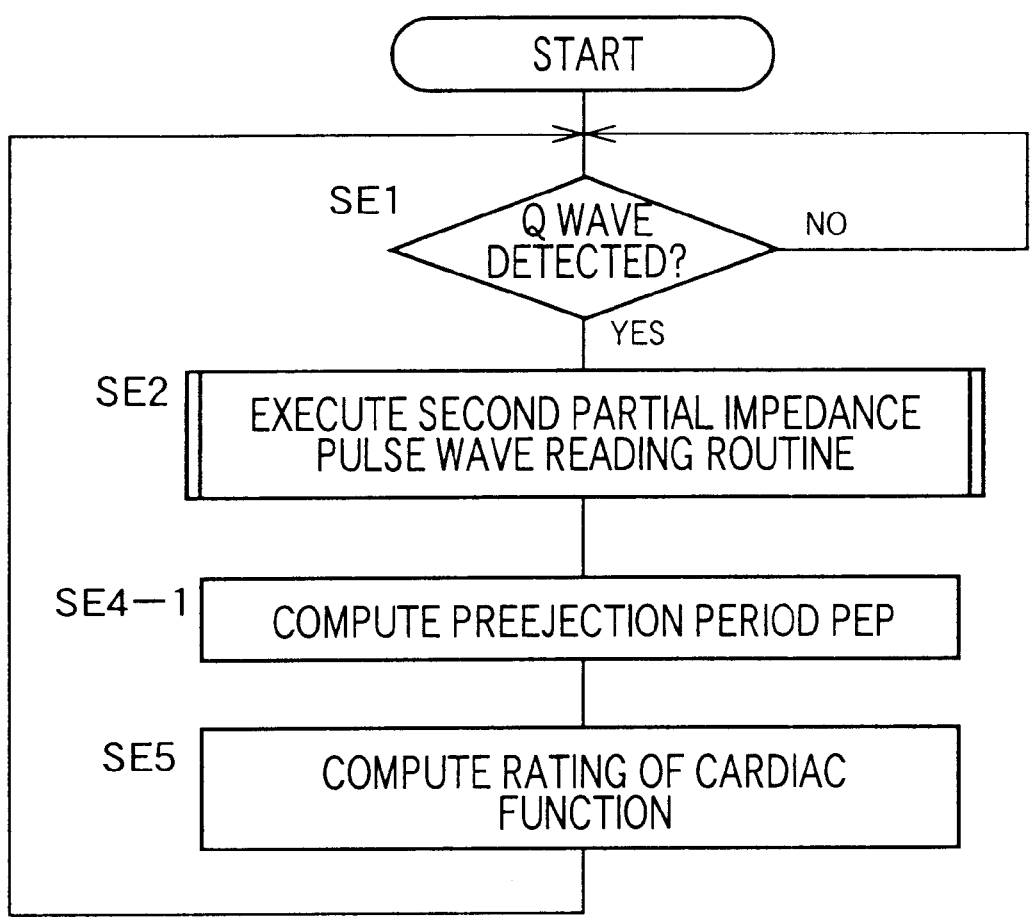
FIG. 29 is a flow chart of an operation of an electronic control device of still another embodiment, illustrating the operation of computing the preejection period.

Now, still another embodiment of preejection period measuring apparatus according to the invention will be described below. FIG. 29 is a flow chart of the operation of the electronic control device 28 that operates like its counterpart of the continuous blood pressure measuring apparatus shown in FIG. 14 for computing the preejection period. The flow chart of FIG. 29 differs from that of FIG. 14 in that SE3 of FIG. 14 is removed from FIG. 29 and SE4 of FIG. 4 is replaced by SE4-1 for a different arithmetic operation. Now, SE4-1 that differentiates the electronic control device of this embodiment from that of FIG. 14 will be described below.

In SE4-1 of FIG. 29 that corresponds to the preejection period computing means 162, the preejection period PEP from the Q wave of the induced electro-cardiac wave detected in SE1 to the rising edge of the partial impedance pulse wave $SM_{IMP(P)}$ detected in SE2, and selected as heartbeat synchronous information $I_H$, is directly computed.

With this embodiment, the gate means 79 (SB1 through SB6) takes in the partial impedance pulse wave $SM_{IMP(P)}$ as part of the thorax impedance pulse wave $SM_{IMP}$ detected by the thorax impedance pulse wave detector 64 between the end of the first time $T_1$ starting from the detection of the R wave of the induced electro-cardiac wave and the end of the second time $T_2$. Then, the preejection period computing means 162 (SE4) directly computes the preejection period PEP as the time difference between a time the Q wave of the induced electro-cardiac wave is periodically detected by the electro-cardiac wave detection device 50 and a time a rising edge of the partial impedance pulse wave $SM_{IMP(P)}$ extracted by the gate means 79 (SB1 through SB6) periodically appears. Thus, the determined preejection period PEP is accurate because it is computed by using a rising edge of the partial impedance pulse wave $SM_{IMP(P)}$ that is largely unaffected by noise. Additionally, since this embodiment does not use a microphone for detecting the cardiac operation of pumping out blood, the preejection period PEP can still be measured accurately if the heart sound contains noise.

Figure 30:
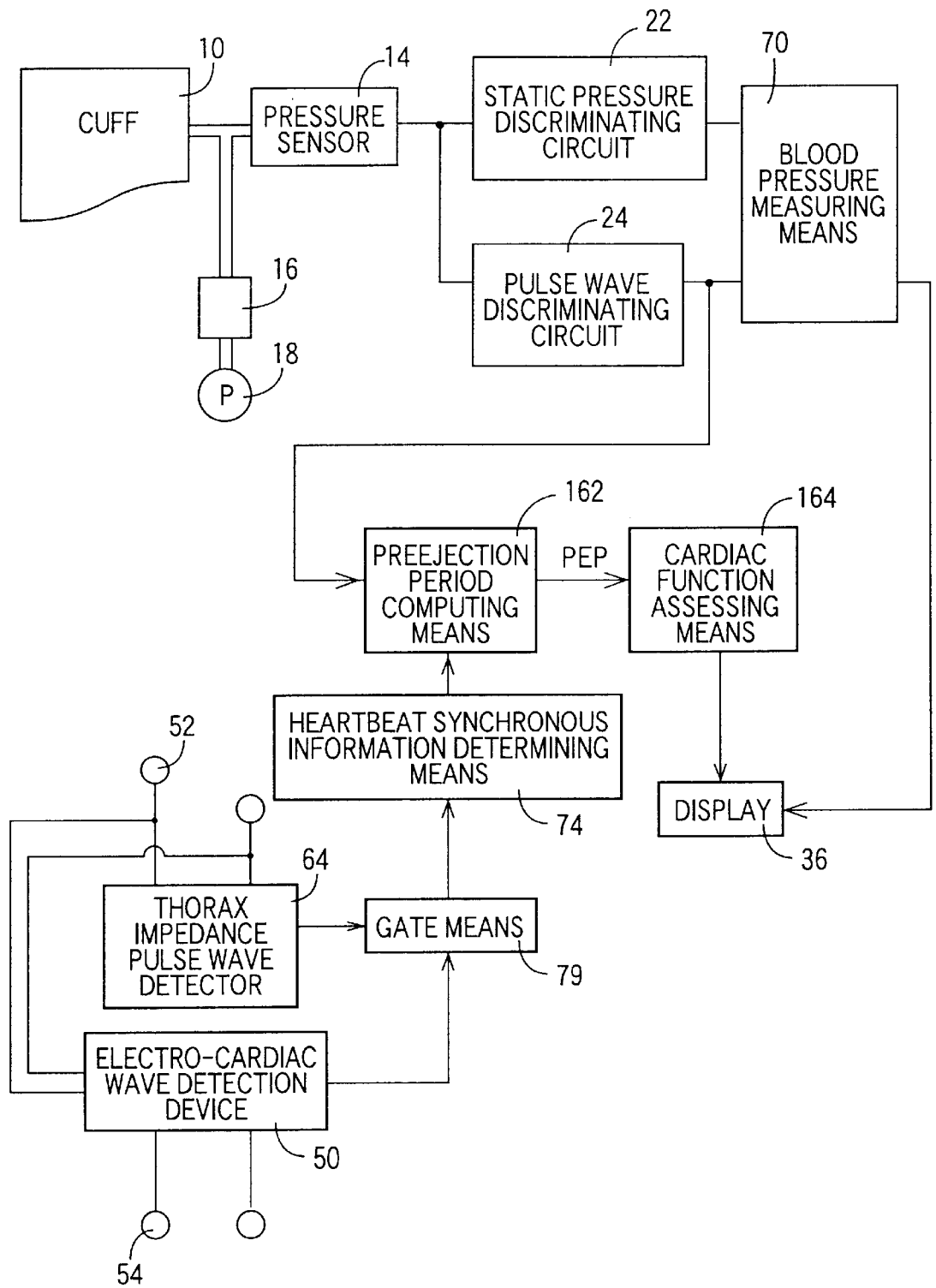
FIG. 30 is a block diagram of another embodiment of a blood pressure measuring apparatus according to the invention and provided with a preejection period measuring apparatus.
Figure 31:
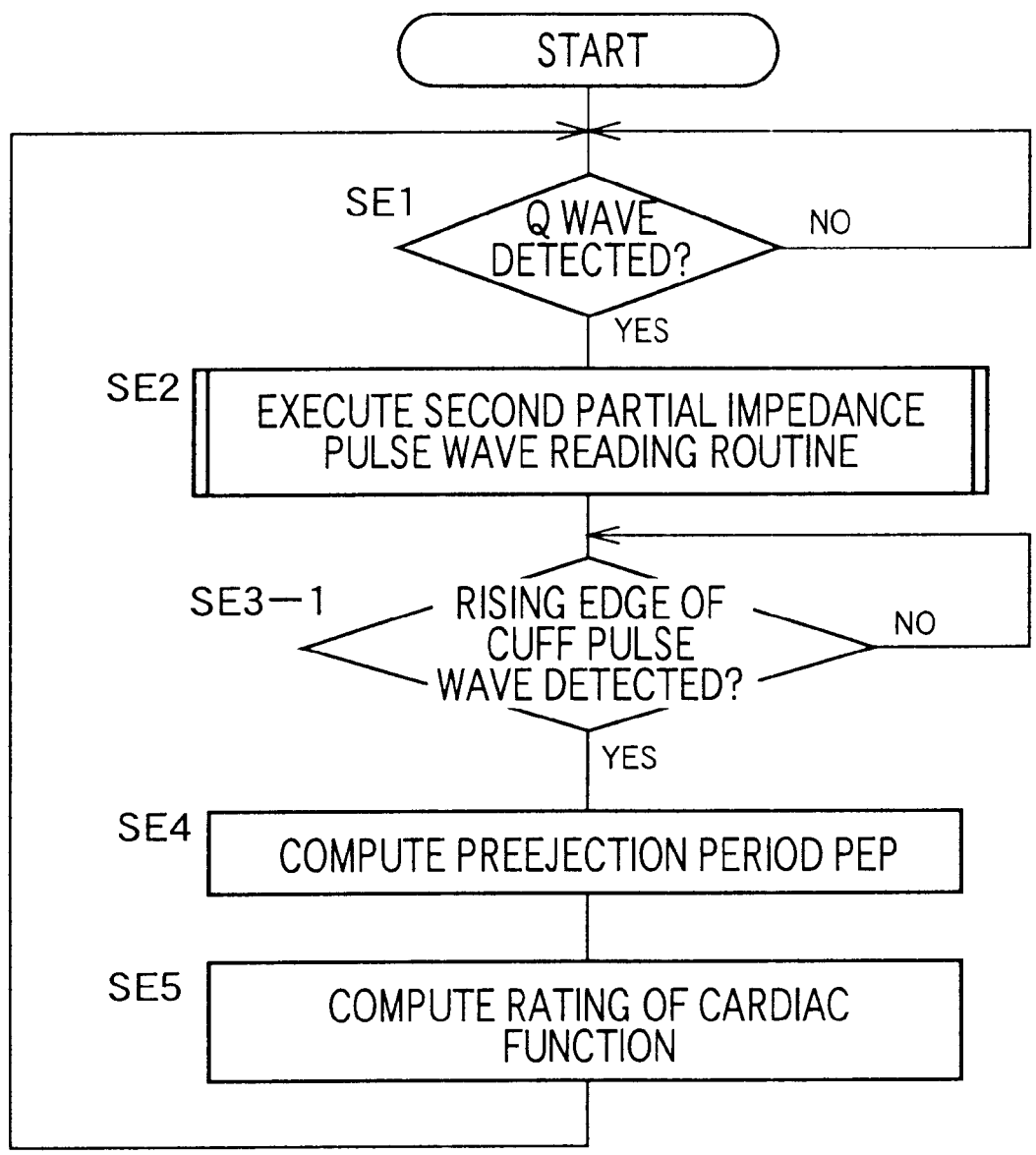
FIG. 31 is a flow chart of an operation of an electronic control device of the embodiment of the blood pressure measuring apparatus of FIG. 30, illustrating the operation of computing the preejection period.

Now, still another embodiment will be described below. FIG. 30 and FIG. 31 of this embodiment correspond to FIG. 27 and FIG. 28 respectively of the immediately preceding embodiment. This embodiment of the apparatus is identical with that of the continuous blood pressure measuring apparatus described earlier by referring to FIG. 20 except for the control function of the electronic control device 28. Furthermore, the control function of the electronic control device 28 of this embodiment differs from that of the embodiment of FIGS. 27 and 28 in that it is not provided with the pressure pulse wave versus blood pressure relationship determining means 146 or the monitored blood pressure determining means 148.

The preejection period computing means 162 (SE4) of this embodiment computes the first time difference $TD_{RP}$ which is the time difference between a time the Q wave of the induced electro-cardiac wave periodically appears and a time a rising edge of the cuff pulse wave that can be detected under pressure of the cuff 10 that is lower than the average blood pressure periodically appears. The preejection period computing means 162 (SE4) of this embodiment also computes the second time difference $TD_{RI}$ which is the time difference between a time a rising edge of the partial impedance pulse wave $SM_{IMP(P)}$ periodically appears and a time a rising edge of the cuff pulse wave periodically appears, and then subtracts the second time difference $TD_{RI}$ from the first time difference $TD_{RP}$ to determine the preejection period PEP. Then, as in one of the preceding embodiments, the cardiac function assessing means 164 (SE5) computes the rating E of the cardiac function based on the obtained preejection period PEP, and causes the display 36 to show the rating E. Thus, this embodiment provides the same advantages as those of the embodiment of FIG. 27.

Additionally, with this embodiment, the pulse wave sensor is composed of the cuff 10, the pressure sensor 14 and the pulse wave discriminating circuit 24, which may be shared by the blood pressure measuring apparatus which includes the blood pressure measuring means 70 to reduce the cost of the apparatus.

Still another embodiment of the blood pressure measuring apparatus according to the invention will be described below by referring to FIG. 32, which is a flow chart of the operation of the electronic control device 28 for computing the preejection period. This embodiment has a configuration similar to that of the blood pressure measuring apparatus of FIG. 20. The flow chart of FIG. 32 is the same as that of FIG. 31 except that SE3-1 is not included.

Figure 32:
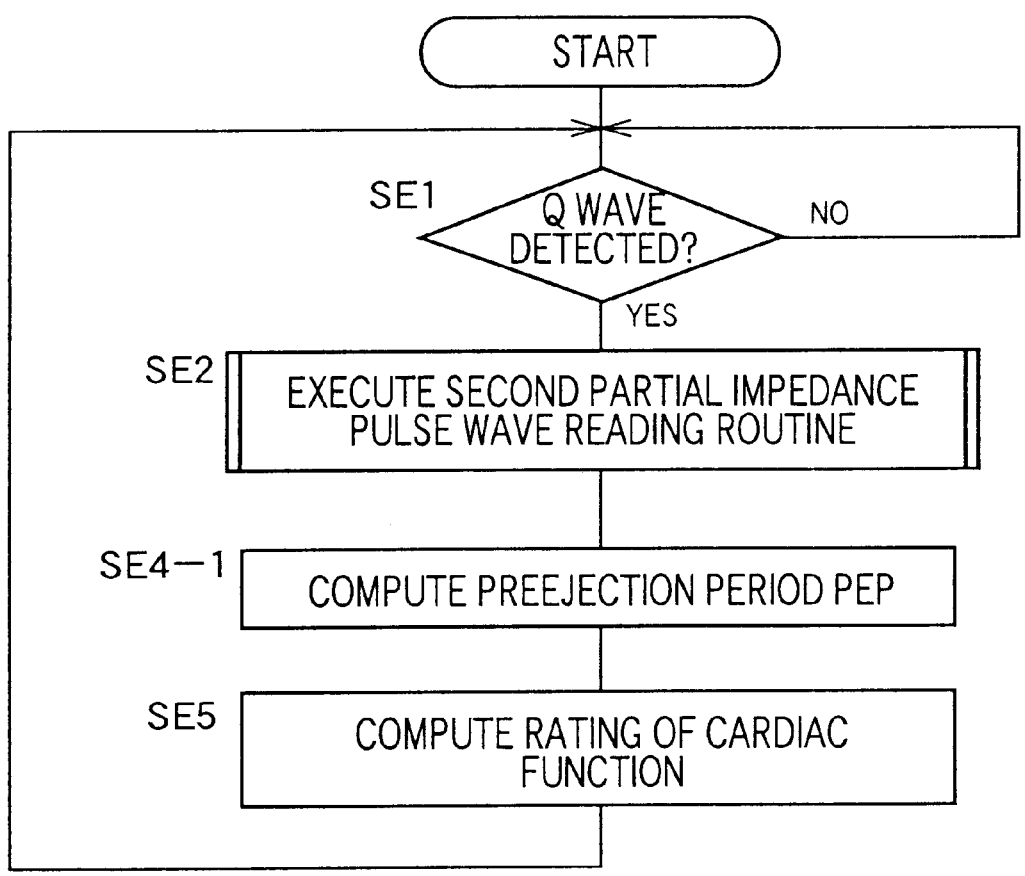
FIG. 32 is a flow chart of an operation of an electronic control device of still another embodiment, illustrating the operation of computing the preejection period.

With this embodiment, in SE4-1 in FIG. 32 that corresponds to the preejection period computing means 162, the preejection period PEP from the Q wave of the induced electro-cardiac wave detected in SE1 to the rising edge of the partial impedance pulse wave $SM_{IMP(P)}$ detected in SE2 is directly computed. Thus, this embodiment provides advantages the same as those obtained by the processing operation of FIG. 29.

Figure 33:
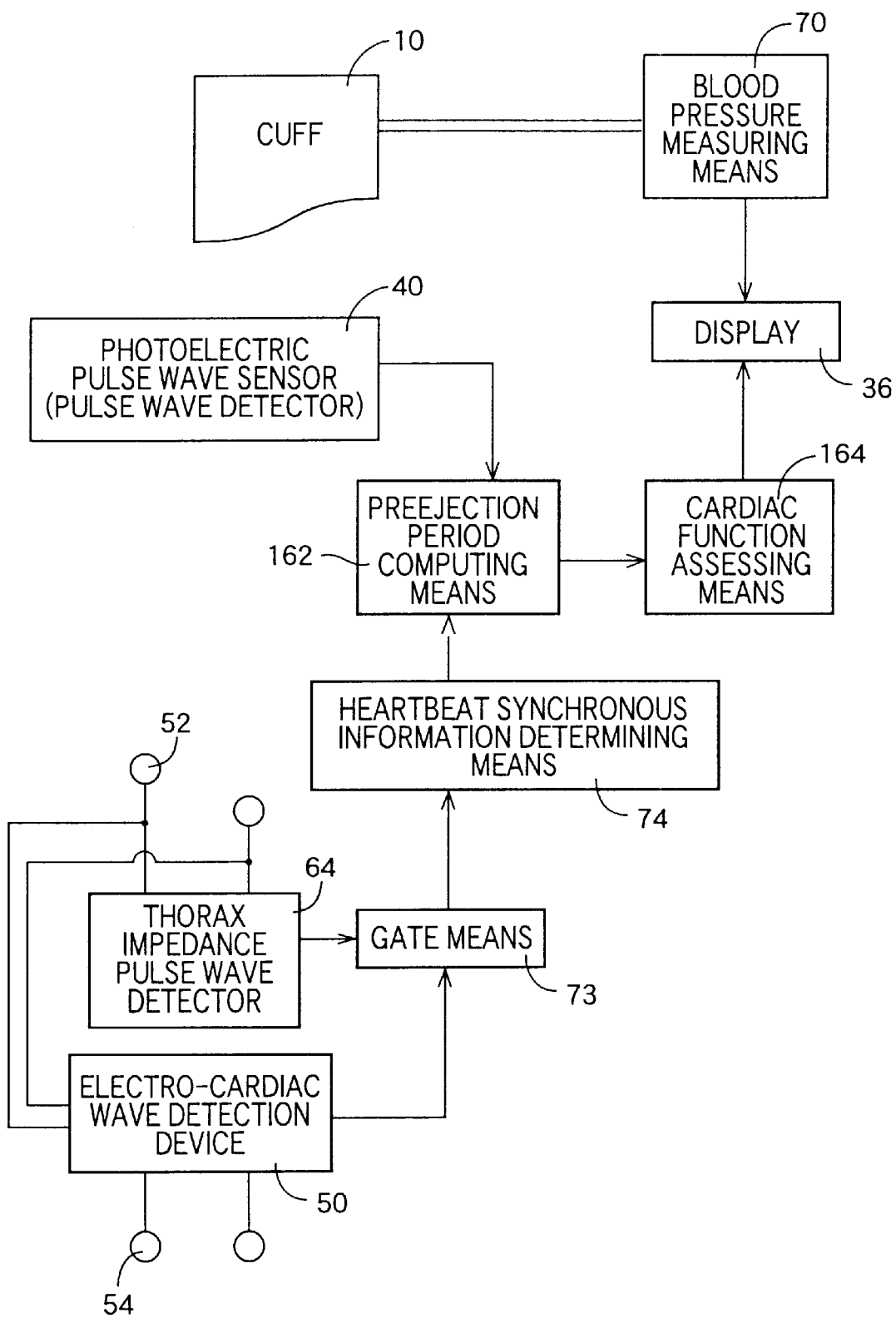
FIG. 33 is a block diagram of another embodiment of a blood pressure measuring apparatus according to the invention and provided with a preejection period measuring apparatus.

Still another embodiment of the invention will be described below by referring to FIGS. 33 and 34, of which FIG. 33 corresponds to FIG. 28. This embodiment has a configuration the same as the embodiment of the blood pressure measuring apparatus 156 of FIG. 24 except for the control function of the electronic control device 28. The block diagram of FIG. 33 differs from that of FIG. 27 in that the pressure pulse wave versus blood pressure relationship determining means 146 and the monitored blood pressure determining means 148 are removed. Also, the gate means 79, which is adapted to determine the period during which it extracts a partial impedance pulse wave $SM_{IMP(P)}$ solely based on the induced electro-cardiac wave, is replaced by the gate means 73, which is adapted to determine the period during which it extracts the partial impedance pulse wave $SM_{IMP(P)}$ based on the induced electro-cardiac wave and the photoelectric pulse wave. Also, the flow chart of FIG. 34 differs from that of FIG. 28 in that SE2 for executing the second partial impedance pulse wave reading routine is replaced by SE2-1 for executing the first partial impedance reading routine, and SE3 for detecting a rising edge of the pressure pulse wave is replaced by SE3-2 for detecting a rising edge of the photoelectric pulse wave.

Like its counterpart of the immediately preceding embodiment, the preejection period computing means 162 (SE4) of this embodiment computes the first time difference $TD_{RP}$ which is the time difference between a time the Q wave of the induced electro-cardiac wave periodically appears and a time a rising edge of the photoelectric pulse wave periodically appears. Also, the preejection period computing means 162 (SE4) of this embodiment computes the second time difference TP which is the time difference between a time a rising edge of the partial impedance pulse wave $SM_{IMP(P)}$ periodically appears and a time a rising edge of the photoelectric pulse wave periodically appears, and then subtracts the second time difference TP from the first time difference $TD_{RP}$ to determine the preejection period PEP. Then, also as in the immediately preceding embodiment, the cardiac function assessing means 164 (SE5) computes the rating E of the cardiac function based on the obtained preejection period PEP, and causes the display 36 to show the rating E. Thus, this embodiment provides the same advantages as those of the embodiment of FIG. 27. Additionally, the end of the period during which the impedance pulse wave $SM_{IMP}$ is taken in by the gate means 73 (SB1 through SB5) is selected based on the photoelectric pulse wave that is largely unaffected by electromagnetic noise and hence can be determined accurately and reliably.

Finally, this embodiment is designed to include a photoelectric pulse wave sensor 40 operating as the pulse wave detector. When the pulse oximeter is also included, as illustrated in FIG. 13, which is provided with the photoelectric pulse wave sensor for detecting the pulse wave by using light showing two wavelengths for irradiation, the photoelectric pulse wave sensor of the pulse oximeter can be shared by the pulse wave detector to reduce the cost of the pulse wave detector.

While the present invention is described by referring to the accompanying drawings that illustrate preferred embodiments of the invention, the present invention is by no means limited to these embodiments.

For instance, the thorax impedance pulse wave detector 64, which is adapted to detect the impedance of the thorax of a living body, is used as the impedance pulse wave detector in any appropriate one of the above described embodiments. It may be replaced by an impedance pulse wave detector of any other type for detecting the impedance of the living body at positions out of the thorax as long as it is adapted to measure the impedance at two positions with the heart interposed between them. This is because the impedance carries an impedance pulse wave containing a heartbeat synchronous component in a multiplexed form. For instance, an impedance pulse wave detector adapted to measure the impedance between two hands may be used.

While the start of the intake period for taking in a thorax impedance pulse wave $SM_{IMP}$ is determined based on the R wave of the induced electro-cardiac wave in any appropriate one of the above described embodiments, the start of an intake period may alternatively be determined based on the Q wave or an S wave of the induced electro-cardiac wave. When, either the Q wave or the S wave is used in place of the R wave, the first time $T_1$ and the second time $T_2$ may be same as those of the R wave or different from them and determined based on one or more tests conducted in advance.

In any appropriate one of the above described embodiments either the photoelectric pulse wave sensor 40, the photoelectric pulse wave detection probe 90 provided in the pulse oximeter 88, a combination of the cuff 10, the pressure sensor 14 and the pulse wave discriminating circuit 24, or the pressure sensor 132 is used for the pulse wave detector. Alternatively, an impedance pulse wave sensor for detecting changes in the impedance of a part of a living body by way of the electrodes fitted to one of the fingers of one of the feet of the living body may be used. Such an impedance pulse wave sensor typically includes at least one pair of electrodes to be held in contact with the epidermis of a living body and separated from each other by a predetermined distance, and is adapted to output an impedance pulse wave corresponding to the volume of blood in the tissues of the living body located between the two electrodes.

While the blood pressure of a living body is monitored based on the pulse wave propagation velocity PWV that is determined at each heartbeat in any appropriate one of the above described embodiments, it is not essential to monitor the blood pressure at each heartbeat. Alternatively, the blood pressure of a living body may be monitored in periods of several heartbeats, several seconds or after every period of several tens of seconds based on the pulse wave propagation velocity PWV.

The pulse wave propagation velocity related information computing means 75 of any appropriate one of the above described embodiments computes the pulse wave propagation velocity PWV based on the propagation time TP from a rising edge of the partial impedance pulse wave $SM_{IMP(P)}$ to a rising edge of the photoelectric pulse wave (or the pressure pulse wave or the cuff pulse wave). Alternatively, any other periodically appearing point on such a pulse wave such as an upper peak point, a point showing the largest inclination or an inflection point may be used.

The pulse wave propagation velocity related information computing means 75 of any appropriate one of the above described embodiments computes the propagation time TP which is the time difference between a time a rising edge of the partial impedance pulse wave $SM_{IMP(P)}$ periodically appears and a time a rising edge of the photoelectric pulse wave $SM_2$ periodically appears. Alternatively, the propagation time TP maybe determined by subtracting the second time difference $TD_{RI}$, which is the time difference between a time the Q wave of the induced electro-cardiac wave appears and a time a rising edge of the partial impedance pulse wave $SM_{IMP(P)}$ periodically appears, from the first time difference $TD_{RP}$, which is the time difference between a time the Q wave of the induced electro-cardiac wave periodically appears and a time the rising edge of the partial impedance pulse wave $SM_{IMP(P)}$ periodically appears.

The above described blood pressure measuring means 70 or 82 is adapted to determine the blood pressure of the living body based on the change in the cuff pulse wave in the process of gradually lowering the cuff pressure $P_c$. Alternatively, it may be adapted so as to determine the blood pressure of the living body based on the change in the cuff pulse wave in the process of gradually raising the cuff pressure $P_c$.

The above described blood pressure measuring means 70 or 82 is adapted to determine the blood pressure of the living body based on the change in the amplitude of the pressure pulse wave that changes as a function of the pressure of the cuff 10 according to the well known oscillo-metric method. Alternatively, the method of Korotkoff sounds may be used to determine the blood pressure based on the Korotkoff sounds that can be generated and extinguished as a function of the pressure of the cuff 10.

While the above described thorax impedance pulse wave detector 64 is adapted to discriminate the thorax impedance pulse wave from a thorax impedance signal by using a band pass filter between 0.5 and 30 Hz, an active filter realized by computer software may alternatively be used to discriminate the thorax impedance pulse wave.

While a blood pressure measuring apparatus according to the invention either includes the pulse wave propagation velocity measuring apparatus or the preejection period measuring apparatus, whenever appropriate, the pulse wave propagation velocity measuring apparatus and the preejection period measuring apparatus may be used independently without departing from the scope of the invention.

The above described embodiments may be appropriately altered or modified without departing from the spirit and the scope of the present invention.

What is claimed is:

1. A heartbeat synchronous information acquiring apparatus provided with an impedance pulse wave detector for detecting an impedance pulse wave of a living body containing heartbeat synchronous components between a pair of electrodes fitted to predetermined positions of the living body with a heart interposed therebetween in order to acquire the heartbeat synchronous information generated synchronously with heartbeats of the living body based on the impedance pulse wave, said apparatus comprising:

an induced electro-cardiac wave detection device for continuously detecting an induced electro-cardiac wave of said living body;

gate means for extracting a partial impedance pulse wave from the impedance pulse wave by taking in the impedance pulse wave for an intake period based on the time of detection of a predetermined part of the induced electro-cardiac wave by the induced electro-cardiac wave detection device; and heartbeat synchronous information determining means for determining a periodically appearing predetermined part of the partial impedance pulse wave extracted by the gate means as heartbeat synchronous information.

2. The heartbeat synchronous information acquiring apparatus according to claim 1, wherein said intake period of said gate means is from the end of a predetermined first time period starting from the time of detection of the predetermined part of the induced electro-cardiac wave by the induced electro-cardiac wave detection device to the end of a predetermined second time period starting from the time of detection of the predetermined part, said second time period being longer than said first time period.

3. A heartbeat synchronous information acquiring apparatus according to claim 1, further comprising a photoelectric pulse wave sensor for detecting a photoelectric pulse wave at a part irradiated with light, said sensor being provided with a light source for irradiating a skin of said living body with light, and a photo detector for detecting transmitted or reflected light originating from said light source, the intake period of said gate means being from the end of a first time period starting from the time of detection of the predetermined part of the induced electro-cardiac wave by the induced electro-cardiac wave detection device to the time of detection of the predetermined part of the photoelectric pulse wave by said photoelectric pulse wave sensor.

* * * * *